US008640940B2

(12) United States Patent  
Ohdaira

(10) Patent No.: US 8,640,940 B2  
(45) Date of Patent: Feb. 4, 2014

(54) SURGICAL SYSTEM AND SURGICAL METHOD FOR NATURAL ORIFICE TRANSLUMINAL ENDOSCOPIC SURGERY (NOTES)

(75) Inventor: Takeshi Ohdaira, Shimotsuke (JP)

(73) Assignee: Educational Foundation Jichi Medical University, Tochigi (JP)

( * ) Notice: Subject to any disclaimer, the term of this patent is extended or adjusted under 35 U.S.C. 154(b) by 464 days.

(21) Appl. No.: 12/989,730

(22) PCT Filed: Apr. 28, 2009

(86) PCT No.: PCT/JP2009/058328  
§ 371 (c)(1),  
(2), (4) Date: Jan. 7, 2011

(87) PCT Pub. No.: WO2009/133875  
PCT Pub. Date: Nov. 5, 2009

(65) Prior Publication Data  
US 2011/0095067 A1  Apr. 28, 2011

(30) Foreign Application Priority Data  
Apr. 30, 2008  (JP) ................ 2008-119277

(51) Int. Cl.  
*A61B 17/115* (2006.01)  
*A61B 18/00* (2006.01)

(52) U.S. Cl.  
USPC .............. 227/175.1; 227/179.1; 227/180.1; 227/19

(58) Field of Classification Search  
USPC .............. 227/175.1, 179.1, 180.1, 19  
See application file for complete search history.

(56) References Cited

U.S. PATENT DOCUMENTS

| | | | |
|---|---|---|---|
| 5,197,649 | A | 3/1993 | Bessler et al. |
| 5,389,098 | A | 2/1995 | Tsuruta et al. |
| 5,395,030 | A | 3/1995 | Kuramoto et al. |
| 5,588,579 | A | 12/1996 | Schnut et al. |
| 5,639,008 | A | 6/1997 | Gallagher et al. |
| 5,758,814 | A | 6/1998 | Gallagher et al. |
| 5,855,312 | A | 1/1999 | Toledano |
| 6,517,565 | B1 | 2/2003 | Whitman et al. |
| 8,459,523 | B2 | 6/2013 | Whitman |
| 2003/0105478 | A1 | 6/2003 | Whitman et al. |
| 2005/0080342 | A1 | 4/2005 | Gilreath et al. |

FOREIGN PATENT DOCUMENTS

| | | |
|---|---|---|
| EP | 1637064 | 3/2006 |
| JP | 2000-166932 | 6/2000 |

*Primary Examiner* — Michelle Lopez  
(74) *Attorney, Agent, or Firm* — Greer, Burns & Crain, Ltd.

(57) ABSTRACT

A system and method for use in NOTES is provided for reducing surgical invasiveness. An insertion body that is connected by an anvil assembly and joined to a thin wire guide or electric guide wire, is inserted via a natural orifice into a hollow organ so as to incise and remove a diseased or defective site from the hollow organ by using a pair of or front-end/rear-end linear cutters of a linear cutting/stapling device or linear stapler, after which the two cut ends of the tract are anastomosed and recovered by a circular anastomosis surgical stapler that is provided with the system.

23 Claims, 21 Drawing Sheets

(a)

(b)

(a)

(b)

(a)

(b)

(a)

(b)

(a)

(b)

(a)

(b)

US 8,640,940 B2

SURGICAL SYSTEM AND SURGICAL METHOD FOR NATURAL ORIFICE TRANSLUMINAL ENDOSCOPIC SURGERY (NOTES)

BACKGROUND

The present invention relates to a surgical system and method by which a diseased or defective site of a hollow organ of a living body (hereinafter "body") is resected after which the cut-end sections of the hollow organ are stapled, and particularly relates to a system and method for use in Natural Orifice Transluminal Endoscopic Surgery (Hereinafter "NOTES") which reduces the invasiveness of surgical procedures by eliminating the need for large-scale surgery, such as that involving a conventional abdominal incision.

Previously, in surgery in which a diseased or defective site of a hollow organ, for example a digestive tract, is resected so that the cut-end sections of the remainder of the tract are stapled, as in lesion-resection surgery of an intestinal tract, including cancer resection, there is no choice but to incise the abdomen from the outside of the body and to resect the lesion from outside of the lesion, and then to staple the cut-end sections from the outside thereof. Recently, as described below, a surgical method has been proposed and utilized in which the respective end sections of a diseased or defective site of an intestinal tract are cut off by using a linear-cutting/stapling device (linear stapler) (hereinafter "linear stapler") in such a way that the respective end sections are cut linearly in the transverse direction from the outside, and at the same time the cut-end sections of the remainder of the intestinal tract are closed by purse-string-like linear-stapling suturing, after which a circular anastomotic surgical stapler is used to staple the two cut-end sections of the remainder of the intestinal tract, and at the same time the cut-end sections of the remainder of the intestinal tract that have been closed by purse-string-like linear-stapling suturing are cut off.

In the following explanation, in a body's natural orifice or separately made endoscopic hole that is made so that endoscopic instruments can be inserted into the body (hereinafter "endoscopic hole"), the portion of the device or the part of a body in the body's inward direction is called the "front end" or "front section," and the portion of the device or the part of the body in the body's outward direction is called the "rear end" or "rear section."

An existing circular anastomotic surgical stapler, for example as illustrated in FIG. 39 (prior art), includes: (1) a head assembly for ligation 1060 that has an anvil component 1000 at the front end; (2) a head component 1061 that is positioned opposite to the anvil component 1000 and that has anastomotic staples and a circular cutter used for circular anastomosis of the two cut-end sections of the hollow organ; (3) a shaft assembly 1050, which is an insertion body to be inserted into the hollow organ, and which has a long, flexible support shaft 1070; (4) an actuator hand assembly 1086 that is connected to the shaft assembly 1050 and that controls the driving of the circular cutter and anastomotic staples; and wherein the anvil component 1000 is constructed so that it is releasably mounted to the head component 1061 via an anvil shaft 1104 and a trocar portion (not shown) that is connected thereto. (See, e.g., FIGS. 5-47 of Patent Document 1.)

In contrast, as illustrated in FIG. 40 (prior art), an existing linear stapler 1500 includes: (1) an end effector 1503 that has an upper jaw 1504 that opens and closes, and a lower jaw 1505 that is positioned opposite to the upper jaw 1504 and that has one or more linear rows of staples and a linear cutter; (2) an insertion body 1501, to be inserted via an endoscopic hole, that has a long, flexible support shaft 1506 connected to the end effector 1503; and (3) an operating assembly 1502 that is connected to the support shaft 1506 and that controls the driving of one or more linear rows of staples and of the linear cutter. (See, e.g., FIG. 1 of Patent Document 2.)

PRIOR ART DOCUMENTS

Patent Document 1: Japanese Unexamined Patent Application Publication No. 2000-166932
Patent Document 2: Japanese Unexamined Patent Application (Translation of PCT Application) Publication No. 2003-50410 (Priority application number: U.S. Ser. No. 09/351,534)

SUMMARY

Problems to Be Solved by the Invention

Surgical procedures using the circular anastomotic surgical stapler disclosed in Patent Document 1 (FIG. 39) and the linear stapler disclosed in Patent Document 2 (FIG. 40), in which a diseased or defective part of the intestinal tract is cut off and the cut-end sections of the remainder of the intestinal tract are stapled, as will now be described.

The shaft assembly 1050 of the circular anastomotic surgical stapler is inserted via, e.g., the anus under the condition that the anvil component 1000 is connected to the head component 1061; when the anvil component 1000 fully passes near the end of the diseased or defective site of the intestinal tract in the direction of the upper end of the intestinal tract (the front end), the anvil component 1000 is pushed and separated from the head component 1061; the shaft assembly 1050 on the side of head component 1061 retracts until the head component 1061 is located near the end of the diseased or defective site of the intestinal tract in the direction towards the anus (the rear end); and by using the linear stapler 1500, which is introduced from the opened abdominal cavity, the respective front and rear ends of the diseased or defective site of the intestinal tract are cut off and removed from the remainder of the intestinal tract, and, at the same time, the cut-end sections are closed by purse-string-like linear-stapling suturing.

In this case, the cutting and linear-stapling suturing of the two end sections of the diseased or defective site are performed linearly in the transverse direction of the intestinal tract by one or more linear rows of staples and a linear cutter (both not shown) that are driven from the rear end to the front end inside the lower jaw 1505.

Next, from outside of the site of the incisional opening of the abdomen, the anvil shaft 1104 and the trocar portion (both not shown), which are respectively mounted on either the anvil component 1000 or the head component 1061, and which can be coupled to or decoupled from each other, are inserted by hand via the cut-end sections closed by purse-string-like linear-stapling suturing of the remainder of the intestinal tract, and the cut-end sections are tied tightly to the anvil shaft 1104 and the trocar portion, which are exposed, in a purse-string-like linear-stapling suturing manner (both not shown).

Then, under the condition that the anvil component 1000 is pulled by a human hand to the head component 1061 so that the anvil component and the head component are coupled together and positioned opposite to the anvil shaft 1104 and the trocar portion, from the outside of the site of incision opening of the abdomen, the ends of the purse-string-like linear-stapling suturing sites toward both the mouth and the anus of the intestinal tract are put together and stapled, and at the same time the purse-string-like linear-stapling suturing sites of the intestinal tract are circularly cut off and removed from the remainder of the intestinal tract. At this time, pulling of the anvil component 1000 to the head component 1061, performing circular anastomosis, and cutting off of the ends of the purse-string-like linear-stapling suturing sites, are done semi-automatically via hand operation of the actuator handle assembly 1086.

As stated above, despite the development up to now of various linear staplers and circular anastomotic surgical staplers, and despite progress such that the shaft assembly 1050, which is the insertion body of the circular anastomotic surgical stapler, can be inserted into a hollow organ via a natural orifice (e.g., the anus), such procedures as (1) tying the ends of cut-end sections of the remainder of the intestinal tract to the anvil shaft 1104 and the trocar portion in a purse-string-like linear-stapling suturing manner using a ligature after the diseased or defective site of the intestinal tract has been cut off by using the linear cutting/stapling device, and (2) connecting the anvil component 1000 and the head component 1061 via the anvil shaft 1104 and the trocar portion, must be performed by hand from outside the site of incisional opening of the body, and accordingly, large-scale operations are still required.

Therefore, the above-mentioned conventional methods have substantial problems in that the operations require much time, effort, and expense; the treatment periods are prolonged; and they involve excessive surgical invasiveness.

Also, although recent publications (e.g., Patent Document 1) proclaim that a circular anastomotic surgical stapler "makes automatic stapling" of the cut-end sections of the diseased or defective site of a hollow organ of a body, such a device's operation does not in reality deserve to be referred to as "automatic stapling," because (1) tying the near ends of the cut-end sections of the hollow organ to the anvil shaft and the trocar portion in a linear-stapling suturing manner using a ligature after the diseased or defective site of the hollow organ has been cut off from the remainder of the hollow organ, and (2) connecting the anvil component 1000 and the head component 1061 via the anvil shaft 1104 and the trocar portion, must be performed by hand from outside the site of incisional opening of the body.

The present invention has been made in light of the above problems of the existing technologies, and the objectives of the present invention are to reduce the time and invasiveness of operations by eliminating the need for large-scale surgery, such as that which requires an incision of the abdomen of a body, and to provide a method and system that are that excellent in operability, reliability, and economic efficiency for use in NOTES.

DESCRIPTION OF THE INVENTION

The system for use in NOTES is explained in Claim 1 and includes a circular anastomosis surgical stapler that comprises:

(1) an anvil assembly that has an anvil shaft on which a trocar protrudes rearward along the main axis (X-axis) at the rear end of the anvil assembly so that the anvil assembly is used as the front end of the circular anastomosis surgical stapler;

(2) an insertion body that is positioned opposite to the anvil assembly and that includes (a) a head assembly that has (1) a circular cutter (annular blade) for cutting off, in the cylindrical direction, a specified section of a hollow (tubular) organ, and (2) one or more annular rows of anastomotic staples for use in circular anastomosis of the two cut-end sections of the remainder of the hollow organ, and (2) a long, flexible support shaft that is connected to the head assembly;

(3) an operating assembly that is connected to the insertion body and that controls the driving of the circular cutter (annular blade) and the anastomotic staples;

(4) a thin guide wire that is inserted via the insertion body and that is connected to the acute (rear) end of the trocar so as to be capable of being taken up and released; and (5) a coupling (engaging) mechanism that includes a locked portion and a locking portion that are engageable with each other, with the locked portion provided at the anvil shaft and the locking portion provided at the main axis of the head assembly, and that releasably mounts the anvil assembly to the head assembly;

and wherein said system (1) the insertion body to which the anvil assembly is connected is inserted via a natural orifice of the living body (hereinafter "body") and into a hollow organ that has a diseased or defective site;

(2) the anvil assembly is detached (removed) from the head assembly and is temporarily left near the front end of the diseased or defective site of the hollow organ;

(3) the head-assembly-side insertion body retracts to near the rear end of the diseased or defective site, so as to create a space between the anvil assembly and the insertion body;

(4) after said space has been created between the anvil assembly and the insertion body, there is inserted into the body—via an endoscopic hole that is opened on the body so that endoscopic instruments can be inserted into the body (hereinafter "endoscopic hole") to near the diseased or defective site of the hollow organ—a linear stapler that has one or more linear cutters that cut off, straight in the transverse direction, a specified section of the hollow organ, and one or more linear rows of suture staples that staple together the respective cut-end sections of the remainder of the hollow organ;

(5) the diseased or defective site of the hollow organ is cut off and removed from the remainder of the hollow organ and, at the same time, the respective cut-end sections of the remainder of the hollow organ are closed by purse-string-like linear-stapling suturing straight in the transverse direction by a procedure outside the hollow organ using the linear stapler; and (6) then the circular anastomotic surgical stapler performs circular anastomosis of the two cut-end sections of the remainder of the hollow organ, and at the same time cuts off the cut-end sections that have closed by purse-string-like linear-stapling suturing of the remainder of the hollow organ by a procedure inside the hollow organ, so that the sections are again interconnected.

The invention of Claim 2 is a system for use in NOTES and includes a circular anastomosis surgical stapler that comprises:

(1) "an anvil assembly to whose rear end is connected an anvil shaft whose rear end connects releasably to an acute part that includes a trocar, so that said anvil shaft protrudes rearward along the main axis (X-axis) so that the anvil assembly is used as the front end of the circular anastomotic surgical stapler;

(2) an insertion body that is positioned opposite to the anvil assembly and that includes a head assembly that has (1) a circular cutter (annular blade) for cutting off in the cylindrical direction a specified section of the hollow (tubular) organ, (2) one or more annular rows of anastomotic staples that are used in circular anastomosis of the two cut-end sections of the remainder of the hollow organ, and (3) a long, flexible support shaft that is connected to the head assembly;

(3) an operating assembly that is connected to the insertion body and that controls the driving of the circular cutter (annular blade) and of one or more rows of anastomotic staples;

(4) a thin guide wire that is inserted via the insertion body and that is connected to the acute (rear) end of the trocar so as to be capable of being taken up and released; and (5) a coupling (engaging) mechanism that (a) includes a locked portion and a locking portion that are engageable with each other, with the locked portion provided at the anvil shaft and the locking portion provided at the main axis of the head assembly, and (b) releasably mounts the anvil assembly to the head assembly;

and wherein said system (1) the insertion body to which the anvil assembly is connected is inserted via a natural orifice of the body into the hollow organ that has a diseased or defective site;

(2) said anvil assembly is detached (removed) from the head assembly and is temporarily left near the front end of the diseased or defective site of the hollow organ, and the head-assembly-side insertion body retracts to near the rear end of the diseased or defective site, so as to create a space between the anvil assembly and the insertion body;

(3) after said space has been created between the anvil assembly and the insertion body, there are inserted into the body to near the diseased or defective site of the hollow organ via an endoscopic hole, a linear stapler that has (a) one or more linear cutters that cut off, straight in the transverse direction, a specified section of the hollow organ, and (b) one or more linear rows of suture staples that staple straight in the transverse direction the respective cut-end sections of the remainder of the hollow organ;

(4) said diseased or defective site of the hollow organ is cut off and removed from the remainder of the hollow organ, and at the same time the respective cut-end sections of the remainder of the hollow organ are closed by purse-string-like linear-stapling suturing straight in the transverse direction by a procedure outside the hollow organ using the linear stapler; and (5) then said circular anastomotic surgical stapler performs circular anastomosis of the two cut-end sections of the remainder of the hollow organ, and at the same time cuts off the cut-end sections that have been closed by purse-string-like linear-stapling suturing of the remainder of the hollow organ by a procedure inside the hollow organ, so that the sections are again interconnected.

The invention of Claim 3 is a system according to Claim 1 for use in NOTES, and wherein there are accommodated near the connection between the head assembly and the support shaft: (a) a push-tube drive mechanism that moves a push tube forward or backward, with the push tube being provided to allow the anvil assembly to connect with or detach from the head assembly, (b) a staple/cutter driver mechanism that drives the anastomotic staples and the circular cutter (annular blade), and (c) a take-up unit that takes up the thin guide wire; with the operations of the mechanisms and take-up unit being remotely controlled via the operating assembly.

The invention of Claim 4 is a system according to Claim 3 for use in NOTES, and wherein a wireless transmitter/receiver and a battery are further provided near the connection between the head assembly and the support shaft, with the push-tube drive mechanism, the staple/cutter driver mechanism, and the take-up unit being controlled by wireless remote control.

The invention of Claim 5 is a system according to any of the preceding claims for use in NOTES, and wherein the coupling (engaging) mechanism includes:

(1) a locked portion of a convex-shaped anvil shaft that is provided near the trocar;

(2) a split-capture part that is mounted on the center of the head assembly and that is divided circumferentially into a plurality of pieces so as to form a concave shape, and that engageably fits on the locked portion so as to capture the locked portion;

(3) a locking portion, which is provided at the front end of the push tube and is able to move forward and backward so as to allow the anvil assembly to connect with or detach from the head assembly, and that has a plurality of resilient support members that flexurally and elastically support the split-capture part so as to open, without restraint in the diameter-expanding direction, the respective pieces of the split-capture part from the main axis (X0-axis) of the head assembly; and (4) a lock-adjustment tube that fits on the push tube so as to be able to move forward and backward, that acts so that the front end moves forward to the rear end of the locking portion, so as to press the resilient support member from the outside and to close the split-capture part in the diameter-reducing direction, and so that the front end moves backward from the resilient support member so as to open the split-capture part in the diameter-expanding direction.

The invention of Claim 6 is a system according to any of Claims 1, 2, or 5, for use in NOTES, and wherein are accommodated near the connection portion between the head assembly and the support shaft:

(1) a push-tube drive mechanism that moves a push tube forward or backward, with said push tube being provided to allow the anvil assembly to connect with or detach from the head assembly, (2) a lock-adjustment tube mechanism that moves the lock-adjustment tube forward and backward so as to allow the locking portion to become engaged with and disengaged from the locked portion, and (3) a staple/cutter driver mechanism that allows the anastomotic staples and the circular cutter (annular blade) to be driven (pushed out) or retracted; with the operations of said mechanisms remotely controlled via the operating assembly.

The invention of Claim 7 is a system according to Claim 6 for use in NOTES, and wherein a wireless transmitter/receiver and a battery are further provided near the connection portion between the head assembly and the support shaft, with the push-tube drive mechanism, the lock-adjustment tube mechanism, and the staple/cutter driver mechanism being controlled by wireless remote control.

The invention of Claim 8 is a system according to Claim 1 or Claim 2 for use in NOTES, and wherein the thin wire guide is an electric guide wire consisting of an electric conductor, with the front end of the electric guide wire being connected to the acute (rear) end of the trocar via a monopolar electrode;

the trocar consists of an insulator or formed separately on the anvil shaft via an insulator and the two purse-string-like linear-stapling suturing sites of the remainder of the hollow organ, on the anvil-assembly side and the head-assembly side, respectively are (1) cauterized successively by conducting a monopolar current to the monopolar electrode via the electric guide wire that has been taken up, and (2) inserted by the trocar via both of said suturing sites so that said suturing sites will be opened.

The invention of Claim 9 is a system according to Claim 8 for use in NOTES, and wherein the monopolar electrode is buried in the rear end of the trocar, with a small area of the monopolar electrode being exposed at the outer surface of the rear end of the trocar.

The invention of Claim 10 is a system according to Claim 8 or Claim 9 for use in NOTES, and wherein the monopolar electrode is exposed in a narrow band-like manner of appropriate length in the axial direction at the outer peripheral surface of the rear end of the trocar.

The invention of Claim 11 is a system according to any of Claims 8☐10 for use in NOTES, and wherein the anvil shaft to which the trocar is coupled is also coupled to a rotary means by being rotatably supported by the anvil-shaft support, and is rotated by the rotary means when a monopolar current is conducted to the monopolar electrode.

The invention of Claim 12 is a system according to any of Claims 8☐11 for use in NOTES, and wherein the acute part is releasably connected at the rear end of the anvil assembly and penetrates both purse-string-like linear-stapling suturing sites of the hollow organ on the anvil-assembly side and the head-assembly side that are cauterized successively via the trocar, and detaches (removes) from the anvil shaft so as to be pulled into the head assembly.

The invention of Claim 13 is a system according to Claim 2 or Claim 12 for use in NOTES, and wherein there is provided an anvil-assembly connecting aid that (a) is inserted so as to be able to be withdrawn from the rear end of the operating assembly to the front end of the head assembly via the inside of the support shaft, (b) consists of a trocar-like acute part, with the front end thereof being formed like a trocar, penetrating via the split-capture portion of the locking part, and (c) has a long, flexible shaft member that is connected to the trocar-like acute part and that aids the anvil assembly in again being coupled to the head assembly.

The invention of Claim 14 is a system according to any of the preceding claims for use in NOTES, and wherein the anvil assembly has an anvil-assembly-attitude control mechanism that supports the anvil shaft and automatically controls the attitude of the anvil assembly in relation to the anvil shaft so that the main axis of the anvil shaft substantially corresponds to the main axis of the head assembly (X0-axis).

The invention of Claim 15 is a system according to Claim 14 for use in NOTES, and wherein the anvil-assembly-attitude control mechanism includes: (a) a biaxial oscillating mechanism that can oscillate along the two axes (Y-axis and Z-axis) that meet at right angles with the main axis of the anvil shaft (X-axis), (b) angle sensors, mounted on the connection portion of the anvil shaft, for the Y-axis and Z-axis and (c) a drive means that drive the biaxial oscillating mechanism along Y-axis and Z-axis respectively.

The invention of Claim 16 is a system according to Claim 15 for use in NOTES, and wherein the biaxial oscillating mechanism consists of a gimbal mechanism in which a second frame able to oscillate along the Y-axis is provided on a first frame that is fixed inside the anvil assembly, and an anvil-shaft support able to oscillate along the Z-axis and supporting the anvil shaft is provided on the second frame.

The invention of Claim 17 is a system according to either Claim 15 or Claim 16 for use in NOTES, and wherein the drive means consist of servomotors that control the drive of the biaxial oscillating mechanism along the Y-axis and the Z-axis respectively.

The invention of Claim 18 is a system according to Claim 17 for use in NOTES, and further including an anvil-assembly-attitude control mechanism that comprises:

a head-assembly-side transmitter/receiver that is provided inside the head assembly and that wirelessly transmits the output of angle sensors that are located along the two axes (Y0-axis and Z0-axis) and that meet at right angles with the central axis (X0-axis) of the head assembly;

an anvil-assembly-side transmitter/receiver that receives from the head-assembly-side transmitter/receiver the output of angle sensors located along the two axes (Y0-axis and Z0-axis);

an angle-command generator (1) that has (a) an angle detector into which are input the output of angle sensors that located along the Y-axis and Z-axis of the anvil-assembly-attitude control mechanism and the output of angle sensors located along the Y0-axis and Z0-axis from the anvil-assembly-side transmitter/receiver, and that detects their respective angle data and (b) a command-calculation unit that calculates respective desired rotation angles of the second frame and the anvil shaft based on the angle data from the angle detector, and (2) that generates, based on the desired rotation angles, angle-command values of the second frame and the anvil shaft; and a drive-control unit that has a Y-axis controller and Z-axis controller that, based on the angle-command values from the angle-command generator, individually servo-control the Y-axis servomotor and Z-axis servomotor, respectively;

and wherein there is provided an anvil-shaft target angle that substantially corresponds to the angle data of the head assembly when the rear end of the trocar is set as a reference point (a temporary fixed point) under the condition that the anvil assembly is pulled by the thin wire guide so as to contact the inside of the locked portion of the head assembly or the inside of the front end of the push tube to which the locked portion is connected when the anvil assembly is again being coupled to the head assembly, whereby the attitude of the anvil assembly is automatically controlled.

The invention of Claim 19 is a system according to Claim 17 for use in NOTES, and further including an anvil-assembly-attitude control mechanism that comprises:

a head-assembly-side transmitter/receiver that is provided inside the head assembly and that wirelessly transmits the output of angle sensors that are located along the two axes (Y0-axis and Z0-axis) and that meet at right angles with the main axis (X0-axis) of the head assembly;

an anvil-assembly-side transmitter/receiver that receives from the head-assembly-side transmitter/receiver the output of angle sensors located along the Y0-axis and Z0-axis;

an angle detector into which are input the output of angle sensors located along the Y-axis and Z-axis of the anvil-assembly-attitude control mechanism and the output of angle sensors located along the Y0-axis and Z0-axis from the anvil-assembly-side transmitter/receiver, and that detects the respective angle data;

an angle-command generator that has a command-calculation unit that, based on the angle data from the angle detector, calculates the respective desired rotation angles of the second frame and the anvil shaft, and that generates angle-command values of the second frame and the anvil shaft based on the desired rotation angles; and a drive-control unit that has a Y-axis controller and Z-axis controller that individually servo-control the Y-axis servomotor and Z-axis servomotor, respectively, based on the angle-command values from the angle-command generator;

and wherein there is provided an anvil-shaft target angle that substantially corresponds to the angle data of the head assembly when the trocar-like acute part of the anvil-assembly connecting aid is set as a reference point (a temporary fixed point) under the condition that the insertion body to be inserted into the hollow organ and the push tube via which the anvil-assembly connecting aid is inserted, both of which are located on the side of the head assembly, are pushed and advanced so as to permit the trocar-like acute part to contact the inside of the acute-portion coupling hole while the anvil assembly is being coupled to the head assembly again, whereby the attitude of the anvil assembly is automatically controlled.

The invention of Claim 20 is a system according to any of the preceding claims for use in NOTES, and wherein there is provided an wireless endoscope device or capsule endoscope device, with the front-end assembly of the endoscope arranged in the vicinity of the front end of the head assembly.

The invention of Claim 21 is a system according to any of the preceding claims for use in NOTES, and wherein there is further provided (1) an anvil-assembly connecting aid that consists of a long, flexible, hollow shaft whose two ends are open and via which the rear end of the anvil shaft and the trocar can be inserted, and (2) a holding part that is provided at the rear end of the hollow shaft and that is inserted into the hollow organ under the condition that the rear end of the anvil shaft and the trocar are inserted into the front end of the hollow shaft so that the anvil assembly is coupled to the anvil-assembly connecting aid.

The invention of Claim 22 is a system for use in NOTES, and including a linear stapler that comprises:

(1) an insertion body to be inserted into a body via an endoscopic hole so that endoscopic instruments can be inserted into said body, with said insertion body including (a) an end effector that has one or more linear rows of suture staples that are positioned opposite to one jaw of said end effector, which opens and closes, linearly stapling straight in the transverse direction outside of the hollow organ a specified section of the hollow organ, with the other jaw of said end effector provided with a pair of linear cutters for cutting off straight in the transverse direction a specified section of a hollow organ, with said cutters respectively able to move back and forth from the respective sides of the front end and rear end of the other jaw to an intermediate area of said jaw, and (b) a long, flexible support shaft that is connected to the end effector; and (2) an operating assembly that controls the driving of the linear rows of suture staples and the linear cutters;

and wherein the circular anastomosis surgical stapler includes (a) an anvil assembly that has an anvil shaft on which a trocar protrudes rearward along the main axis (X-axis) at the rear end of the anvil assembly so that the anvil assembly is used as the front end of the circular anastomosis surgical stapler;

(b) an insertion body, positioned opposite to the anvil assembly and including a head assembly that has [1] a circular cutter (annular blade) for cutting off, in the cylindrical direction, a specified section of a hollow (tubular) organ, and [2] one or more annular rows of anastomotic staples for use in circular anastomosis of the two cut-end sections of the remainder of the hollow organ, and a long, flexible support shaft that is connected to the head assembly;

(c) an operating assembly that is connected to the insertion body and that controls driving of the circular cutter (annular blade) and the anastomotic staples;

(d) a coupling (engaging) mechanism that includes a locked portion and a locking portion that are engageable with each other, with the locked portion provided at the anvil shaft and the locking portion provided at the central (main) axis of the head assembly, and that releasably mounts the anvil assembly to the head assembly, and (e) an insertion body, to which the anvil assembly is connected, which is inserted into the hollow organ that has a diseased or defective site, via a natural orifice of the body under the condition that the anvil assembly is detached from the head assembly and temporarily remains near the front end of the diseased or defective site, and the head-assembly-side insertion body retracts to near the rear end of the diseased or defective site, so as to create a space between the anvil assembly and the head assembly;

after said space has been created between the anvil assembly and the head assembly, the linear stapler is inserted into the body via an endoscopic hole to near the diseased or defective site of the hollow organ, and the front-end and rear-end sections of the diseased or defective site are successively cut off straight in the transverse direction and removed from the remainder of the hollow organ by using a pair of linear cutters, and at the same time the two cut-end sections of the remainder of the hollow organ are closed by purse-string-like linear-stapling suturing straight in the transverse direction by a procedure outside of the hollow organ using the linear stapler.

The invention of Claim 23 is a system according to Claim 22 for use in NOTES, and wherein the pair of linear cutters of the end effector move back and forth in the direction opposite to each other due to the linear-staple/cutter-driving mechanism provided inside the other jaw.

The invention of Claim 24 is a system according to Claim 23 for use in NOTES, and wherein the linear-staple/cutter-driving mechanism includes a linear staple/cutter driver shaft that (1) is rotatably provided inside a channel dug facing the rear of the staple cartridge in which one or more linear rows of suture staples are accommodated, (2) is removably fit inside the jaw (unmovable jaw) facing the one jaw (opening/closing jaw), and (3) has a male screw on which reverse screws in the right and left directions are formed on either the anterior half and or the posterior half of the male screw; and front-end and rear-end staple-driving mechanisms, both of which (1) have a wedge mechanism that is threadedly engaged with the respective left and right reverse screws of the linear-staple/cutter-driving mechanism, and (2) move back and forth in the direction opposite to each other inside the channel accompanying the reversible rotation of the linear staple/cutter driver shaft, so as to drive the one or more linear rows of suture staples; and wherein the pair of linear cutters are mounted on the respective front-end and rear-end staple-driving mechanisms in such a way that the pair of linear cutters are driven (disposed) so that the blade edges thereof are positioned opposite to each other and standing in the direction of the staple cartridge.

The invention of Claim 25 is a method for use in NOTES, and includes a circular anastomosis surgical stapler that comprises an anvil assembly that has an anvil shaft on which a trocar is protrudes rearward along the main axis (X-axis) at the rear end of the anvil assembly so that the anvil assembly is used as the front end of the circular anastomosis surgical stapler;

an insertion body that is positioned opposite to the anvil assembly and that includes a head assembly that has (1) a circular cutter (annular blade) for cutting off in the cylindrical direction a specified section of a hollow (tubular) organ, (2) one or more annular rows of anastomotic staples for use in circular anastomosis of the two cut-end sections of the remainder of the hollow organ, and (3) a long, flexible support shaft that is connected to the head assembly;

an operating assembly that is connected to the insertion body and that controls the driving of the circular cutter (annular blade) and the anastomotic staples;

a thin guide wire that is inserted via the insertion body and connected to the acute (rear) end of the trocar so as to be capable of being taken up by a take-up unit and released; and a coupling (engaging) mechanism that includes a locked portion and a locking portion that are engageable with each other, with the locked portion provided at the anvil shaft and the locking portion provided at the main axis of the head assembly, and that releasably mounts the anvil assembly to the head assembly;

with said method including the following steps:
(a) inserting the insertion body, to which the anvil assembly is connected, via a natural orifice of the body and into the hollow organ that has a diseased or defective site;
(b) detaching the anvil assembly from the head assembly and leaving the anvil assembly near the front end of the diseased or defective site of the hollow organ;
(c) retracting the head-assembly-side insertion body to near rear end of the diseased or defective site, so as to create a space between the anvil assembly and the head assembly;
(d) after said space has been created between the anvil assembly and the head assembly, inserting—into the body, via an endoscopic hole to near the diseased or defective site of the hollow organ—(1) a linear stapler that has one or more linear cutters that cut off straight in the transverse direction a specified section of the hollow organ, and (2) one or more linear rows of suture staples that are used to staple straight in the transverse direction the respective cut-end sections of the remainder of the hollow organ;
(e) cutting off the respective cut-end sections of the diseased or defective site of the hollow organ and removing the diseased or defective site from the remainder of the hollow organ;
(f) closing the respective cut-end sections of the remainder of the hollow organ by purse-string-like linear-stapling suturing straight in the transverse direction by a procedure outside of the hollow organ using the linear stapler;
(g) again coupling the anvil assembly to the head assembly;
(h) performing circular anastomosis of the two cut-end sections of the remainder of the hollow organ; and, at the same time,
(i) cutting off the cut-end sections that have been closed by purse-string-like suturing of the remainder of the hollow organ by a procedure inside the hollow organ, so that the sections are again interconnected.

The invention of Claim 26 is a method for use in NOTES, using a circular anastomosis surgical stapler that comprises:

an anvil assembly to whose rear end is connected an anvil shaft whose rear end connects releasably an acute part that includes a trocar, so that said anvil shaft protrudes rearward along the main axis (X-axis) so that the anvil assembly is used as the front end of the circular anastomosis surgical stapler;

an insertion body that is positioned opposite to the anvil assembly and that includes (1) a head assembly that has a circular cutter (annular blade) for cutting off in the cylindrical direction a specified section of a hollow organ, and (2) one or more annular rows of anastomotic staples for use in circular anastomosis of the two cut-end sections of the remainder of the hollow organ, and (3) a long, flexible support shaft that is connected to the head assembly;

an operating assembly that is connected to the insertion body and that controls the driving of the circular cutter and the anastomotic staples;

a thin guide wire inserted via the insertion body and that is connected to the acute (rear) end of the trocar so as to be capable of being taken up and released;

with said circular anastomosis surgical stapler provided with a coupling (engaging) mechanism that includes a locked portion and a locking portion that are engageable with each other, with the locked portion provided at the anvil shaft and the locking portion provided at the main axis of the head assembly, and that releasably mounts the anvil assembly to the head assembly;

with said method comprising the following steps:
(a) inserting the insertion body, to which the anvil assembly is connected, via a natural orifice of the body and into the hollow organ that has a diseased or defective site;
(b) detaching the anvil assembly from the head assembly and temporarily leaving the anvil assembly near the front end of the diseased or defective site of the hollow organ;
(c) retracting the head-assembly-side insertion body to near the rear end of the diseased or defective site, so as to create a space between the anvil assembly and the head assembly;
(d) after said space has been created between the anvil assembly and the head assembly, inserting—into the body, via an endoscopic hole to near the diseased or defective site of the hollow organ—a linear stapler that has [1] one or more linear cutters that cut off straight in the transverse direction a specified section of a hollow organ, and [2] one or more linear rows of suture staples that are used to staple straight in the transverse direction the respective cut-end sections of the remainder of the hollow organ;
(e) cutting off the respective front-end and rear-end sections of the diseased or defective site of the hollow organ and removing the diseased or defective site from the remainder of the hollow organ; and at the same time,
(f) closing the two cut-end sections of the remainder of the hollow organ by purse-string-like linear-stapling suturing straight in the transverse direction by a procedure outside of the hollow organ using the linear stapler;
(g) again coupling the anvil assembly to the head assembly;
(h) performing circular anastomosis of the two cut-end sections of the remainder of the hollow organ; and, at the same time,
(i) cutting off the two cut-end sections that have been closed by purse-string-like linear-stapling suturing of the remainder of the hollow organ by a procedure inside the hollow organ, so that the sections are again interconnected.

The invention of Claim 27 is a method for use in NOTES, using a circular anastomosis surgical stapler that comprises:

an anvil assembly to whose rear end is connected an anvil shaft whose rear end connects releasably to an acute part that includes a trocar, so that said anvil shaft protrudes rearward along the main axis (X-axis) so that the anvil assembly is used as the front end of the circular anastomosis surgical stapler;

an insertion body that is positioned opposite to the anvil assembly and that includes
(1) a head assembly that has (a) a circular cutter (annular blade) for cutting off in the cylindrical direction a specified section of a hollow organ, and (b) one or more annular rows of anastomotic staples for performing circular anastomosis of the two cut-end sections of the remainder of the hollow organ, and
(2) a long, flexible support shaft that is connected to the head assembly;

an operating assembly that is connected to the insertion body and that controls the driving of the circular cutter (annular blade) and the anastomotic staples;

a thin guide wire that is inserted via the insertion body and connected to the acute (rear) end of the trocar so as to be capable of being taken up and released;

a coupling (engaging) mechanism that includes a locked portion and a locking portion that are engageable with each other, with the locked portion provided at the anvil shaft and the locking portion provided at the central (main) axis of the head assembly, and that releasably mounts the anvil assembly to the head assembly; and an anvil-assembly connecting aid that (1) consists of (a) a long, flexible, hollow shaft whose two ends are open and via which the rear end and the acute part of the anvil shaft can be inserted, and (b) a holding part provided at the rear end of the hollow shaft, and (2) is inserted into the hollow organ under the condition that the rear end and the acute part of the anvil shaft are inserted into the front end of the hollow shaft so that the anvil assembly is coupled to the anvil-assembly connecting aid, with said method comprising the following steps:
(a) inserting—via a natural orifice of the body and into the hollow organ that has a diseased or defective site—the anvil-assembly insertion aid, to the front of which said anvil assembly is coupled;
(b) retracting the anvil-assembly insertion aid and detaching the anvil assembly, at which the acute part of the anvil shaft is connected to the thin wire guide, from the anvil-assembly insertion aid and, temporarily leaving the anvil assembly near the front end of the diseased or defective site, with the anvil-assembly insertion aid retracting to near the rear end of the diseased or defective site, so that a space between the anvil assembly and the anvil-assembly insertion aid is created;
(c) inserting—into the body, via an endoscopic hole to near the diseased or defective site of the hollow organ—a linear cutting/stapling device that has (1) a pair of linear cutters that cut off straight in the transverse direction a specified section of a hollow organ, and (2) one or more linear rows of staples that staple straight in the transverse direction the respective cut-end sections of the remainder of the hollow organ;
(d) by a procedure outside of the hollow organ, cutting off the respective front-end and rear-end sections of the diseased or defective site of the hollow organ and removing the diseased or defective site from the remainder of the hollow organ; and, at the same time,
(e) closing the respective cut ends of the remainder of the hollow organ by purse-string-like linear-stapling suturing straight in the transverse direction;
(f) removing the anvil-assembly insertion aid from the natural orifice, and inserting—via the natural orifice into the hollow organ that has the diseased or defective site— the head-assembly-side insertion body;
(g) again coupling the anvil assembly to the head assembly;
(h) performing circular anastomosis of the two cut-end sections of the remainder of the hollow organ by a procedure inside the hollow organ; and, at the same time,
(i) cutting off the two cut-end sections that have been closed by purse-string-like linear-stapling suturing of the remainder of the hollow organ, so that the sections are again interconnected.

The invention of Claim 28 is a method according to any of Claims 25–27 for use in NOTES, with said method using an anvil-assembly-attitude control mechanism that is inside the anvil assembly and connected to the anvil shaft, and that automatically controls the attitude of the anvil assembly in relation to the anvil shaft so that the main axis of the anvil shaft substantially corresponds to the main axis of the head assembly (X0-axis) when the anvil assembly is again coupled to the head assembly after the anvil assembly is removed from the head assembly.

The invention of Claim 29 is a method according to Claim 28 for use in NOTES, using an anvil-assembly attitude-control system that includes:
(1) an anvil-assembly-attitude control mechanism that has a biaxial oscillating mechanism provided with a Y-axis drive means and a Z-axis drive means that respectively oscillate along the two axes (Y-axis and Z-axis) and meet at right angles with the main axis (X-axis) of the anvil shaft;
(2) a head-assembly-side transmitter/receiver that is inside the head assembly and that wirelessly transmits the output of angle sensors located along the two axes (Y0-axis and Z0-axis) that meet at right angles with the main axis (X0-axis) of the head assembly;
(3) an anvil-assembly-side transmitter/receiver that receives from the head-assembly-side transmitter/receiver the output of angle sensors located along the Y0-axis and Z0-axis;
(4) an angle detector into which are input the output of angle sensors located along the X-axis and Y-axis of the anvil-assembly-attitude control mechanism and the output of angle sensors located along the Y0-axis and Z0-axis from the anvil-assembly-side transmitter/receiver, and which detects the angle data that have been input;
(5) an angle-command generator that has a command-calculation unit that, based on the angle data from the angle detector, calculates the respective desired rotation angles of the Y-axis drive means and the Z-axis drive means; and
(6) a drive-control unit that has a Y-axis controller and a Z-axis controller individually servo-control a Y-axis servomotor and Z-axis servomotor, respectively, based on the angle-command values generated by the angle-command generator;

with said method comprising the following steps:
(a) when the anvil assembly is being coupled again to the head assembly, pulling the anvil assembly by the thin wire guide so as to contact the inside of the locked portion of the head assembly or the inside of the front end of the push tube to which the locked portion is connected;
(b) providing anvil-shaft target angle that substantially corresponds to the angle data of the head assembly when the trocar-like acute part of the anvil-assembly connecting aid is set as a reference point; and
(c) automatically controlling the attitude of the anvil assembly.

The invention of Claim 30 is a method according to Claim 28, for use in NOTES, using an anvil-assembly attitude-control system that includes
(1) a anvil-assembly-attitude control mechanism that has a biaxial oscillating mechanism that includes a Y-axis drive means and a Z-axis drive means that oscillate along the two axes (Y-axis and Z-axis, respectively) and meet at right angles with the central axis (X-axis) of the anvil shaft;
(2) a head-assembly-side transmitter/receiver that is provided inside the head assembly and that wirelessly transmits the output of angle sensors located along the two axes (Y0-axis and Z0-axis) that meet at right angles with the central axis (X0-axis) of the head assembly;
(3) an anvil-assembly-side transmitter/receiver that receives from the head-assembly-side transmitter/receiver the output of angle sensors located along the two axes (Y0-axis and Z0-axis);
(4) an angle detector into which are input the output of angle sensors located along the X-axis and Y-axis of the anvil-assembly-attitude control mechanism and the output of angle sensors located along the Y0-axis and Z0-axis from the anvil-assembly-side transmitter/receiver, and which detects said angle data;

(5) an angle-command generator that has a command-calculation unit that calculates the respective desired rotation angles of the Y-axis drive means and Z-axis drive means based on the angle data from the angle detector; and (6) a drive-control unit that has a Y-axis controller and Z-axis controller that individually servo-control a Y-axis servomotor and a Z-axis servomotor, respectively, based on the angle-command values generated by the angle-command generator;

with said method comprising the following steps:
(a) allowing the insertion body to be inserted into the hollow organ and the push tube via which the anvil-assembly connecting aid is inserted, with both located on the side of the head assembly that is to be pushed and advanced;
(b) allowing the trocar-like acute part to contact the inside of the acute-part coupling hole while the anvil assembly is being coupled again to the head assembly;
(c) providing an anvil-shaft target angle that corresponds to the angle data of the head assembly when the trocar-like acute part of the anvil-assembly connecting aid is set as a reference point;
(d) automatically controlling the attitude of the anvil assembly.

The invention of Claim 31 is a method for use in NOTES, using a linear cutting/stapling device that includes (1) an insertion body to be inserted into a body via an endoscopic hole that is opened on so that endoscopic instruments can be inserted into said body, with said insertion body including:
(a) an end effector that has one or more linear rows of suture staples that are positioned opposite to any one of a pair of jaws, which opens and closes and staples straight in the transverse direction the remainder of the hollow organ by a procedure outside of the hollow organ, with the other (unmovable jaw) jaw provided with a pair of linear cutters for cutting off straight in the transverse direction a specified section of the hollow organ, with said linear cutters able to move back and forth from the front end and rear ends of said other jaw (unmovable jaw) to an intermediate section of said other jaw (unmovable jaw); and
(b) a long, flexible support shaft that is connected to the end effector; and (2) an operating assembly that controls the driving of the linear cutters and the one or more linear rows of suture staples;

with said method comprising the following steps:
(a) inserting—via a natural orifice of the body and into the hollow organ that has a diseased or defective site—a circular anastomosis surgical stapler that comprises:
[1] an anvil assembly that has an anvil shaft on which a trocar protrudes rearward along the main axis (X-axis) at the rear end of the anvil assembly so that the anvil assembly is used as the front end of the circular anastomosis surgical stapler;
[2] an insertion body that is positioned opposite to the anvil assembly and that includes [a] a head assembly that has {1} a circular cutter for cutting off in the cylindrical direction a specified section of a hollow organ, and {2} one or more annular rows of anastomotic staples for use in circular anastomosis of the two cut-end sections of the remainder of the hollow organ, and [b] a long, flexible support shaft that is connected to the head assembly;
[3] an operating assembly that is connected to the insertion body and that controls the driving of the circular cutter (annular blade) and the anastomotic staples;
[4] a coupling (engaging) mechanism that includes a locked portion and a locking part that are engageable with each other, with the locked portion provided at the anvil shaft and the locking part provided at the main axis of the head assembly, and that releasably mounts the anvil assembly to the head assembly; and
[5] an insertion body to which the anvil assembly is connected;
(b) detaching the anvil assembly from the head assembly and temporarily leaving the anvil assembly near the front end of the diseased or defective site of the hollow organ, and temporarily leaving the head assembly near the rear end of the diseased or defective site, so as to create a space between the anvil assembly and the insertion body;
(c) inserting the linear cutting/stapling device into the body via an endoscopic hole to near the diseased or defective site of the hollow organ;
(d) using the pair of linear cutters outside of the hollow organ to cut off straight in the transverse direction the respective front-end and rear-end sections of the diseased or defective site of the hollow organ; and, at the same time,
(e) closing the respective cut-end sections of the remainder of the hollow organ by purse-string-like linear-stapling suturing straight in the transverse direction by a procedure outside of the hollow organ using the one or more linear rows of staplers.

Effects of the Invention

Claims 1, 2, 25, and Claim 26 of the present invention disclose the following: an insertion body of a circular anastomosis surgical staplers is inserted via a natural orifice of the body into a hollow organ that has a diseased or defective site, and the anvil assembly is detached from the head assembly and temporarily remains near the front-end section of the diseased or defective site of the hollow organ, and the head-assembly-side insertion body retracts to near the rear end of the diseased or defective site, so as to create a space between the anvil assembly and the insertion body. Under this condition, a linear-stapling/cutting device is inserted into the body via an endoscopic hole to near the diseased or defective site of the hollow organ. While said site is observed via another endoscope, the diseased or defective site is cut off and removed from the remainder of the hollow organ, and at the same time the two cut-end sections of the remainder of the hollow organ are closed by purse-string-like linear-stapling suturing straight in the transverse direction by a procedure outside of the hollow organ, after which the circular anastomosis surgical staplers automatically or semiautomatically perform circular anastomosis of the two cut-end sections of the remainder of the hollow organ by a procedure inside the hollow organ. Therefore, by eliminating the need for a large-scale abdominal incision and also reducing the operating time and invasiveness of the surgical procedure, this system and method for use in NOTES is improved in terms of operability of surgical devices, the reliability of the operation, and economic efficiency.

According to the invention of Claim 3, in addition to having effects similar to those of Claim 1, all of the drive units, such as a push-tube drive mechanism to couple and decouple the anvil assembly to the head assembly, a staple/cutter driving mechanism, and a take-up unit for taking up the thin wire guide, are accommodated in a connection portion between the head assembly and the support shaft, and the operation of all the drive units is performed by remote-control via the operating assembly. It is therefore possible to eliminate all of the drive units traditionally provided in an operating assembly and in the connection members for drive units, such as connecting pipes connected to the head assembly via the inside of the support shaft, the push tube and driver tube, and hence the structure of the operating assembly and support shaft is simplified considerably, and it is possible to provide for use in NOTES a system and method that are further improved in regard to the operability and economic efficiency of surgical devices.

According to the invention of Claim 4, in addition to having effects similar to those of Claim 3, a wireless receiver and battery are provided near the connection portion between the head assembly and the support shaft, and control of the push-tube driving mechanism, the staple/cutter driving mechanism, and the take-up unit is effected remotely and wirelessly. As a result, it is possible to eliminate the electric control wires traditionally connected to the head assembly via the inside of the support shaft, and hence the structures of the operating assembly and support shaft are simplified considerably, making it possible to provide a system and method that further improve the operability and economic efficiency of the surgical devices for use in NOTES.

According to the invention of Claim 5, in addition to having effects similar to those of Claims 1-4, when the anvil assembly is reconnected to the head assembly after the diseased or defective site has been cut off and removed from the remainder of the hollow organ, the back-and-forth movement of the lock-adjusting pipe opens and closes the split-capture part located at the front end of the push tube together with the forward moving of the split-capture part, then captures the locked part of the anvil shaft and rolls back the push tube, so that the anvil assembly is pulled toward the head-assembly side, and at the same time the anvil assembly can be easily locked to the head assembly. Hence, the reliability of the coupling mechanism between the anvil assembly and the head assembly is improved.

According to the invention of Claim 6, in addition to having effects similar to those of Claims 1, 2, and 5, the push-tube drive mechanism, the lock-adjustment-tube drive mechanism, and the stable/cutter drive are accommodated near the connection portion between the head assembly and the support shaft, and control of those mechanisms is remotely performed via the operating assembly. As a result, it is possible to eliminate all of those drive units' connecting members traditionally provided in the operating assembly, such as the push tube, lock-adjustment tube, and driver tube to drive the staple/cutter, and hence the structures of the operating assembly and support shaft are simplified considerably, and it is possible to provide a system and method that further improve the operability and economic efficiency of the surgical devices for use in NOTES.

According to the invention of Claim 7, in addition to having effects similar to those of Claim 6, a wireless receiver and a battery are further equipped near the connection portion between the head assembly and the support shaft, and the control of the push-tube drive mechanism, the lock-adjustment-tube drive mechanism, the staple/cutter driving mechanism, and the take-up unit is performed remotely and wirelessly. As a result, it is possible to eliminate the electric control wire that traditionally passes via the inside of the supporting shaft and connects the operation assembly and head assembly. Thus, the structure of the operating assembly and support shaft are simplified considerably, and it is also possible to provide a system and method that further improve the operability and economic efficiency of the surgical devices for use in NOTES.

According to the invention of Claim 8, in addition to having effects similar to those of Claim 1 or Claim 2, the purse-string-like linear-stapling suturing sites of the two portions of the remainder of the hollow organ on the anvil-assembly side and the head-assembly side, respectively, are cauterized successively by galvanization by monopolar electricity to the monopolar electrode via the rolled-up electric guide wire, so that the anvil shaft can easily penetrate purse-string-like linear-stapling suturing sites, and the contacting, reconnection, and locking of the anvil assembly to the head assembly becomes easy, and there is no need to connect the anvil assembly to the head assembly by a human hand from outside the site of the incision opening of the abdomen, as used to be done in previous procedures. Therefore, by eliminating the need for a large-scale abdominal incision and by reducing the operating time and invasiveness of surgical procedures, it is possible to provide a system and method that are sure to further improved the operability, reliability of operation, and economic efficiency of the surgical devices for use in NOTES.

According to the invention of Claim 9, in addition to having effects similar to those of Claim 8, the monopolar electrode exposes only a small area and is buried on the outer circumference at the rear end of the trocar, so that, by galvanization of monopolar electricity to the monopolar electrode, there is the effect of increasing the efficiency of cauterization of the purse-string-like linear-stapling suturing sites of the two portions of the remainder of the hollow organ.

According to the invention of Claim 10, in addition to having effects similar to those of Claim 8 or Claim 9, the monopolar electrode is exposed to an appropriate length in the axial direction on the outer circumference at the rear end of the trocar, so that cauterization of the purse-string-like linear-stapling suturing sites of the two portions of the remainder of the hollow organ is done by sequential movements in the axial direction via monopolar electrical galvanization to the monopolar electrode, which has the effect of further increasing the efficiency of cauterization.

According to the invention of Claim 11, in addition to having effects similar to those of Claim 8 or Claim 9, the anvil shaft that is connected to the trocar rotates when the monopolar electrode is galvanized by monopolar electricity, so as to prevent the burning out of the purse-string-like linear-stapling suturing sites of the two portions of the remainder of the hollow organ that could result from galvanization of monopolar electricity, which has the effect of further increasing the efficiency of cauterization.

According to the invention of Claim 12, in addition to having effects similar to those of Claims 8-11, when the monopolar electrode is galvanized by monopolar electricity via the electric guide wire (thin wire guide), the acute part of the anvil shaft is able to easily penetrate both of the purse-sting-like linear-stapling suturing sites of the two portions of the remainder of the hollow organ on the anvil-assembly side and the head-assembly side, which sites are cauterized successively and pulled to the head-assembly side. After the acute part is withdrawn from the rear end of the operating assembly, it is easy to reconnect and lock the anvil assembly to the head assembly, and hence there is no need to connect the anvil assembly to the head assembly by human hand from the outside of the abdomen-opening incision site, as used to be done in previous procedures. Therefore by eliminating the existing need for a large-scale abdominal incision and by reducing the operating time and invasiveness of surgical procedures, it is possible to provide a system and method that are sure to further improve the operability, reliability, and economic efficiency of the surgical devices and their operation for use in NOTES.

According to the invention of Claim 13, in addition to having effects similar to those of Claim 2 or Claim 12, and under the condition such that the anvil assembly is separated from the head assembly, the diseased or defective site of the hollow organ is cut off and removed from the remainder of the hollow organ and the two cut-end sections of the remainder of the hollow organ are closed by purse-string-like linear-stapling suturing. After the acute part is withdrawn from the rear end of the operating assembly and the anvil assembly is reconnected to the head assembly, it is possible to easily insert the trocar-like acute part of the anvil connection aid into the acute-part coupling hole of read end of the anvil shaft, and thus improve the operability and reliability of the reconnect/lock procedure.

According to the inventions of Claim 14 and Claim 28, in addition to having effects similar to those of Claims 1-13 and Claims 25-27, the anvil assembly is equipped with an anvil-assembly-attitude control mechanism that automatically controls the gradient attitude relating to the anvil shaft so that the central (main) axis of the anvil shaft substantially corresponds to the central (main) axis of the head assembly, which makes it is easy to reconnect the anvil assembly to the head assembly after being separated therefrom. As a result, there is no need to connect the anvil assembly to the head assembly by human hand from outside the site of incision opening of the abdomen as used to be done in previous procedures. This eliminates the need for a large-scale abdominal incision, and reduces the operating time and invasiveness of surgical procedures, making it possible to provide a system and method that are sure to further improve the operability of the surgical devices and the reliability and economic efficiency of operations for use in NOTES.

According to the invention of Claim 15, in addition to having effects similar to those of Claim 14, the anvil-assembly-attitude control mechanism includes (1) a biaxial oscillating mechanism that can oscillate along the two axes (Y-axis and Z-axis) that intersect orthogonally with the anvil main axis (X-axis), (2) angle sensors for the Y-axis and Z-axis, and (3) a drive means for driving the biaxial oscillating mechanism along the Y-axis and Z-axis, which has the effect of automatically and stably controlling the gradient attitude relating to the anvil shaft so that the central (main) axis of the anvil shaft substantially corresponds to the central (main) axis of the head assembly.

According to the invention of Claim 16, in addition to having effects similar to those of Claim 15, the biaxial oscillating mechanism consists of a gimbal mechanism in which a second frame body that is able to oscillate along the Y-axis is installed in the first frame body, which is fixed inside the anvil assembly, and an anvil-shaft support that is able to oscillate along the Z-axis and to support the anvil shaft is installed in the second frame body, which has the effect of saving space and providing high reliability and stableness of anvil-shaft-attitude control procedures.

According to the invention of Claim 17, in addition to having effects similar to those of Claim 15 or Claim 16, the drive means are two servomotors that control the drive of the biaxial oscillating mechanism along the Y-axis and Z-axis, respectively, which has the effect of controlling the anvil-shaft attitude with high accuracy and high speed.

According to the inventions of Claim 18 and Claim 29, in addition to having effects similar to those of Claims 11-14, Claim 18, or Claim 28, in the anvil-attitude control system, the anvil assembly is pulled by the thin wire guide and is moved to inside the locking portion of the head assembly, or is moved closer to the push-tube front end in which the locking portion is formed. Under this condition, setting a base point (temporally fixed point) at the read end of the trocar, which meets the front end of the push tube, the anvil-attitude control system automatically controls the attitude of the anvil with reference to the target angle of the anvil shaft, which is roughly set to fit the angle data of the head assembly at that time, which has the effect of ensuring the reliability of the anvil-attitude control system.

According to the inventions of Claim 19 and Claim 30, in addition to having effects similar to those of Claim 17 or Claim 28, in the anvil-attitude control system the push tube and the head assembly are together pushed out forward to meet the acute-part connection hole that is formed rearward of the anvil shaft. Under this condition, setting a base point (temporally fixed point) at the acute part of the anvil-assembly connecting aid, the anvil-attitude control system automatically controls the attitude of the anvil assembly with reference to the target angle of the anvil shaft, which is set to roughly fit the angle data of the head assembly at that time, which has the effect of ensuring the reliability of the anvil-attitude control system.

According to the invention of Claim 20, in addition to having effects similar to those of Claims 1-19, by employing a wireless endoscope or capsule endoscope equipped at the front end of the endoscope near the front of the head assembly in the circular anastomosis surgical stapler, it is possible to monitor the gradient of the anvil shaft when that is separated from the head assembly, which has the effect of enabling reliable circular anastomosis of the two cut-end sections of the remainder of the hollow organ.

According to the inventions of Claim 21 and Claim 27, in addition to having effects similar to those of Claims 1-20, the anvil assembly that is connected at the front end of the anvil-assembly insertion aid is inserted via the natural orifice of the body and into a hollow organ that has a diseased or defective site, and then separated from the anvil-assembly insertion aid and allowed to temporarily remain as it is, so that the anvil assembly and the anvil-assembly insertion aid are temporarily left at the front end and rear end, respectively, of the diseased or defective site of the hollow organ. Under this condition, the linear cutting/stapling device is inserted into the body via an endoscopic hole that is opened so that endoscopic instruments can be inserted into the body, where it cuts off and removes the diseased or defective site from the remainder of the hollow organ. Then, after the respective cut-end sections of the remainder of the hollow organ are closed by purse-string-like linear-stapling suturing straight in the transverse direction by a procedure outside of the hollow organ, the anvil-assembly insertion aid is removed from the natural orifice, after which the anvil assembly is reconnected to the head assembly of the circular anastomosis surgical stapler, which, while within the hollow organ, performs circular anastomosis of the two cut-end sections of the remainder of the hollow organ, and at the same time cuts off the purse-string-like linear-stapling suturing site of the remainder of the hollow organ, which has the effect of enabling the sections to be easily again interconnected.

According to the inventions of Claims 22 and Claim 31, the linear cutting/stapling device that is inserted into the body via an endoscopic hole, quickly cuts off the respective front-end and rear-end sections of the diseased or defective site of the hollow organ by using a pair of linear cutters that move back and forth to and from each other in reverse directions so as to pinch the diseased or defective site from both sides toward the middle portion of the diseased or defective site straight in the transverse direction, and at the same time the linear cutting/ stapling device quickly closes the respective cut-end sections of the remainder of the hollow organ by using the suture staples that are driven so as to pinch, straight in transverse direction, the diseased or defective site, from the two sides toward the middle portion of the diseased or defective site, thereby eliminating the current need for a large-scale abdominal incision and reducing the operating time and invasiveness of the surgical procedure, which has the effect of providing a system and method that are improved in operability of the surgical devices and the reliability and economic efficiency of the operation for use in NOTES.

According to the invention of Claim 23, in addition to having effects similar to those of one of Claim 22, due to the linear staple/cutter driver mechanism being installed inside of the other jaw of the end effector, a pair of linear cutters move back and forth to and from each other in reverse directions, or move so as to pinch the diseased or defective site from the two sides toward the midsection of the diseased or defective site and then quickly cut off the diseased or defective site of the hollow organs straight in the transverse direction, as a result of which the cutting time is reduced to one-half that of the time of an existing device that is equipped with one cutter and that moves only in one direction. Also, it is possible to efficiently cut off the diseased or defective site from the hollow organ in such a way that the thin wire guide of the circular anastomosis surgical staplers temporarily remains in said midsection, thereby keeping stable the cutting function.

According to the invention of Claim 24, in addition to having effects similar to those of the invention of Claim 23, the linear-staple/cutter-driving mechanism has (1) a front-end staple-driving mechanism and a rear-end staple-driving mechanism that are respectively screwed to the male and reverse screws formed on the anterior half and posterior half of the linear staple/cutter driver shaft installed in the other jaw, and that move reciprocally back and forth, and (2) a pair of linear cutters that are vertically installed on the front end and rear-end staple-driving mechanisms, respectively, so that it is possible to make the linear-staple/cutter-driving mechanism simple and compact.

BRIEF DESCRIPTIONS OF THE DRAWINGS

Figure 25:
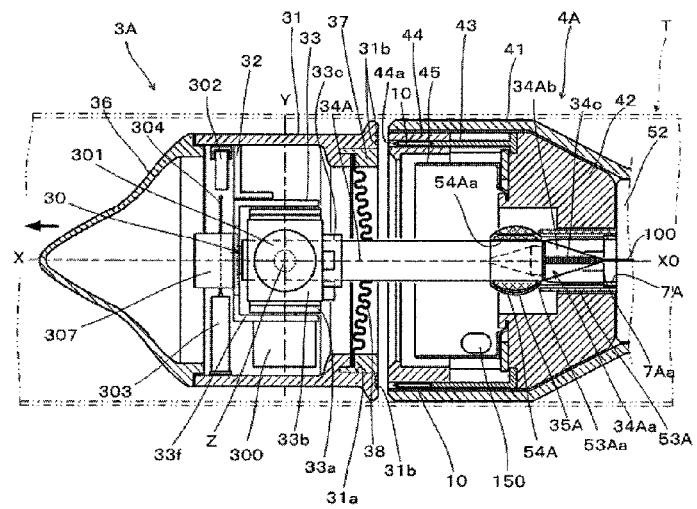
FIG. 25 is a vertical-section diagram of the anvil assembly and the head assembly shown in FIG. 21, coupled with each other and inserted into the hollow organ.
Figure 26:
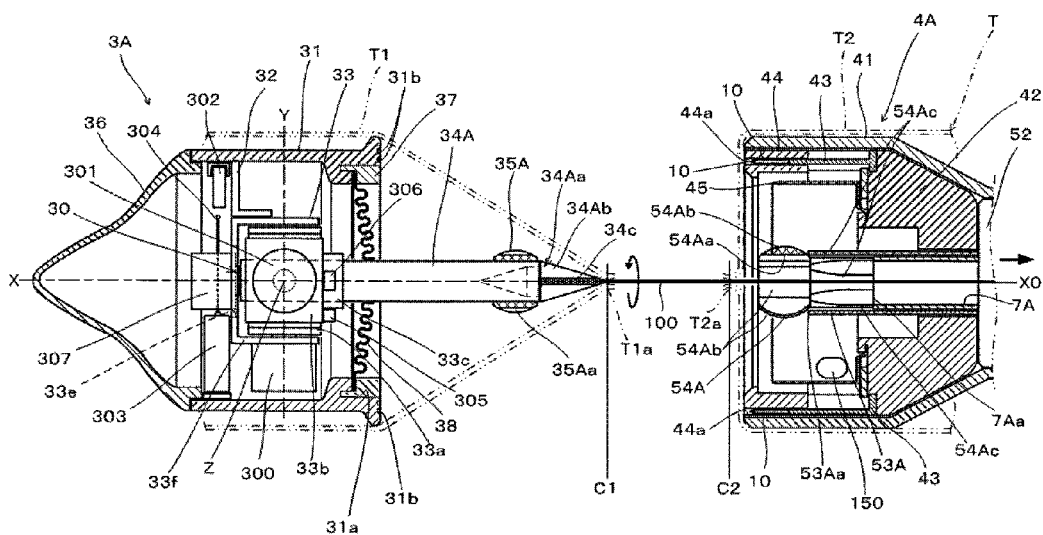

FIG. 26 is a vertical-section diagram of the anvil assembly and the head assembly decoupled from each other, with the diseased or defective site of the hollow organ cut off, and, at the same time, with the two cut-end sections of the remainder of the hollow organ being closed by purse-string-like linear-stapling suturing using the linear cutting/stapling device, continuing the condition shown in FIG. 25.

Figure 27:
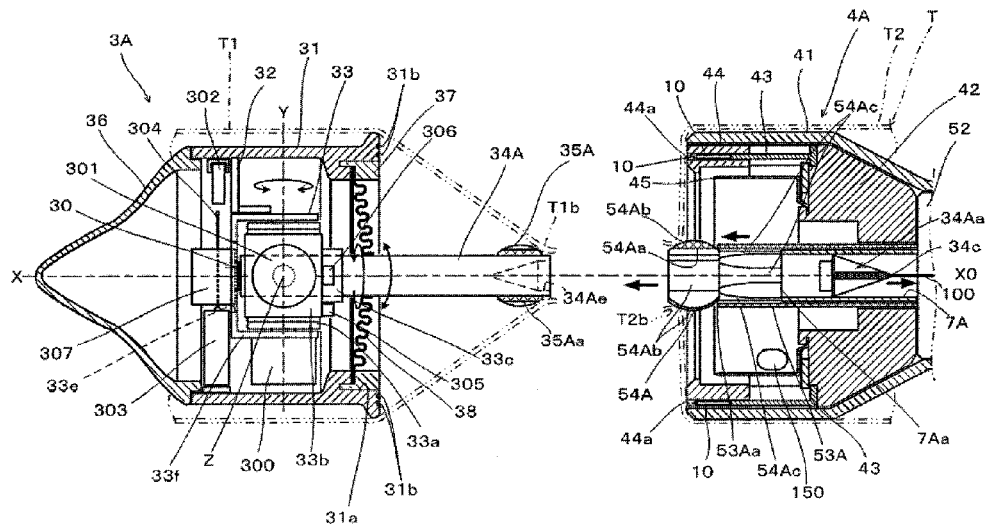

FIG. 27 is a vertical-section diagram showing the acute part whose trocar is being separated from the anvil shaft and pulled by the electric guide wire (galvanized by monopolar electric) and then cauterizing and successively penetrating the two purse-string-like linear-stapling suturing sites of the two portions of the remainder of the hollow organ on the anvil-assembly side and the head-assembly side, and then being pulled further rearward in the head assembly, continuing the condition shown in FIG. 26.

Figure 28:
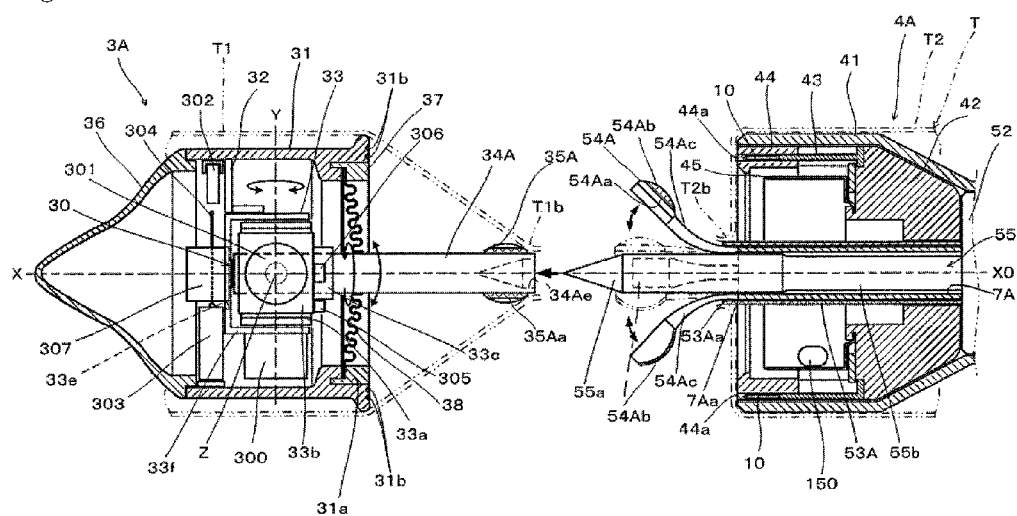

FIG. 28 is a vertical-section diagram showing that the anvil-assembly connection aid that has been inserted into the push tube from the rear end of the operation assembly moves forward together with the locking portion (opened state) and the head assembly and approaches the rear end of the anvil shaft, continuing the condition shown in FIG. 27.

Figure 29:
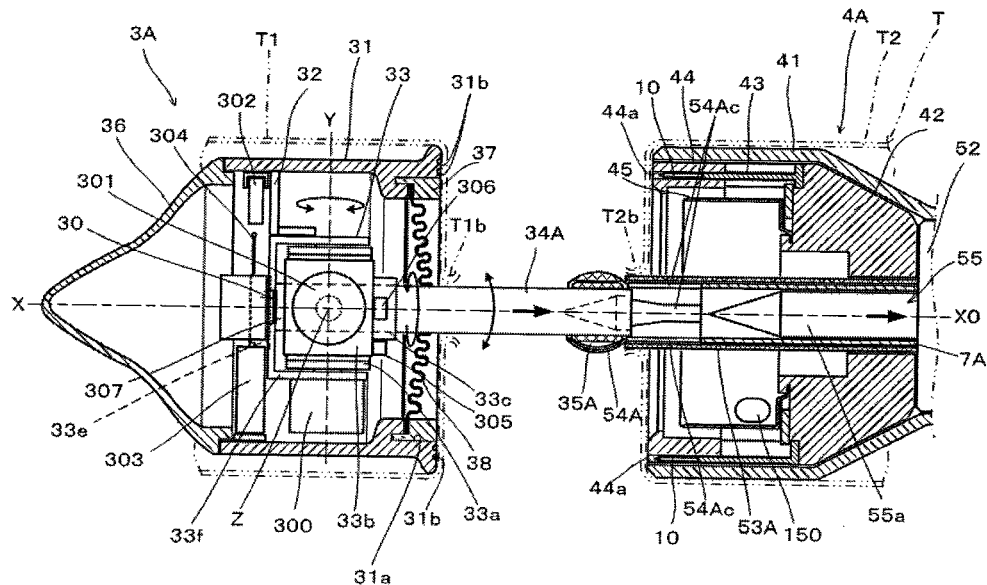

FIG. 29 is a vertical-section diagram showing the anvil-assembly connection aid moving rearward in the push tube while at the same time the lock-adjusting pipe moves forward and the locking portion closes and is coupled with the locked portion of the anvil shaft, continuing the condition shown in FIG. 28.

Figure 30:
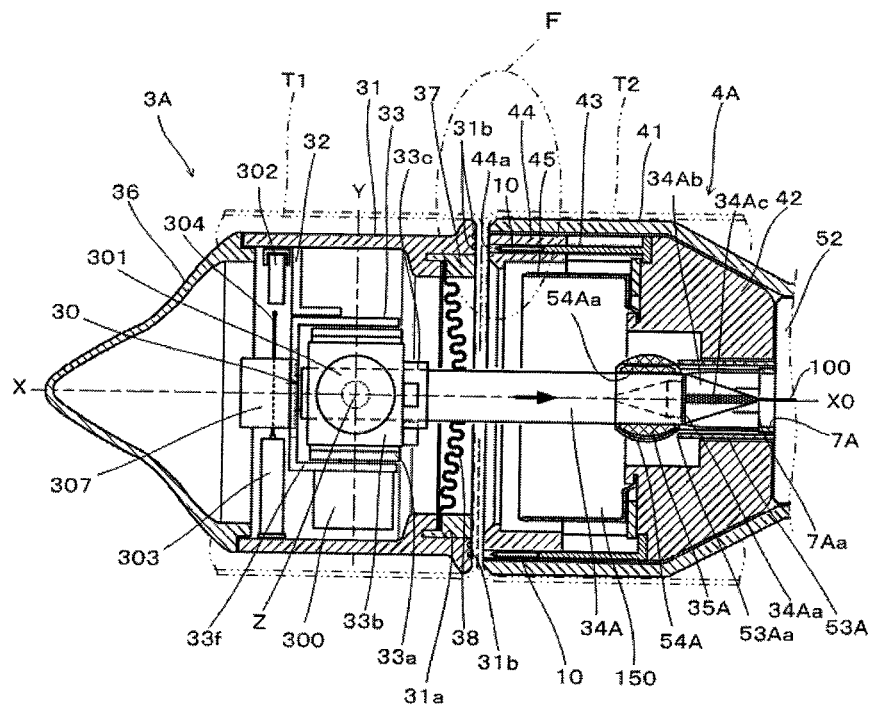

FIG. 30 is a vertical-section diagram showing that forcing the push tube that keeps the anvil shaft coupled with and locked to the anvil assembly to retract, with the anvil assembly being pulled to a specified position of being coupled with the head assembly, continuing the condition shown in FIG. 29.

FIGS. 31(a) and 31(b) are vertical-section diagrams of the circular anastomosis surgical stapler's head assembly and operating assembly, respectively, showing the main configuration concept of the modified mode of Embodiment 2 of the present invention.

Figure 32:
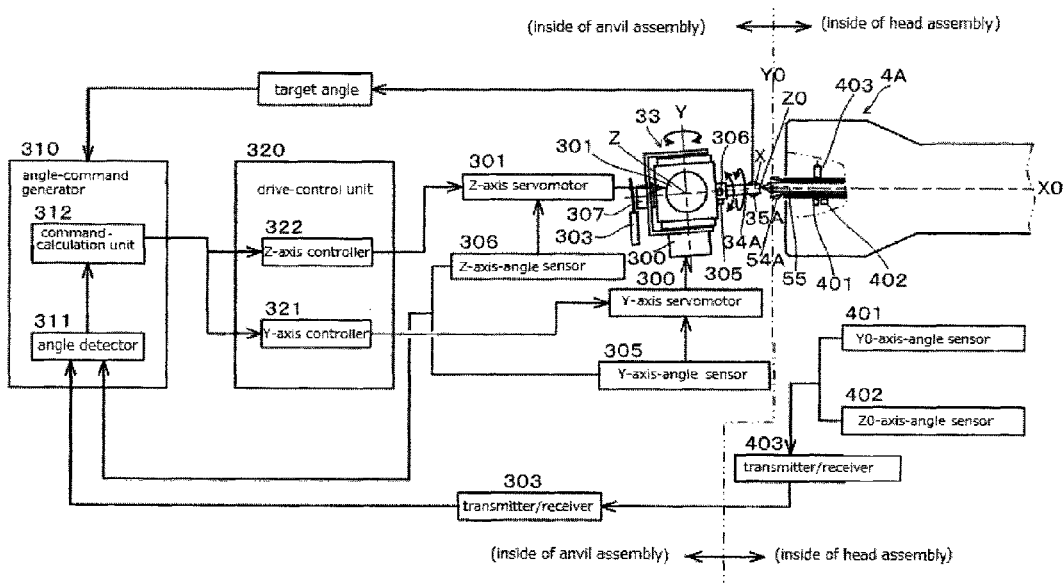

FIG. 32 is a block diagram setting forth the main configuration concept of the anvil-assembly attitude-control system of Embodiment 2 for use in NOTES.

Figure 33:
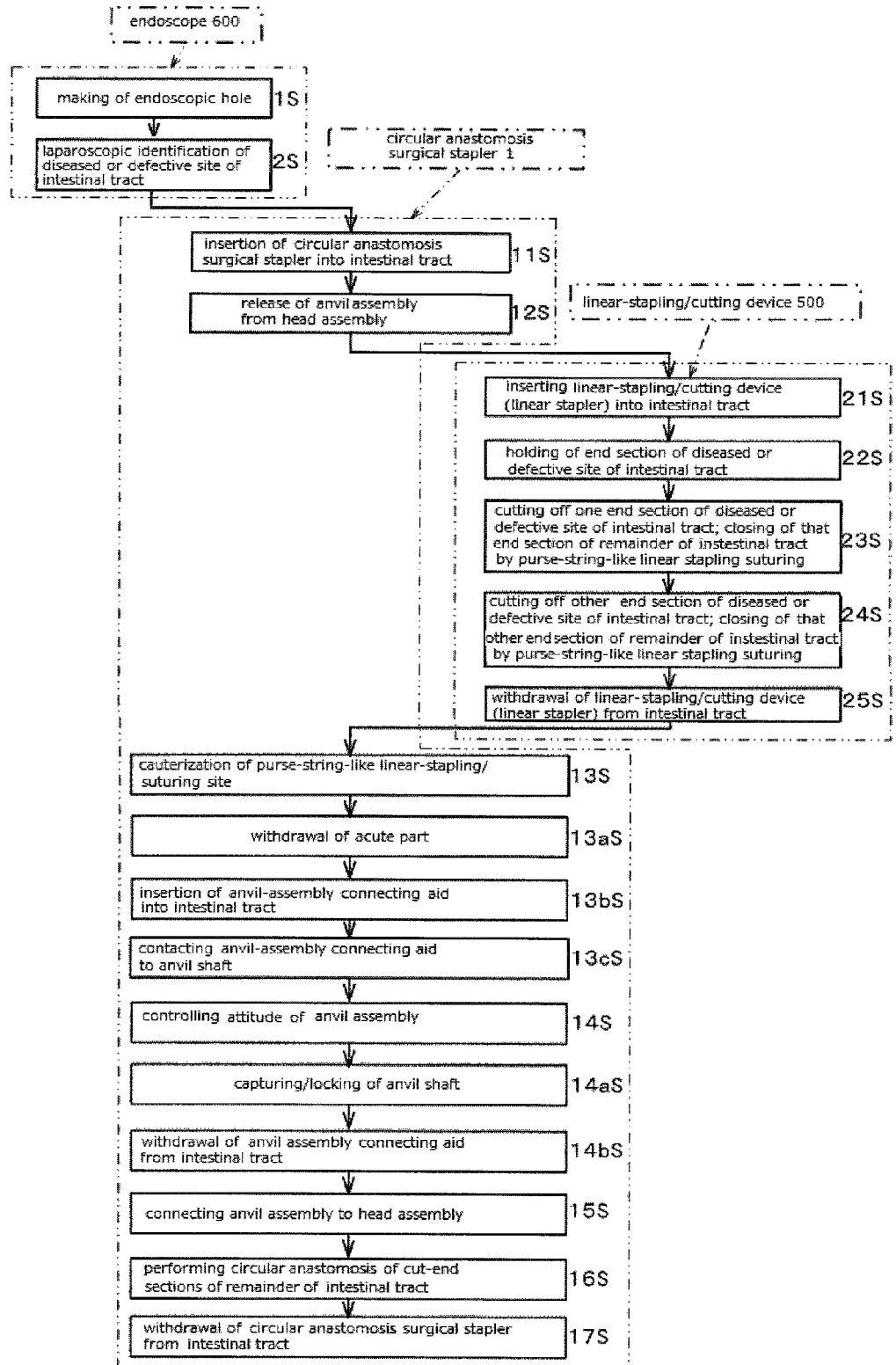

FIG. 33 is a block diagram showing the main procedural steps of the method of Embodiment 2 of the present invention for use in NOTES.

Figure 34:
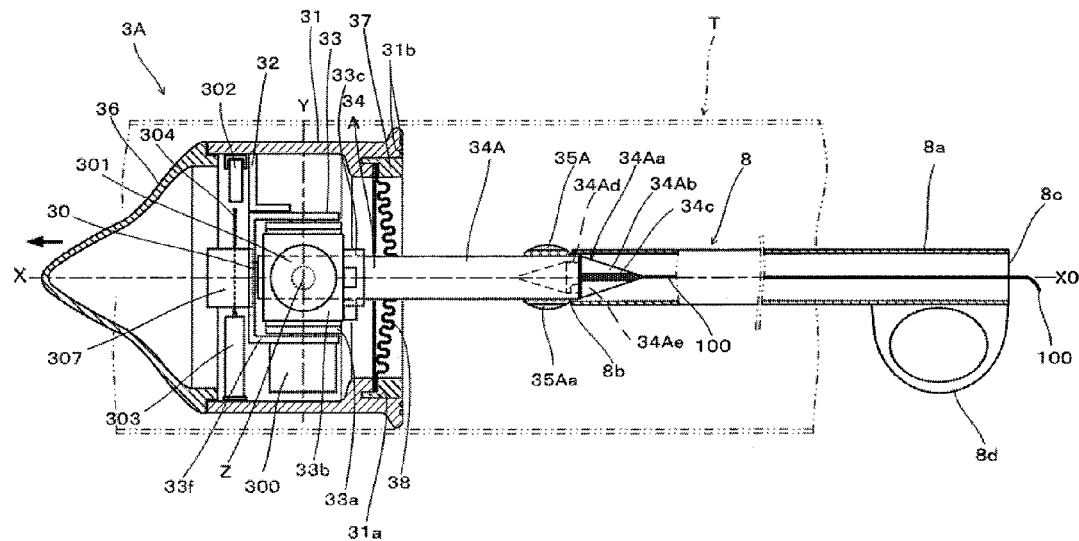

FIG. 34 is a vertical-section diagram showing the main configuration concept of the anvil-assembly insertion aid of the circular anastomosis surgical stapler in another modified mode of Embodiment 2, and further showing the anvil assembly coupled with the head assembly and inserted into the hollow organ.

Figure 35:
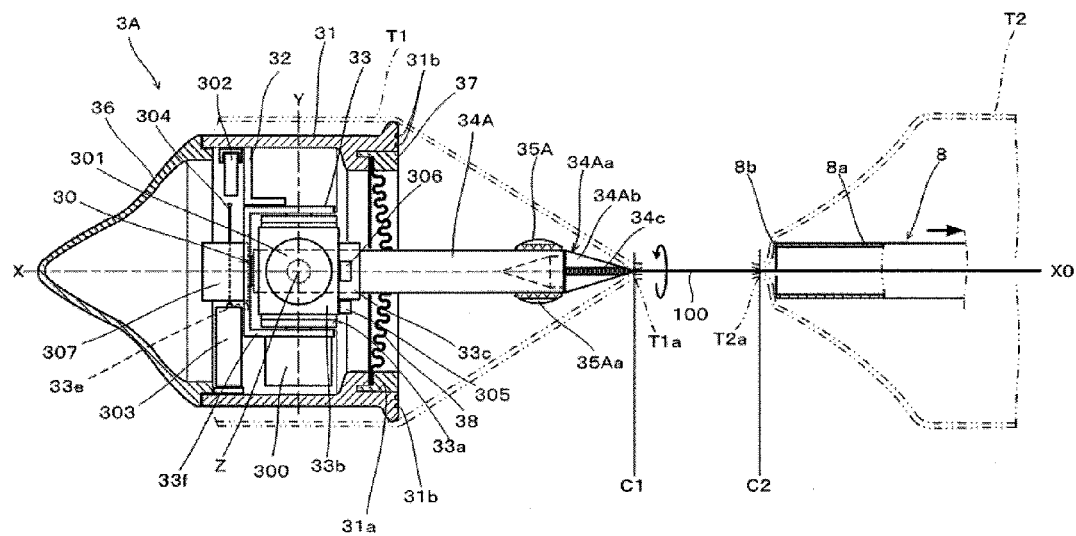

FIG. 35 is a vertical-section diagram showing a diseased or defective site of the hollow organ being cut off while at the same time the two cut-end sections of the remainder of the hollow organ are being closed by purse-string-like linear-stapling suturing by using the linear cutting/stapling device under the condition that the anvil assembly is separated from the anvil insertion aid, continuing the condition shown in FIG. 34.

Figure 36:
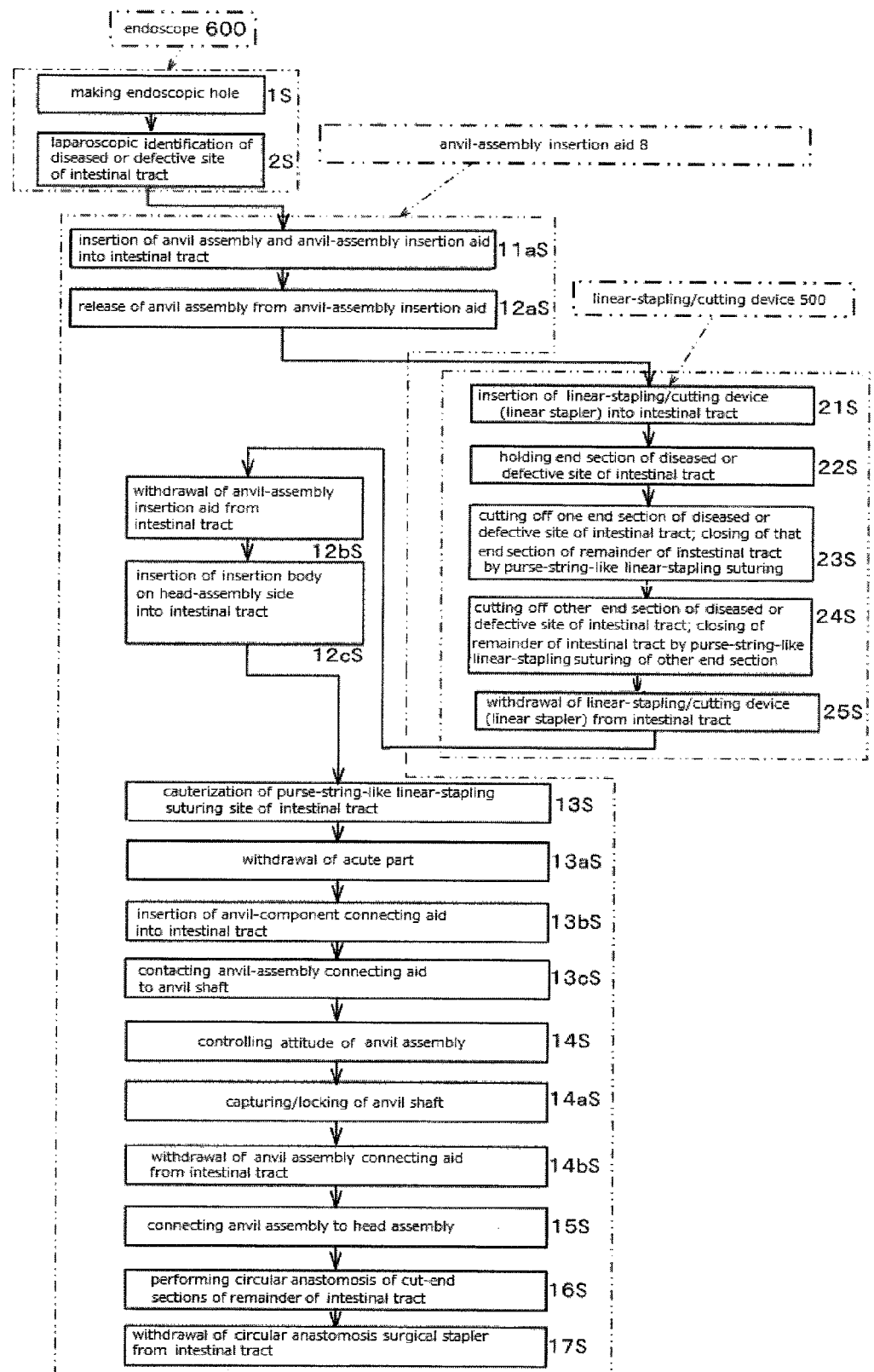

FIG. 36 is a block diagram showing the main procedural steps of the method for use in one additional modified mode of Embodiment 2 of the present invention.

Figure 37:
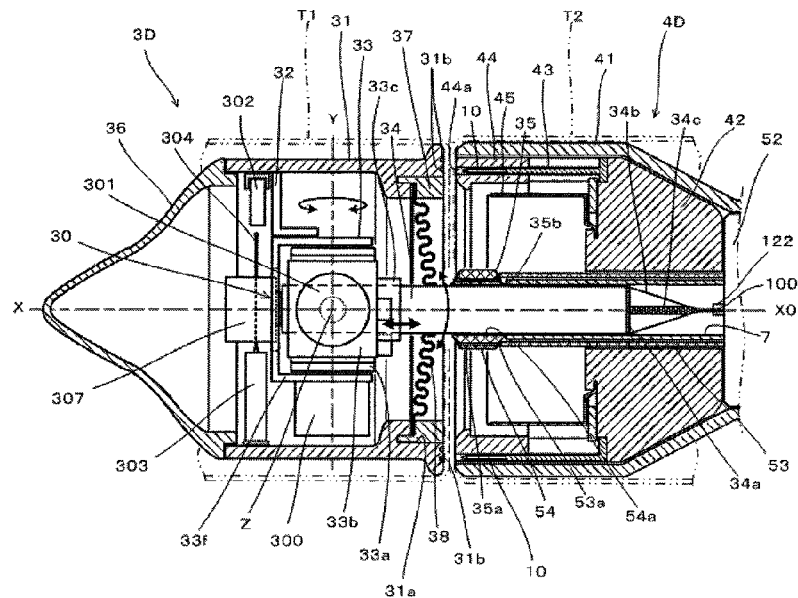

FIG. 37 is a vertical-section diagram showing the coupled condition of the anvil assembly and the head assembly of the circular anastomosis surgical stapler in one additional modified mode of Embodiment 2 of the present invention.

Figure 38:
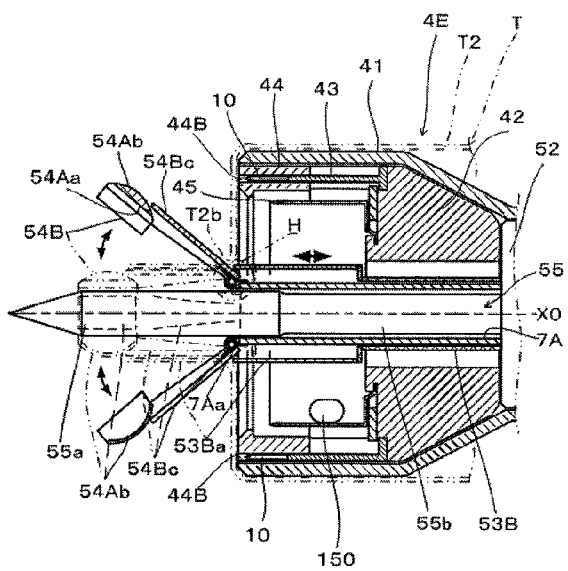
Figure 38:
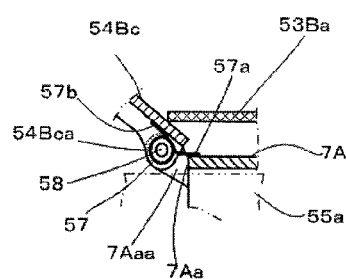

FIG. 38 is a vertical-section diagram showing the opened condition of the locking portion of the circular anastomosis surgical stapler in one additional modified mode of Embodiment 2 of the present invention.

Figure 39:
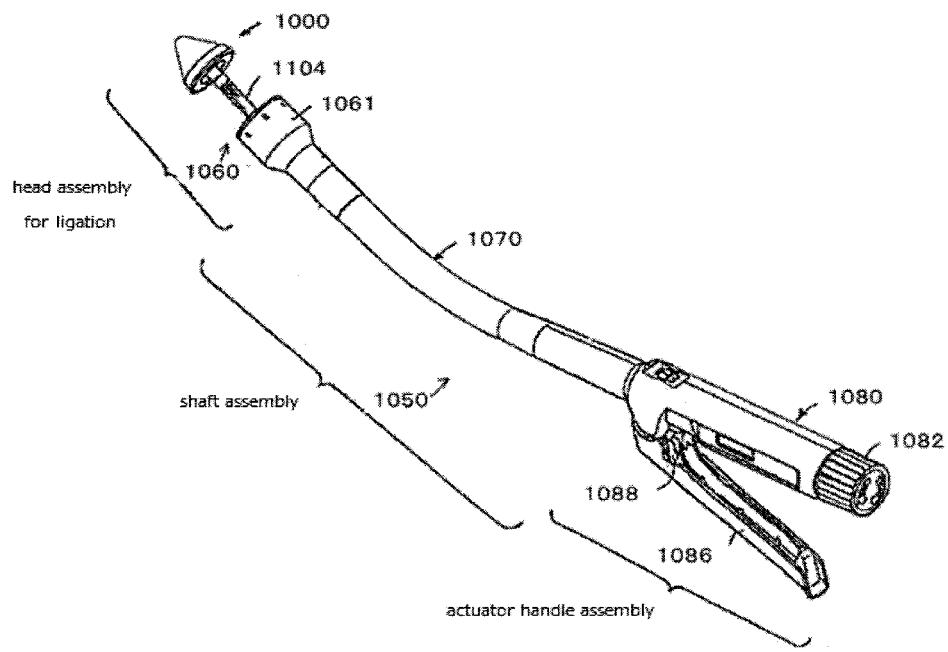

FIG. 39 is an outline view showing an example of an existing anastomosis surgical stapler for use on the digestive tract.

Figure 40:
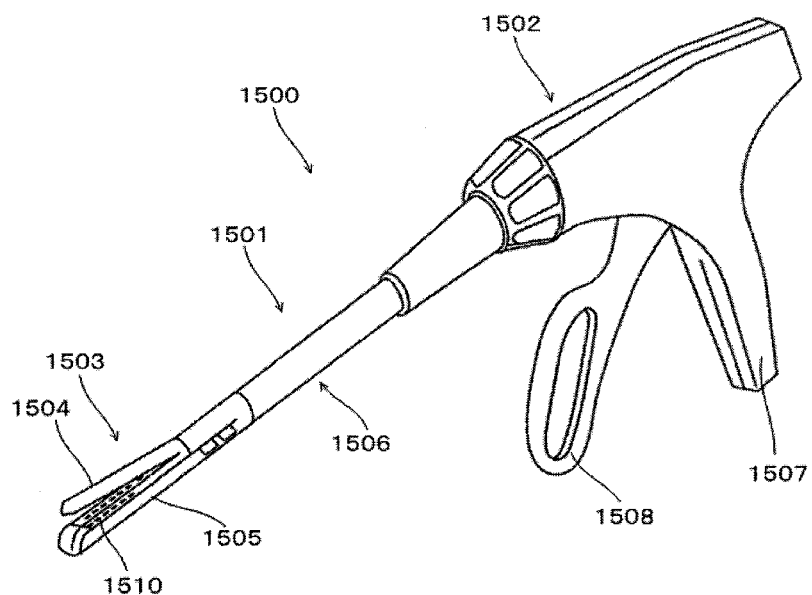

FIG. 40 is an outline view showing an example of an existing cutting/stapling device.

DETAILED DESCRIPTION

Embodiment 1

In the following, concrete examples for carrying out the present invention's system for use in NOTES are explained precisely, referring to the attached drawings.

Figure 1:
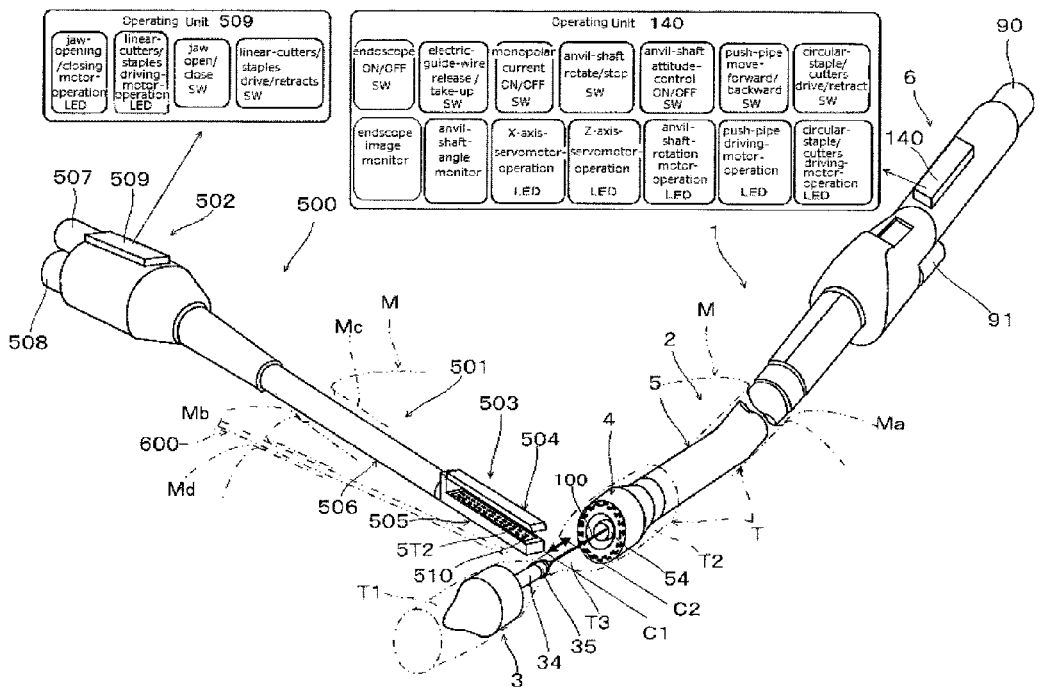
FIG. 1 is a conceptual diagram of the system for use in NOTES, showing the main configuration concept in one implementation form (Embodiment 1) for carrying out this invention.
Figure 2:
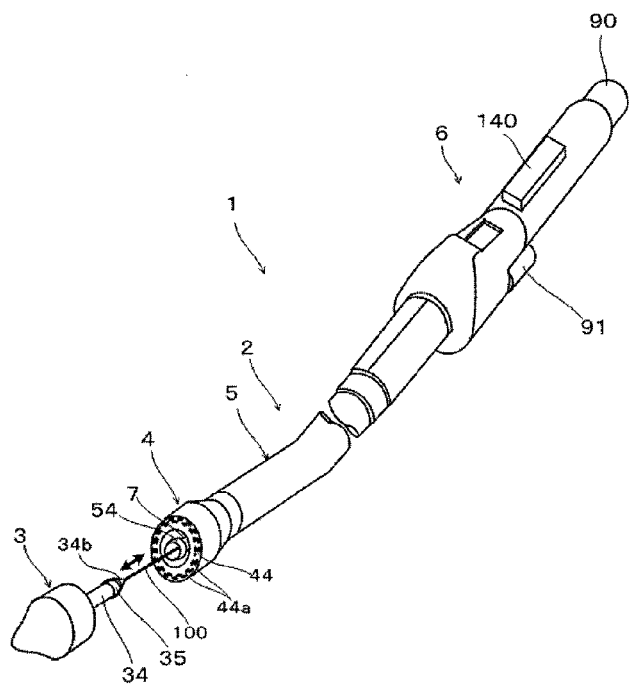
FIG. 2 is a perspective diagram of the circular anastomosis surgical stapler of the system for use in NOTES, showing the main configuration concept.
Figure 3:
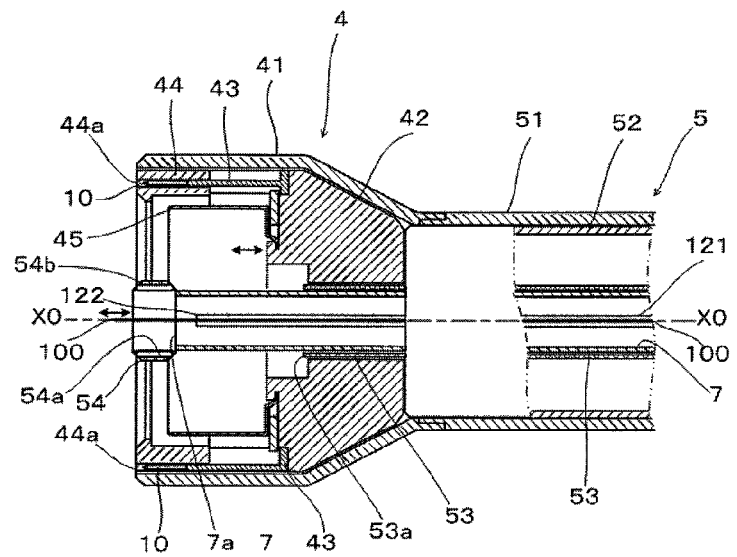
FIG. 3 is a vertical-section diagram of the head assembly shown in FIG. 2.
Figure 4:
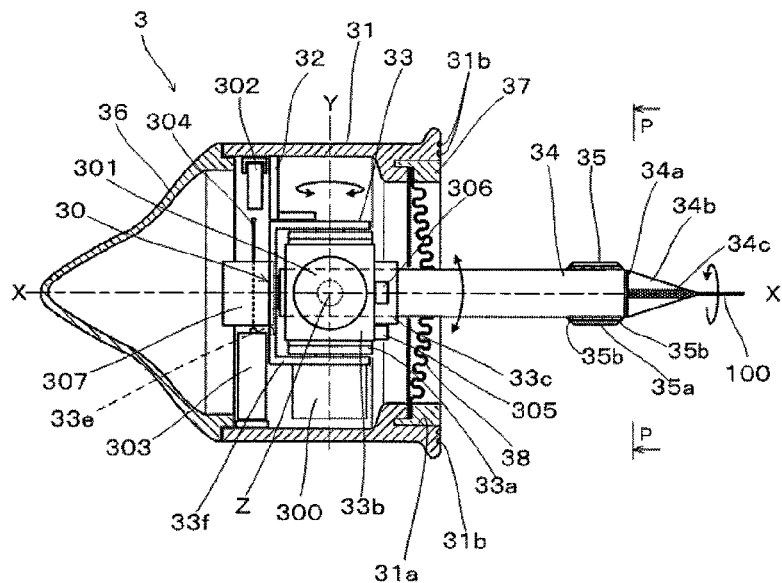
FIG. 4(*a*) is a vertical-section diagram of the anvil assembly shown in FIGS. 2, and 4(*b*) is a cross-sectional diagram along section lines P-P shown in FIG. 4(*a*).
Figure 4:
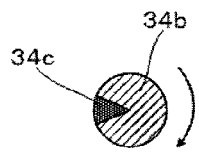
Figure 5:
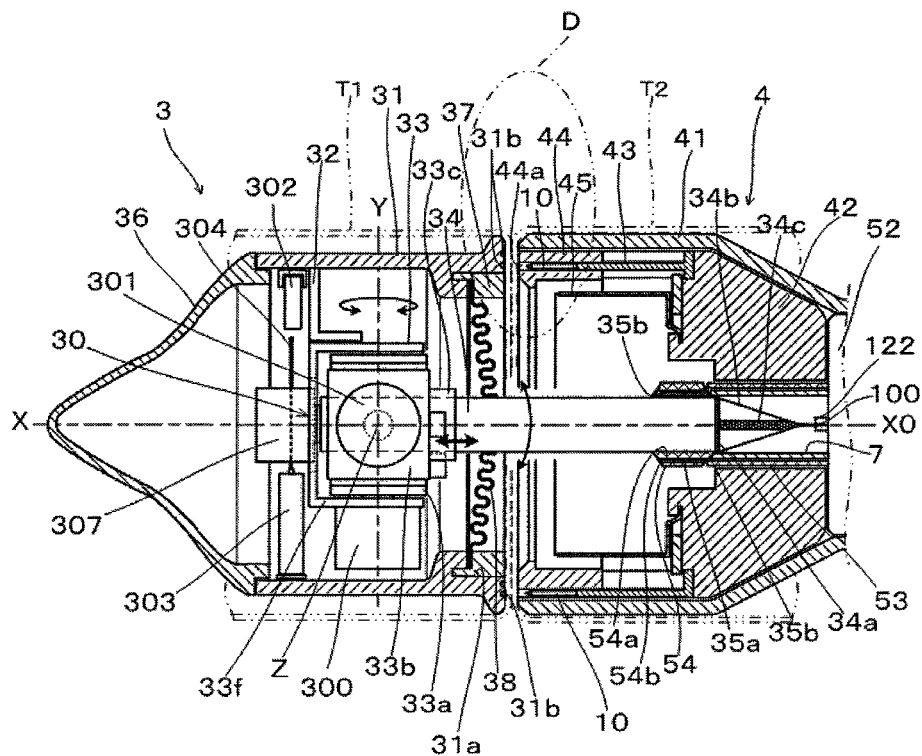
FIG. 5 is a vertical-section diagram of the anvil assembly and the head assembly shown in FIG. 2, coupled with each other.
Figure 6:
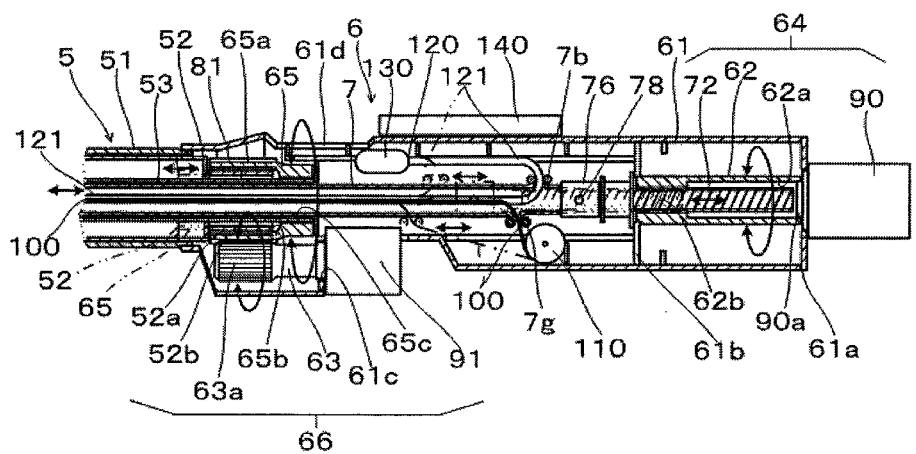
FIG. 6 is a vertical-section diagram showing the main configuration concept of the operating assembly shown in FIG. 2.
Figure 7:
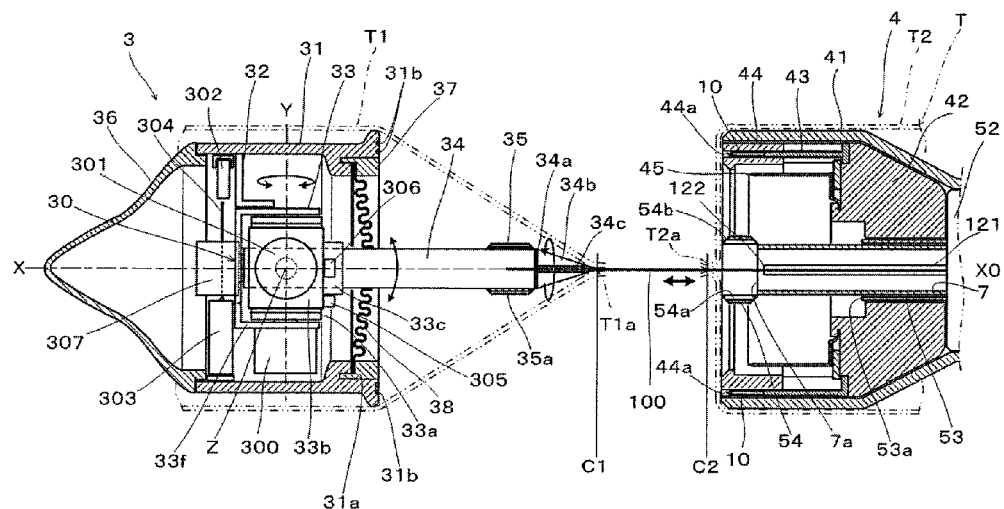
FIG. 7 is a vertical-section diagram of the anvil assembly and the head assembly shown in FIG. 2, decoupled from each other.
Figure 8:
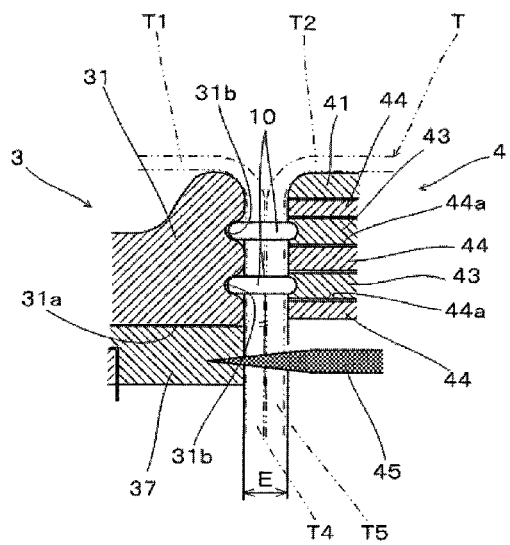
FIG. 8 is an enlarged sectional diagram of the D portion shown in FIG. 5.

FIG. 1 is a conceptual diagram of the system and method for use in NOTES showing the main configuration concept in one implementation form (Embodiment 1) for carrying out the this invention. FIG. 2 is a perspective diagram of the circular anastomosis surgical stapler 1 for the system for use in NOTES, showing the main configuration concept. FIG. 3 is a vertical-section diagram of the head assembly shown in FIG. 2. FIG. 4(a) is a vertical-section diagram of the anvil assembly shown in FIG. 2, and FIG. 4(b) is a cross-sectional diagram taken along the section lines P-P shown in 4(a). FIG. 5 is a vertical-section diagram of the anvil assembly and the head assembly shown in FIG. 2 and coupled with each other. FIG. 6 is a vertical-section diagram showing the main configuration concept of the operating assembly shown in FIG. 2. FIG. 7 is a vertical-section diagram of the anvil assembly and the head assembly shown in FIG. 2, decoupled from each other. FIG. 8 is an enlarged sectional diagram of the E-portion shown in FIG. 6. Also, all of the attached drawings are conceptual diagrams showing the main configuration concept expressed at NTS scale, and, especially in FIGS. 3-5, the radial direction is enlarged compared to the axial direction in order to easily show the inside configuration.

The system of Embodiment 1 for use in NOTES is as shown in FIG. 1, and comprises: (1) a circular anastomosis surgical stapler 1 that (a) is inserted via a natural orifice Ma of a body M to inside a hollow organ T that has a diseased or defective site; and (b) performs circular anastomosis of the two cut-end sections of the remainder of the hollow organ from inside the hollow organ T after the diseased or defective site has been cut off and removed from the remainder of the hollow organ, which at the same time has been closed by purse-string-like linear-stapling suturing of the two cut-end sections of the remainder of the hollow organ; (2) a linear cutting/stapling device 500 that is inserted via an endoscopic hole Mb or Md that is opened on the body M so that endoscopic instruments can be inserted into the body via a cannula Mc, and that cuts off and removes the diseased or defective site T3 from the remainder of the hollow organ T and at the same time closes the cut-end sections of the remaining hollow organ T by purse-string-like linear-stapling suturing from outside the remainder of the hollow organ T. It is desirable to provide in this system a number of endoscopes 600 inserted via endoscopic holes Md, Mb in order to monitor the surgical procedures described above from outside of the hollow organ T.

The circular anastomosis surgical stapler 1 of Embodiment 1 is as shown in FIGS. 1, 2, and includes: (a) an anvil assembly 3 that configures the forward portion of the device and that has an anvil shaft 34 on its rear end along the main axis (X-shaft); (b) a head assembly 4 that sits opposite to the anvil assembly 3 and includes a circular cutter 45 (see FIG. 3) for cutting off in the cylindrical direction a specified section of a hollow organ T; (c) one or more annular rows of anastomotic staples 10 for use in circular anastomosis of the two cut-end sections of the remainder of the hollow organ T; (d) an insertion body 2 that has a long, flexible supporting shaft 5 that is connected to the head assembly 4; (e) a coupling (engaging) mechanism that is equipped with a locked portion 35 (see FIG. 4) and a locking portion 54 (see FIG. 3) which are provided on the anvil shaft 34 and in the head assembly 4, respectively, and are detachably coupled to each other; and (f) an operating assembly 6 that is connected to the rear end of the insertion body 2 and that controls the locking/unlocking of the coupling mechanism, the driving of the anastomotic staples 10 and the circular cutter 45, and other operations.

The head assembly 4 comprises: (a) a tapered head outer casing 41, whose rear-end diameter is reduced to equal the outer diameter of the support shaft 5; (b) a staple cartridge 44 that is housed in the front end of the head outer casing 41, and that includes one or more annular rows of staple accommodation slots 44a that accommodate a number of anastomotic staples 10 (see FIG. 2); (c) a tubular circular cutter 45 that has the same central axis as the above-mentioned parts 41, 44, 44 in the staple cartridge 44; (d) a tubular staple-driving finger 43 that is housed at the rear end of the head outer casing 41, and that drives the anastomotic staples 10 outside the front-end surface of said staple cartridge; (e) a staple/cutter driver 42 that fixes the respective rear ends of the tubular-shaped staple-driving finger 43 and the circular cutter 45 and simultaneously drives the anastomotic staples 10 and the circular cutter 45 together forward along the main axis (X0).

A push tube 7 and connecting pipe 53 are inserted (see FIG. 6) from the operating assembly 6 via the supporting shaft 5 and arranged to have the same central (principal) axis as the head assembly 4, and the front ends of the push tube and the connecting pipe 7a, 53a are leaded to the inside of the head assembly 4. The rear end of the connection pipe 53 is fixed to the inside of the operation assembly 6. Details regarding the push tube 7 are presented below.

The staple/cutter driver 42 is connected to the front end of a drive tube 52 and is loosely mounted on the outer surface of the connecting pipe 53 so as to be movable back and forth via the drive tube 52 by the operating assembly 6, as described later. Due to the driving by the staple/cutter driver 42, a number of anastomotic staplers 10 and the circular cutter 45 are driven forward at the same time.

The above-described members of the head assembly 4 can be the same as those described in Patent Document 1, for example.

A locking portion 54 is provided at the front end 7a of the push tube 7, and it detachably captures the locked portion 35 on the anvil shaft 34 that protrudes at the rear end of the anvil assembly 3, as will be described below (see FIGS. 3 and 5). The configuration and function of the locking portion 54 and the push tube 7 also are described later.

The push tube 7 is loosely inserted in the connection pipe 53 so as to be movable back and forth via the locking portion 54 of the front end so as to impact the front end of the anvil shaft 34 of the anvil assembly 3, which is pulled toward the head assembly 4 by the operating assembly 6 and into the interior of said push tube 7, and on the other hand, to push out the anvil shaft 34 and to separate the anvil shaft 34 from the locking portion 54 (see FIGS. 5 and 6).

A wireless-endoscope insertion-tube body 121 and wireless-endoscope front end 122 are inserted from the operating assembly to near the front end 7a of the push tube 7, passing via the support shaft 5. An electric guide wire 100, which is a thin wire guide, also is inserted (see FIGS. 3-5). The configuration inside the push tube 7 and the configuration of the anvil assembly 3 are among of the main distinctive features of the present invention, in which a unique technology is included. These configurations and functions are precisely explained later.

As shown in FIG. 4, the anvil assembly 3 comprises: (1) a tubular anvil 31; (2) a hollow, conical end cap 36 that has a small, convex-curved face and that is coupled detachably at the front end of the tubular anvil 31; (3) a tubular lining washer 37 of that is housed in the groove portion 31a and that receives a blade edge of the circular cutter 45; (4) an anvil shaft 34 that protrudes at the rear end of the anvil 31 along the main axis (X axis), with said anvil shaft 34 connected by its rear end to a trocar 34b; (5) an anvil-assembly-attitude control mechanism 30 that automatically controls the anvil-assembly's inclined attitude against the anvil shaft 34, which is rotatably supported on the anvil-shaft support 33c that is installed in the middle of the anvil 31 and fixed to a bracket 32 that is mounted in a protruding condition inside the anvil 31; (6) a flexible cover 38 that seals the inside of the anvil assembly 3, whose outer circumference is clipped between the groove portion 31a and the lining washer 37, and whose inner circumference is fixed on the superficies of the anvil shaft 34 near the anvil-shaft support 33c.

A number of staple-forming grooves 31b are formed at the rear-end face of the anvil 31 on the respective circumferences of the two concentric circles that correspond to the staple accommodation slot 44a that is at the front-end face of the staple cartridge 44 inside the head assembly 4. A number of staple-forming grooves 31b respectively receive a number of anastomotic staples 10 driven from the staple accommodation slot 44a and bend the respective tips of the anastomotic staples 10, being pressed by the tubular staple-driving finger 43, so as to perform circular anastomosis of the two cut end sections of the remainder of the hollow organ.

A trocar 34b that has a monopolar electrode 34c on its rear end is connected at the rear end of the anvil shaft 34 via the insulator 34a. The anvil shaft 34, the insulator 34a, and the trocar 34b are all connected at almost equal radii, and the rear end of the trocar 34b, which has the monopolar electrode 34c, is formed as a sharp leading shape so as to easily penetrate the purse-string-like linear-stapling suturing sites T1a, T2a on the two portions T1, T2 of the remainder of the hollow organ (see FIG. 7), as described below. The reasons for using the insulator 34a and the monopolar electrode 34c are presented below.

As shown in FIGS. 4(*a*), (*b*), the monopolar electrode 34c of appropriate length is exposed and buried in a narrow band-like manner in the axial direction on the outer peripheral surface at the rear end of the trocar 34b. The exposed width and length of the monopolar electrode 34c are set so as to correspond to the characteristic features, such as the thickness of the tube walls, of the purse-string-like linear-stapling suturing sites T1a, T2a on the two portions T1, T2 of the remainder of the hollow organ (FIG. 7).

Because the monopolar electrode 34c is exposed and buried in a narrow, band-like manner on the outer peripheral surface at the rear end of the trocar 34b, the cauterization of the respective purse-string-like linear-stapling suturing sites T1a, T2a is done sequentially in the axial direction by galvanization of monopolar electricity to the monopolar electrode 34c, which has the effect of increasing the efficiency of the cauterization.

The anvil shaft 34, which is coupled with the trocar 34b, is connected to a rotating means, as described later, being supported rotatably on an anvil support shaft 33c, and is rotated by the rotating means when the monopolar electrode 34c is galvanized by monopolar electricity.

The anvil shaft 34, which is connected to the trocar 34b, rotates when the monopolar electrode 34c is galvanized by the monopolar electricity, so as to prevent the branding of the respective purse-sting-like suturing sites T1a, T2a on the two portions of the remainder of the hollow organ T (see FIG. 7) that would otherwise result due to the galvanization of the monopolar electrode 34c by monopolar electricity, which has the effect of further increasing the efficiency of the cauterization.

A convex-shaped locked portion 35 is formed on the outer surface of the anvil shaft 34 near the forward part of the insulator 34a and is coupled with and fixed to the locking portion 54 that is provided at the front end of the push tube 7 in the head assembly 4.

As shown in FIGS. 5 and 8, the coupling mechanism, which is composed of the locking portion 54 and the locked portion 35, is necessarily provided with: (1) a function that keeps those portions connected so that the anvil assembly 3 faces the head assembly 4 but is apart from the head assembly 4 by the specified gap E; and (2) a positioning function that controls and mechanically specifies the angles around the respective main axes (X-axis, X0-axis) of the anvil assembly 3 and head assembly 4, so that the staple accommodation slots 44a are positioned opposite to their corresponding staple-forming grooves 31b.

For this reason, the coupling mechanism can be made having the same configuration as those of existing embodiments, such as those described in Patent Document 1. As an example of the present embodiments, the coupling mechanism provides a spline mechanism so that the locking portion 54 and the locked portion 35 freely move slidably in the axial direction to and from each other, though their rotation around the main axes (X-axis, X0-axis) is restrained. That is, concave spline grooves (female splines) 54a are formed on the inner surface of the locking portion 54, and convex spline grooves (male splines) 35a are formed on the outer surface of the locked portion 35, in such a way that the concave an convex grooves are able to engage each other. Therefore, the above-mentioned two angles around the respective main axes (X-axis, X0-axis) of the anvil assembly 3 and the head assembly 4 are controlled and mechanically specified so that the staple accommodation slots 44a are positioned opposite to the staple-forming grooves 31b.

The two ends of the respective outer surfaces of the locked portion 35 and the locking portion 54 are chamfered and become smooth, inclined faces, so that the cauterized opening of the respective purse-string-like linear-stapling suturing sites T1a, T2a on the two portions T1, T2 of the remainder of the hollow organ are easily penetrated, and the locked portion 35 is easily mated and engaged with the locking portion 54.

The locking portion 54 can be made of electroactive polymer (EAP) material, which constricts due to galvanization. In this case, the locking portion constricts due to galvanization and tightly holds the locked portion 35, and stopping the galvanization releases the holding of the locked portion 35.

If a dielectric elastomer is placed in a strong electric field, it constricts in the electric field and expands in the direction perpendicular to the electric field. This deforming force is referred to as a Maxwell stress. If a condenser-like member that is made of EAP dielectric bodies so that it has elasticity similar to rubber is set between two charged electrode plates that are then galvanized, a positive charge is stored in one electrode and a negative charge is stored in the other electrode. Attracting forces arise, and the condenser-like member is pressed by these forces, and then the EAP dielectric bodies' quality of expanding toward the surface is used to cause the locking portion to lock. Such EAP materials are manufactured and sold, for example, in the U.S.A by Artificial Muscle Inc. and by Santa Fe Science and Technology, and in Japan by Emex Co., Ltd.

The monopolar electrode 34c is installed on the rear end of the trocar 34b, which is connected to the rear end of the anvil shaft 34. The electric guide wire 100 (a thin wire guide) is inserted from the operating assembly 6 to the head assembly 4, passing via the inside of the push tube 7, and the electric guide wire 100 is then connected to the monopolar electrode 34c. The electric guide wire 100 has the following three functions when circular anastomosis of the two cut ends of the diseased or defective site T3 of the remainder of the hollow organ T is performed: (1) a retracting function that retracts the anvil assembly 3, which is separated from the head assembly 4 by rolling up the electric guide wire 100, to the head assembly 4; (2) a continuation function of continuing the retracting operation (rolling up of the electric guide wire 100) and maintaining the coupling/locking of anvil assembly 3 and head assembly 4, and a supplementary function of unlocking and separating the anvil assembly 3 from the head assembly 4 by releasing the electric guide wire 100; and (3) a cauterized-site-opening function, by which the monopolar electrode is galvanized by monopolar electricity so that the anvil shaft 34 penetrates the respective purse-string-like linear-stapling suturing sites T1a, T2a on the two portions T1, T2 of the remainder of the hollow organ, and is pulled to the head-assembly side 4, where the respective purse-string-like linear-stapling suturing sites T1a, T2a on the two portions T1, T2 of the remainder of the hollow organ are sequentially cauterized, after which cauterization openings are formed by insertion of the trocar 34b into said suturing sites T1a, T2a. The insulator 34a then cuts off the monopolar electricity from the anvil shaft 34 to the anvil assembly 3.

The lock/unlock mechanism of the anvil assembly 3 and the head assembly 4 that employs the EAP materials can be replaced by the take-up/release of the electric guide wire 100 at the time of coupling/locking of the anvil assembly 3 and head assembly 4.

The anvil-assembly-attitude control mechanism 30 includes: (1) a biaxial oscillating mechanism 33 that can oscillate along the two axes (Y-axis, Z-axis) that orthogonally intersect the anvil main axis (X-axis); (2) angle sensors 305, 306 that are installed around the Y-axis and Z-axis at the anvil-shaft support 33c; and (3) a driving means that drives the biaxial oscillating mechanism 33 around the y-axis and Z-axis.

The biaxial oscillating mechanism 33 is a gimbal mechanism in which a second frame body 33b is installed in the first frame body 33f, which is fixed at the bracket 32 inside the anvil 31, and which oscillates around the Y-axis. An anvil-shaft support 33c is installed in the second frame body and supports the anvil shaft, which oscillates around the Z-axis.

As shown in FIG. 4, the anvil shaft 34 is inserted in the anvil-shaft support 33c and supported rotatably, and the front end of said the anvil shaft 34 is connected to the rotating shaft of the anvil-shaft-rotation motor 307, which is one of the driving means. In this case, a noninterference hole 33e is opened on the X axis, which is the center axis of the first frame body 33f, so that the first body frame 33f does not interfere with the anvil-shaft-rotation motor 307.

Said driving means are composed of a Y axis servomotor 300 that controls the driving of the second frame body 33b around the Y axis, and a Z axis servomotor 301 that controls the driving of the anvil-shaft support 33c around the Z axis, which have the effect of controlling the anvil shaft 34 attitude with high accuracy and high speed.

A battery 302 is provided in the anvil assembly 3 as the source of electricity for the Y, Z axis servomotors 300, 301, for the Y, Z axis-angle sensors 305, 306, and for the wireless transceiver (transmitter/receiver) 303 that communicates the control signals between those devices and the operating assembly 6.

As shown in FIGS. 2, 3, and 6, the support shaft 5 of the circular anastomosis surgical stapler 1 comprises: (1) an outer tube 51 whose front end is connected to the head outer casing 41 of the head assembly 4, and whose rear end is connected to an operating-assembly housing 61; (2) a driver tube 52; (3) a connecting pipe 53; and (4) a push tube 7—all of which are inserted concentrically inside the outer tube 51. The wireless-endoscope insertion-tube body 121 and electric guide wire 100 are passed inside and via the push tube 7. The members that constitute the support shaft 5 or other members inside the support shaft 5 are all made of flexible materials. As a result, members used for existing medical-purpose devices, such as a circular anastomosis surgical stapler or an endoscope, can be used.

As shown in FIG. 6, the operating assembly 6 of the circular anastomosis surgical stapler 1 includes: (1) an operating-assembly housing 61 that has an approximately tubular shape and that is connected with the outer tube 51 of the support shaft 5 at the front end of the operating-assembly housing 61; (2) a push-tube drive mechanism 64 that moves the push tube back and forth; and (3) a staple/cutter driving mechanism 66 that drives the anastomotic staples 10 and the circular cutter 45. In this embodiment, the push-tube drive mechanism 64 and the staple/cutter driving mechanism 66 are both electric-motor-driven and differ from the manual adjusting-knob mechanism and the staple/cutter driving-handle mechanism such as the prior art described in Patent Document 1.

The push-tube drive mechanism 64 comprises: (1) a mail-screw shaft 72 that is connected to the rear end of the push tube 7, which is passed inside and via the support shaft 5 and moves slidably back and forth via the U-shaped clip 76; and (2) a push-tube drive motor 90 mounted at the rear end of the operating-assembly housing 61. A hollow rotation nut 62 is supported rotatably at the front end of the push-tube drive mechanism 64 by a bracket 61b that is mounted in a protruding condition on the inner surface of the operating-assembly housing 61, and wherein a female-screw portion 62b that is formed at the front end of the rotation nut 62 is screwed with the male-screw shaft 72 that is housed in the rotation nut 62, and the rotation shaft 90a of the push-tube drive motor 90 is fixed into the motor connection hole 62a that is located on the rear-end face of the rotation nut 62.

Due to the rotation/reverse rotation of the rotation nut 62 that is driven by the push-tube drive motor 90, the push tube 7 moves back and forth by the driving force of the male-screw shaft 72 which is screwed with the rotation nut 62. At this time, the rotation around the center axis of the push tube 7 is restrained by the U-shaped clip 76 by which the rotation break screw 78 is inserted on the side face of the U-shaped clip 76. The male-screw shaft 72, which is connected to the push tube 7, retracts to a recessed position in its normal initial condition, as shown in FIG. 6.

An indicator indicates on the scale (not shown) of an indication window 61d the driving strokes of the staple/cutter driver 42 in response to the back-and-forth movement of the push tube 7. The other elements of a safety mechanism to prevent malfunction of the staple/cutter driving mechanism 66, the above-specified indicators, and so on, can be configured to be the same as those of many embodiments of existing circular anastomosis surgical staplers, and so illustrations and a detailed explanation are omitted here. Said safety mechanism engages with the indicator so that the indicator inclines backward along the scale marks (not shown) and indicates the specified driving stroke of staple/cutter driver 42 when the anvil assembly 3 is coupled and locked with the head assembly 4 while maintaining a specified gap E (see FIG. 8).

The size of the specified gap E between the anvil assembly 3 and the head assembly 4 at the time of the locking of both the assemblies almost equals the sum of the thicknesses on the anvil-assembly side T1 and head-assembly side T2 of the remainder of the hollow organ.

The staple/cutter driving mechanism 66 comprises: (1) a male-screw tube 52a that is connected to the rear end of the driver tube 52, which moves forward and pushes out the staple/cutter driver 42, on the circumference of which are formed male screws 52b and the male-screw tube 52a is passed via the inside of the driver tube 52 by the connecting pipe 53; (2) an externally-toothed rotating nut 65 that is rotatably supported by the coupling of a hollow rear-half area 65c with the connecting pipe 53, wherein external teeth 65a are formed on the forward half of the outer circumference and female screws 65b are formed on the forward half of the inner surface being screwed to the male tube 52a; (3) a staple/cutter driving motor 91 that is fixed at the lower opening portion of the front end of the operating-assembly housing 61; and (4) a staple/cutter driver shaft 63 whose rear end is connected to the rotation shaft of the staple/cutter driving motor 91 and on whose front end a pinion 63a is formed and mated with the outer tooth 65a of a male tube 52a.

The male-screw tube 52a that is connected with the driver tube 52 is usually back at a recessed position, as shown in FIG. 6. Due to the rotation/reverse rotation of the externally-toothed rotating nut 65 that is driven by the staple/cutter driving motor 91, the driver tube 52 moves back and forth by the driving force of the male-screw tube 52a, which is screwed to the externally-toothed rotating nut 65. At this time, the rotation of the externally-toothed rotating nut 65 around the central axis of the push tube 7 is restrained by a key/guide groove mechanism (not shown) that is installed between the connection pipe 53 and the push tube 7.

In Embodiment 1, the operating assembly 6 includes: (1) a take-up unit 110 that takes up or releases the electric guide wire 100 by a motor (not shown), and that is withdrawn from a roller-guide aperture 7g that is opened at the lower-rear portion of the push tube 7, wherein the electric guide wire 100 is connected to the monopolar electrode 34c on the rear end of the trocar 34b, which is inserted into the push tube 7 from the head assembly 4 and passed via the inside of the push tube 7, reaching the rear end of the push tube 7; (2) an insertion-tube body 121 that is withdrawn in a bent U-shape from the roller-guide aperture 7b that is opened at the upper-rear portion of the push tube 7; and (3) a wireless endoscope 120 that is equipped with a wireless endoscope unit 130 that is connected to the rear end of the insertion-tube body 121.

Instead of a conventional mechanical-control configuration composed of an existing safety mechanism, indicator, and so on, a safety/electronic-control configuration can be employed. Such a safety/electronic-control configuration includes, e.g., a take-up detecting sensor (not shown in the figure) for the take-up unit, wherein the lengths of the back-and-forth movements of the electric guide wire 100 that is connected to the anvil assembly 3 are measured by the take-up detecting sensor, and therefore the specified gap E between the anvil assembly 3 and the head assembly 4 and the specified strokes of the anastomotic staples 10 are displayed on a monitor (not shown in the figure), and the safety/electronic-control configuration can be applied by introducing a motor-drive interlock such as a staple/cutter driving motor 91. According to the modified Embodiment 1, a complicated mechanical-control configuration using existing safety mechanisms and indicators is eliminated, and the structure of the operating assembly 6 is thus simplified.

Figure 9:
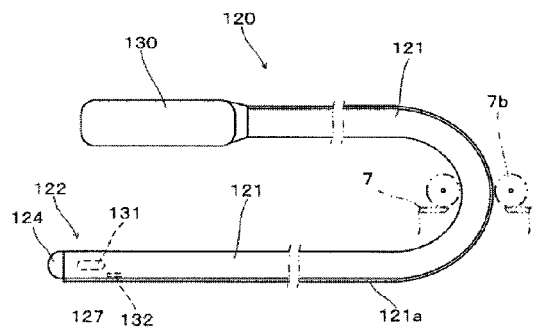
FIG. 9 shows the main configuration concept of the wireless endoscope shown in FIG. 2; 9(*a*) is a side-elevation view, and 9(*b*) is an elevation view of the front end of the wireless endoscope.
Figure 9:
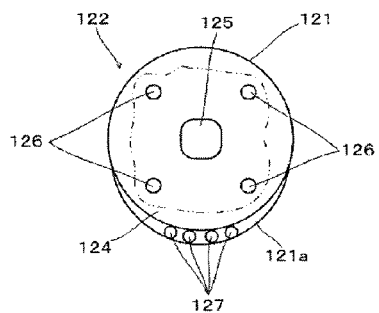

FIG. 9 shows the main configuration concept of the wireless endoscope 120. FIG. 9(a) is a side-elevation view of the endoscope 122, and FIG. 9(b) is a front-elevation view of the front end of the endoscope 122.

The wireless endoscope 120 in Embodiment 1 comprises a flexible insertion-tube body 121 whose rear end is connected with the front end of the endoscope 122 and whose front end is connected with the wireless endoscope unit 130 of the insertion-tube body 121. It is possible to employ a configuration similar to those described in Patent Application Publication (translation of PCT application) 2004-524076. A detailed explanation is omitted here.

As shown in FIGS. 9(a) and 9(b), the front end of the endoscope 122 is composed of: (1) an optical window 124 that is installed on the insertion-tube body 121 and formed to be a convex curved surface, such as an ellipsoid, that is suitable for optimizing the conditions of image graphics; (2) a CMOS imaging machine 125 that is arranged in the center of the front end of the endoscope 122; a number (number 4 in FIG. 9) of light-emitting diodes (LEDs) 126 that are arranged equally in the penumbra of the CMOS imaging machine 125; (3) a utility channel 121a that is equipped with a utility channel 127 that is installed in the lower-near portion of the endoscope 122 and used, for example, to supply air and cleansing water to the inside of the abdomen, or to suction blood and water from the inside of the abdomen.

Also, in the front end of the endoscope 122 are: (1) a wireless endoscope unit 130, (2) a wireless transceiver (transmitter/receiver) 131 that communicates control signals and images, (3) a CMOS imaging machine 125, and (4) a battery 132 that serves as the source of electric power for the wireless transceiver 131.

In Embodiment 1, it is possible to use the battery 132 as an electric-power source, by employing the light-emitting diodes (LEDs) 126 of a low-power-consuming element and the CMOS imaging machine 125. The CMOS is advantageous, when compared with a CCD, in its low-power consumption and in point of the system being on a chip.

In the wireless endoscope unit 130 are: (1) utility-control devices for supplying sources of air/cleansing water and for suctioning blood/water, (2) a control knob to move the front end of the endoscope 122, and (3) a wireless transceiver to communicate control signals to the operating assembly 6.

The image signals from the CMOS imaging machine 125 are transmitted via the wireless transceiver 131 using microwaves or wireless periodicity applying some kind(s) of digital- or analog-modulation technique(s). For example, an FSK (frequency shift keying)-modulation technique can be used to transmit digital images via a wireless channel. Some configuration elements, such as image sensors and irradiation sources, are single-use battery-operate units. The wireless endoscope 120 is superior in operability to a conventional wireless endoscope.

An operating unit 140 is provided at an upper position of the operating-assembly housing 61, as shown in FIG. 1, and it includes at least the following: an endoscope monitor; an anvil-shaft-angle monitor; a push-tube-driving-motor operation LED (push-tube-drive-motor operation-indicating lamp); a staple/cutter driving-motor operation LED (a staple/cutter-drive-motor c); an endoscope ON/OFF switch (hereinafter "SW") (a switch for operating the wireless endoscope); an electric-guide-wire release/take-up SW (take-up unit 110: electric-guide-wire 100 release/take-up SW); a monopole ON/OFF SW (monopolar current ON/OFF switch); an anvil-shaft rotation/stop SW; an X-axis-servomotor operation LED (X-axis servomotor operation-indicating lamp); a Y-axis-servomotor operation LED (Y-axis-servomotor Y-axis-servomotor operation-indicating lamp); an anvil-shaft-rotation motor operation LED (anvil-shaft-rotation-motor operation-indicating lamp); an anvil-shaft-attitude-control ON/OFF SW; a push-tube move-forward/rearward SW; a staple/cutter driver/retract SW and wireless transceivers 303, 131 installed in the anvil assembly 3; a wireless transceiver to communicate with the wireless transceivers 303, 131; and a battery.

Wireless operation using the operating unit 140 operates the circular anastomosis surgical stapler 1, as is explained below.

Figure 10:
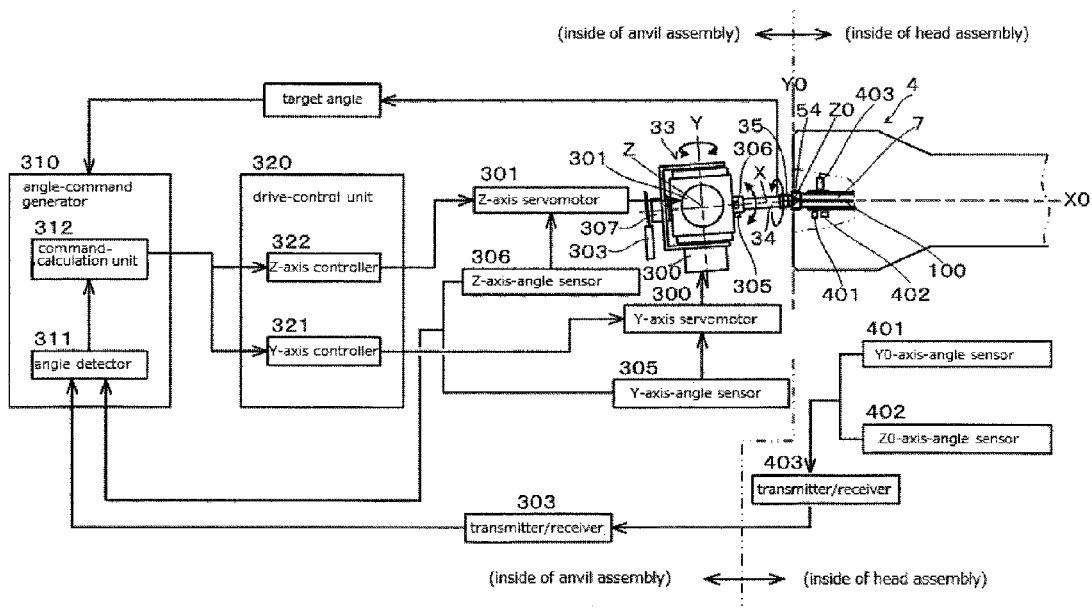
FIG. 10 is a block diagram setting forth the main configuration concept of the anvil-assembly attitude-control system for the system of Embodiment 1 for use in NOTES.

FIG. 10 is a block diagram showing the main configuration concept of Embodiment 1 of the anvil-assembly attitude-control system for the system for use in NOTES.

The anvil-assembly attitude-control system of Embodiment 1 comprises: (a) two axes (Y0-axis, Z0-axis)-angle sensors 401, 402 that are installed in the head assembly 4 and that orthogonally intersect the main axis (X0-axis) of the head assembly 4; (b) a head-assembly-side transceiver 403 that wirelessly transmits output from the above-mentioned angle sensors 401, 402; (c) an anvil-assembly-side transceiver 303 that is installed inside the anvil assembly 4 and that receives the output of the Y0-axis- and Z0-axis-angle sensors 401, 402 from the head-assembly-side transceiver 403; and (d) an angle-command generator 310 that includes (1) an angle detector 311 that detects all angle data, using the output of the Y-axis and Z-axis-angle sensors 305, 306 from the anvil-assembly-attitude control mechanism 30 and the output of the Y0-axis and Z0-axis-angle sensors 401, 402 from the anvil-assembly-side transceiver 303, and (2) a command-calculation unit 312 that calculates the index values of the rotation angles of the second frame 33b and the anvil shaft 34, based on the angle data from the angle detectors 311, and that generates angle commands from the second frame 33b and the anvil shaft 34, respectively, based on the index values of the rotation angles, and (e) a drive-control unit 320 that has a Y-axis controller 321 and a Z-axis controller 322 that separately control the Y-axis and Z-axis servomotors 300, 301, respectively, based on the anvil-assembly-attitude control mechanism 30.

The anvil assembly 3 that is separated from the head assembly 4 floats in an unstable position, inclining toward the head assembly 4 in the remainder of the hollow organ of the body M (see FIG. 1) and is suspended and inclining toward the head assembly 4. Under this condition, the electric guide wire 100 tries to pull the anvil assembly 3 and to connect the anvil assembly 3 to the head assembly 4, and at this time also applying the anvil-attitude control system. The rear end of the trocar 34b in the anvil assembly 3 is pulled by the electric guide wire 100 and is moved to inside of the locking portion 54 that is an anvil-shaft-coupling portion, or is moved closer to near the front end 7a of the push tube 7, in which the locking portion 35 is formed. Under this condition, setting a base point (temporally fixed point) at the rear end of the trocar 34b that meets the front end 7a of the push tube 7, the anvil-assembly-attitude control system automatically controls the attitude of the anvil assembly 3, referring to the target angle of the anvil shaft 34, which is roughly specified to fit the angle data of the head assembly 4, which are angles of the Y0-axis, Z0-axis-angle sensors 401, 402 at that point in time. The main axis (X-axis) of the anvil shaft 34 conforms to the main axis X0-axis of the head assembly 4, and then, as shown in FIG. 5, the anvil shaft 34 easily couples into the push tube 7 and a coupling/lock state can be achieved.

As described above, the circular anastomosis surgical stapler 1 of the present invention comprises: (1) an anvil-assembly-attitude control mechanism 30 that wirelessly controls the attitude of the anvil assembly 3 in relation to the anvil shaft 34; (2) a monopolar electrode 34c at the rear end of the trocar 34b; (3) an electric guide wire 100 that is connected to the monopolar electrode 34c and the take-up unit 110 of the electric guide wire 100; (4) a push-tube drive motor 90 that moves the push tube 7 back and forth, and presses the anvil assembly 3 forward and separates the anvil assembly 3 from the head assembly 4; (5) a staple/cutter driving mechanism 66 that causes the anastomotic staples 10 and the circular cutter 45 to move forward and backward; and (6) a wireless endoscope 120 that is inserted into and passes via the push tube 7 to the front end of the push tube 7. The entire system is controlled by a wireless electronic-control system that most differentiates the present invention's configuration from those of the existing circular anastomosis surgical staplers described in Patent Document 1. The functions of these configurations are explained in detail below.

Figure 11:
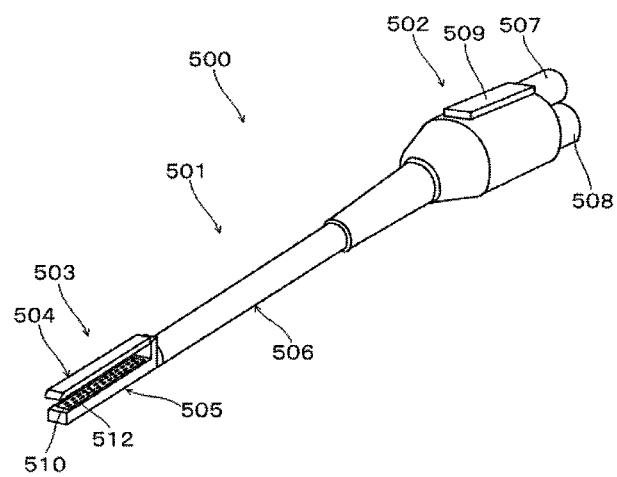
FIG. 11 is a perspective diagram of the linear cutting/ stapling device for the system for use in NOTES, showing the main configuration concept of Embodiment 1.
Figure 12:
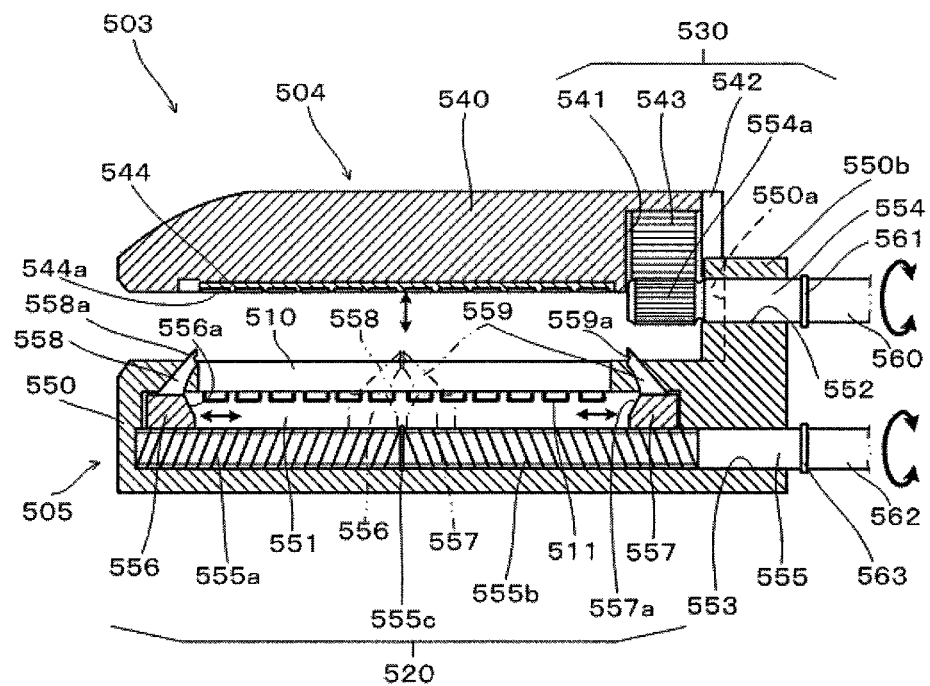
FIG. 12 is a vertical-section diagram showing the opening of the upper jaw of the end effector shown in FIG. 11.
Figure 13:
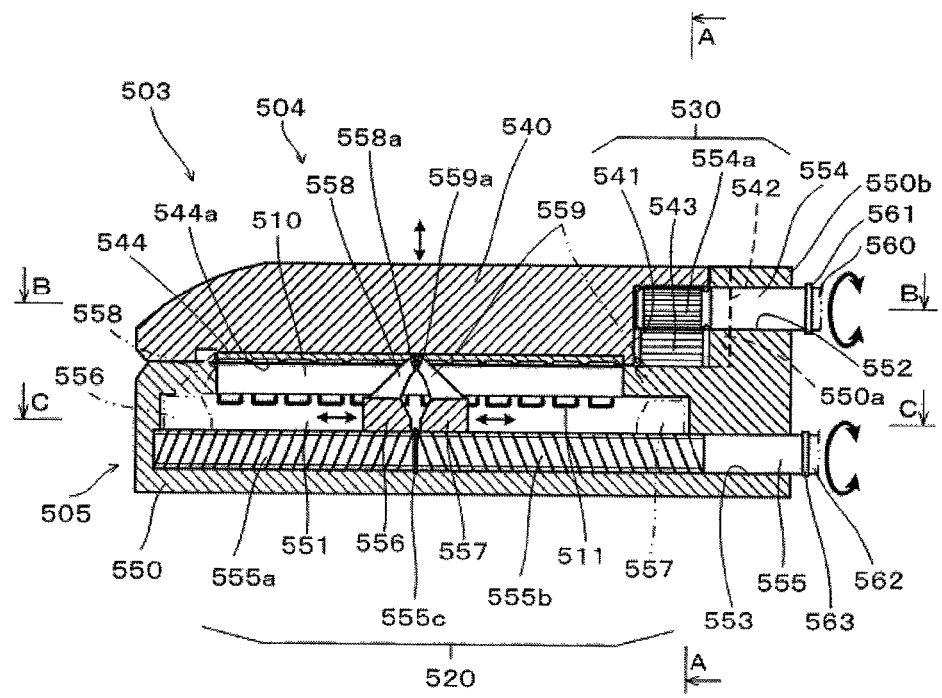
FIG. 13 is a vertical-section diagram showing the closing of the upper jaw of the end effector shown in FIG. 11.
Figure 14:
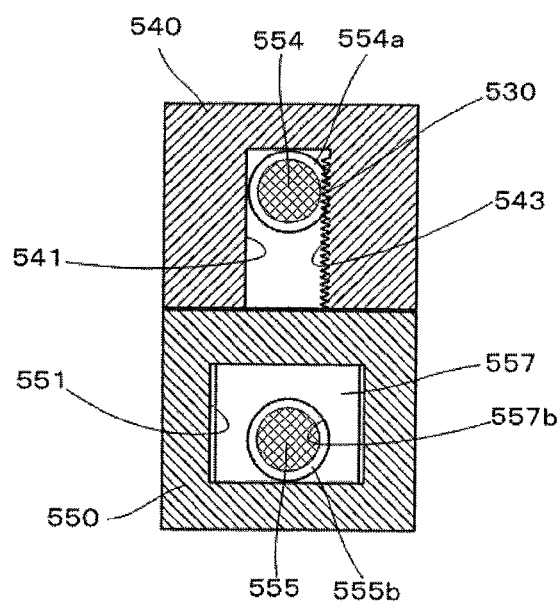
FIG. 14 is a cross-sectional diagram taken along section lines A-A shown in FIG. 13.
Figure 15:
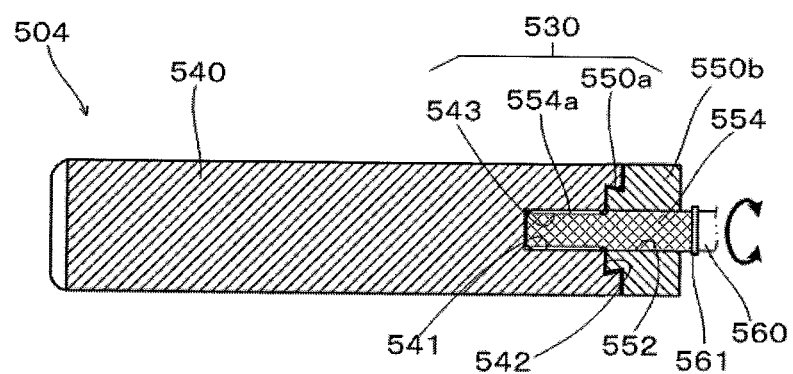
FIG. 15 is a cross-sectional diagram taken along section lines B-B shown in FIG. 13.
Figure 16:
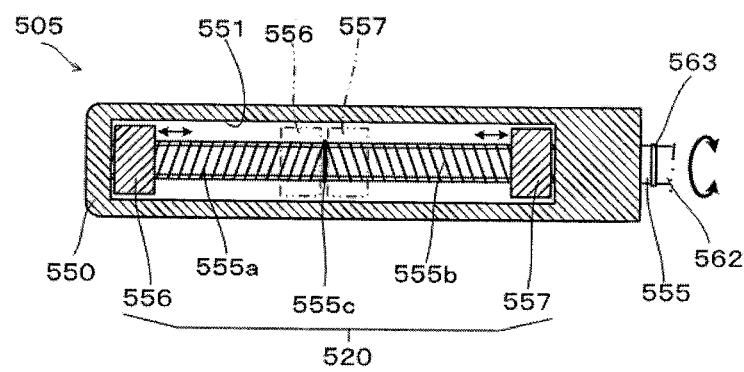
FIG. 16 is a cross-sectional diagram taken along section lines C-C shown in FIG. 13.

FIG. 11 is a perspective diagram of the linear stapler 500 for the system for use in NOTES, showing the main configuration concept in one mode (Embodiment 1) for carrying out the present invention, FIG. 12 is a vertical-section diagram showing the end effector 503 of FIG. 11 when the upper jaw is open. FIG. 13 is a vertical-section diagram showing the end effector 503 of FIG. 11 the upper jaw is closed. FIG. 14 is a cross-sectional diagram taken along section lines A-A shown in FIG. 13. FIG. 15 is a cross-sectional diagram taken along section lines B-B shown in FIG. 13. FIG. 16 is a cross-sectional diagram taken along section lines C-C shown in FIG. 13.

As is shown in FIGS. 1 and 11, the linear stapler 500 in Embodiment 1 of the present invention is comprised of, from its front end: (1) an insertion body 501, that is to be inserted into a body's abdominal cavity via an endoscopic hole, and that includes an end effector 503 that has (a) an upper jaw 504 that can open and close; (b) a lower jaw 505 that faces the upper jaw 504 and is equipped with two linear rows of suture staples 511 that linearly staple a specified section of a hollow organ, and a pair of (front-end/rear-end) linear cutters 558, 559 (see FIGS. 12 and 13) that can move back and forth from the front end and read end of the lower jaw 505 to the mid-area thereof; (2) a flexible, long support shaft 506 that is connected to the end effector 503; and (3) an operating assembly 502 that is connected to the support shaft 506 and that controls the driving of suture staplers and the operation of the linear cutter.

The linear stapler 500 of the present invention differs from those of conventional linear cutting/stapling devices (linear staplers)—e.g., the conventional linear stapler described in Patent Document 2—especially in regard to the pair of (front-end/rear-end) linear cutters 558, 559 and the linear staple/cutter driver (driving) mechanism 520 that drives these linear cutters (see FIG. 12), as described later. Except for these two main differences, the configuration of the members in the present device can be same as those of various kinds of conventional linear cutting/stapling devices (linear staplers).

As shown in FIG. 12, in Embodiment 1 the lower jaw 505 comprises: a lower-jaw body 550 whose rear end 550b can either be down as a flat rectangular shape of the plan view (see FIG. 16) or can stand upright to form an L shape; a staple cartridge 510 that is detachably housed in the upper surface of the lower jaw 550, facing the upper jaw 504, and that accommodates two linear rows of suture staples 511 in the longitudinal direction; a linear staple/cutter driver (driving) mechanism 520 that is installed in the channel 551 facing the lower plane of the staple cartridge 510 and that drives the pair of (front-end/rear-end) linear cutters 558, 559 to move back and forth opposite to each other.

When the rear end 550b is in the upright portion, a dovetail-groove-type slide groove is formed in front of the rear end 550b and engages with and supports the rear end of the upper jaw 504 and causes the upper jaw 504 to slide up and down. An upper-jaw opening/closing drive shaft 554 is inserted rotatably in the upper-shaft support hole 552 that is provided in the back-and-forth direction.

A number of staple accommodation slots 512 that accommodate a number of the suture staples 511 are provided in two linear rows in the staple cartridge 510, and said staple accommodation slots 512 pierce the staple cartridge 510 in the upper and lower directions (see FIG. 11).

As shown in FIGS. 12-14, the linear staple/cutter driver (driving) mechanism 520, 16, comprises: (1) a linear staple/cutter driver (driving) shaft 555 that is rotatably installed in the lower-shaft support hole 553 that is longitudinally formed in the channel 551 in the lower portion of the lower jaw 505, and that includes a male screw on which reverse screws in the right and left directions 555a, 555b are formed on the anterior and posterior halves of the male screw; and (2) a front-end staple-pushing (driving) member (hereinafter "front-end staple-driver") 556 and a rear-end staple-driver 557 that are provided, respectively, with a slope 556a, 557a, with both of said staple-drivers having a wedge mechanism to push out (drive), in order, the two linear rows of suture staples 511. The front-end staple-driving mechanism 556 and the rear-end staple-driving member (hereinafter rear-end staple-driver) 557 are threadedly engaged with the left and right reverse male screws 555a, 555b, and move back and forth in directions opposite to each other inside the channel 551, accompanying the reversible rotation of the linear staple/cutter driver shaft 555, so as to drive the suture staples 511.

As shown in FIGS. 12 and 13, a pair of linear cutters are arranged along either the left or right side of the staple cartridge 510 so as to pass via the staple cartridge 510, and are put in a standing position on the front-end staple-driver 556 and rear-end staple-driver 557 so that the two blade edges face each other and move toward the upper jaw 504. Respective concave notches 558a, 559a are formed on the upper blade edge of the (front-end/rear-end) linear cutters 558, 559, respectively. The concave notches 558a, 559a have a noninterference function so that only the hollow organ T will be incised, without cutting the thin wire guide (electric guide wire) 100 of the circular anastomosis surgical stapler 1 (see FIG. 1).

As shown in FIG. 13, it is desirable the upper blade edges of the pair of (front-end/rear-end) linear cutters 558, 559 overlap each other when they meet at the middle portion 555c of the linear staple/cutter driver shaft 555. By this configuration, the cutting of a specific portion of the hollow organ (FIG. 1) is carried out effectively. At this time, the concave notches 558a and 559a are also formed to have a noninterference function so that only the hollow organ T is incised, without cutting the thin wire guide (electric guide wire) 100 of the circular anastomosis surgical stapler 1.

The rear ends of the upper-jaw opening/closing drive shaft 554 and the linear staple/cutter driver (driving) shaft 555 are connected, respectively, to flexible drive shafts 560, 562, via couplings 561 and 563, and are driven by a motor of the operating assembly 602, as described below.

As shown in FIGS. 12 and 15, the upper jaw 504 in this Embodiment 1 can have the same configuration as that of one of the various kinds of existing linear cutting/stapling devices (linear staplers), and comprises: a rectangular upper-jaw body 540 corresponding to the lower jaw 505; a staple guide 544 in the lower portion of the upper-jaw body 540, opposite to the staple cartridge 510 of the lower jaw 505; and an upper-jaw opening/closing mechanism 530 that has the rectangular shape of the plan view and that is installed at the groove portion 541 and that opens and closes the upper jaw 504 in the upper and lower directions. A dovetail-groove-type slide groove 542 is formed at the rear end of the upper jaw 504, and the dovetail-groove-type slide groove 542 is slidably engaged/supported with the dovetail-groove-type slide groove 550a that is located in the upright portion of the rear-end 550b of the lower-jaw body 550.

A number of staple accommodation slots 512 (see FIG. 11) of the staple cartridge 510 that opposes the lower face of the staple guide 544 accommodate the two linear rows of suture staples 511, and a number of grooves for forming staples 544a are provided in the two linear rows and configure the suture staple 512 so that the cut-end sections of the diseased or defective site T3 of the remainder of the hollow organ T (see FIG. 1) that are to be closed by purse-string-like linear-stapling suturing correctly receive the respective blade edges of the suture staples driven from the staple accommodation slots 512 (as shown in FIG. 11).

The upper-jaw opening/closing mechanism 530 differs from that of existing linear staplers, as shown, for example, in FIGS. 12-15, and is comprised of: a rack 543 on one of the two sides of the groove portion 541 of the upper-jaw body 540; an upper-jaw opening/closing drive shaft 554 that has a pinion 554a on its front end and that mates with the rack 543; and a dovetail-groove-type slide groove 542 that is engaged/supported slidably with the dovetail-groove-type slide groove 550a of the lower-jaw body 550, and that enables the upper-jaw body 540 to slide up and down through the rack 543. The upper-jaw opening/closing drive shaft 554 rotates normally/reversely, which causes the upper-jaw body 540 to slide up and down via the rack 543, and said sliding makes the upper jaw 504 open and close with the lower jaw 505.

Next, employing the system for use in NOTES, including the circular anastomosis surgical stapler 1 and the linear stapler 500 of the present invention as explained above, the method for use in NOTES is explained, for example, regarding the medical procedures for cutting off a diseased or defective site T3 of a hollow organ T (e.g., an intestinal tract) and performing circular anastomosis of the cut-end sections of the remainder of the intestinal tract, referring to FIGS. 1-17.

Figure 17:
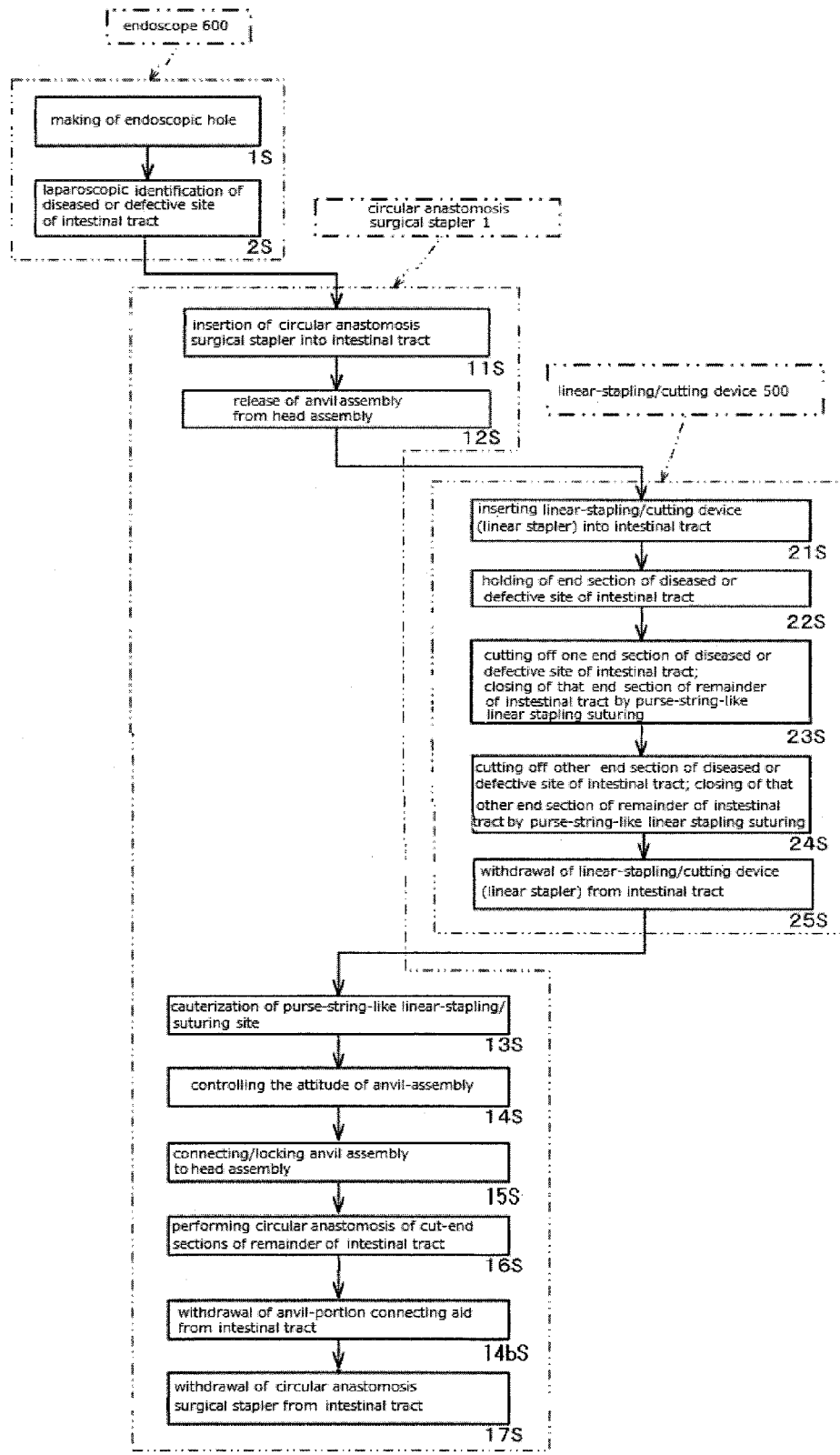
FIG. 17 is a block diagram showing the main procedures of the method for use in Embodiment 1 of the present invention.

FIG. 17 is a block diagram showing the main procedures of the method of Embodiment 1 of the present invention for use in NOTES.

The method of Embodiment 1 of the present invention for use in NOTES as applied to, for example, a body M, with the intestinal tract being the hollow organ T of that body, includes the following main steps.

First, the required number of endoscopic holes Mb, Md to enable endoscopic instruments to be inserted into the body are opened in the abdomen to make it possible to observe, using the endoscope 600 from outside of the intestinal tract T, the diseased or defective site T3, which has been identified by several kinds of diagnostics, (Step 1S: making endoscopic hole(s)).

The location of the diseased or defective site T3 of the intestinal tract T is confirmed by the endoscope 600 that is inserted via a cannula Mc that is inserted via said endoscopic holes Md and Mb (Step 2S: laparoscopic identification of diseased or defective site of intestinal tract). In the following steps (although a detailed explanation is omitted), the endoscope 600 is used to carefully observe the diseased or defective site and the location thereof from inside the intestinal tract T and via the (wireless) operating units 140 and 509, respectively, and via various kinds of monitors and the operation-indicating LED of the circular anastomosis surgical stapler 1 and the linear stapler 500. In this way, the NOTES is performed carefully.

After said step (2S) of laparoscopic identification of the diseased or defective site of the intestinal tract, the insertion body 2 of the circular anastomosis surgical staplers 1 of which the anvil assembly 3 is connected to the head assembly 4 is inserted via a natural orifice (e.g., the anus Ma) of the human body M until the front end of the anvil assembly 3 fully passes via the diseased or defective site T3 in the intestinal tract T (Step 11S: insertion of circular anastomosis surgical stapler into intestinal tract). At this time, as shown in FIG. 1, the anvil assembly 3 is inserted until the monopolar electrode 34c (FIG. 4) at the rear end of the trocar 34b passes near the front-end section C1 of the diseased or defective site T3 of the intestinal tract T and reaches the intestinal tract on the anvil-assembly side (in the direction of the mouth) T1.

Next, while the anvil assembly 3 that has been inserted into the intestinal tract on the anvil-assembly side T1 is being held by an endoscopic tool (not shown in the Figures) in the endoscope 600, so as to restrict the movement of the anvil assembly 3, the electric guide wire 100 is released using the release operation of the take-up unit 110 of the circular anastomosis surgical stapler 1. At the same time, the anvil assembly 3 is forced to move forward by the push-tube drive motor 90, and the anvil assembly 3 is pushed out via the coupling mechanism of the anvil shaft 34, after which the anvil assembly 3 is separated from the head assembly 4, with the anvil assembly 3 temporarily left inside the intestinal tract on the anvil-assembly side T1. Under this condition, the insertion body 2 on the head assembly 4 side is gradually withdrawn, and the head assembly 4 is forced to move back until the front end of the head assembly 4 passes via the rear-end section C2 of the diseased or defective site T3 of the intestinal tract and reaches the intestinal tract T1 on the anvil-assembly side (Step 12S: release of anvil assembly from head assembly). At this time, by the backward operation of the push-tube drive motor 90, the head assembly 4 is unlocked from and released from the anvil shaft 34 (the locking portion 54 separates from the locked portion 35), and the push tube 7 is moved back to its recessed position (see FIGS. 5 and 6). Said anvil-assembly separation is observed and confirmed from outside the intestinal tract T by the endoscope 600, and at the same time is observed and confirmed from inside the intestinal tract T by the wireless endoscope 120 that has been inserted in the head assembly 4 of the circular anastomosis surgical staplers 1.

After the endoscope 600 and wireless endoscope 120 confirm that the anvil assembly has been separated from the head assembly, the insertion body 501 having the closed-jaw end effector 503 of the linear stapler 500 is inserted near said diseased or defective site T3 of the intestinal tract T, through the cannula Mc via the endoscopic hole Mb or Md (Step 21S: insertion of linear stapler into intestinal tract).

When the anvil assembly is being released from the head assembly (Step 12S), it is also possible to withdraw the insertion body 2 on the head assembly 4 side and to move it back to position C2 of the intestinal tract T2, holding the anvil assembly 3 that has been inserted into the intestinal tract T1 on the anvil assembly 3 side (in the direction of the mouth) together with the hollow organ T1 from outside the hollow organ T1. By thus keeping the anvil assembly 3 near the front-end section C1 of the diseased or defective site T3 of the intestinal tract, it is possible to separate the head assembly 4 and to set it precisely near the rear-end section C2 of the diseased or defective site T3.

The jaw-opening/closing motor 507 of the operating assembly 602 of the linear stapler 500 is continuously operated to open the upper jaw 504 of the end effector 503, and to hold any of the near front-end/rear-end sections C1 C2 of the diseased or defective site T3 so that the upper jaw 504 of the end effector 503 is closed (Step of holding one end section of the diseased or defective site of the intestinal tract 22S). At this time, by using the endoscope 600 from outside of the intestinal tract T, it is confirmed that holding by the end effector 503 is done so that the center portion (corresponding to the center portion 555c of the staple/cutter driving shaft 555) of opening of the upper and lower jaw 504, 505 almost aligns with the central axis of one of the both two of the front-end/rear-end sections C1, C2 of the diseased or defective site T3.

After the endoscope 600 confirms said holding of one of the two front-end/rear-end sections C1, C2 of the diseased or defective site T3 of the intestinal tract T, the linear-staple/cutter driving motor 508 of the operating assembly 602 is operated, and the front-end linear-staple driver 556 and the front-end linear cutter 558, and the rear-end linear-staple-driver 557 and the rear-end linear cutter 55, respectively move in directions opposite from the front end and rear end of the end effector 503 to the center portion of the opening of the end effector 503, and approach each other. As shown in FIG. 7, due to the above-mentioned movement controlled by the operating assembly 602, a number of the suture staples 511 are driven, in order, from both the front end and rear end of the end effector 503 and one of the two of the front-end/rear-end sections C1, C2 of the diseased or defective site T3 of the intestinal tract is closed by purse-string-like linear-stapling suturing straight in the transverse direction (purse-string-like linear-stapling suturing site T1a or T2a) so as to wrap the electric guide wire 100 of said circular anastomosis surgical stapler 1. At the same time, the (front-end/rear-end) linear cutters 558, 559 (see FIGS. 12 and 13), which have in their middle area respective concave notches 558a, 559a for non-interference, cut off, straight in the transverse direction, only said diseased or defective site T3 and then remove only said site T3 from the remainder of the intestinal tract having a purse-string-like linear-stapling suturing site T1a or T2a, as if pinching the near front-end/rear-end sections C1, C2 of the diseased or defective site from their respective outsides, without cutting the electric guide wire 100 of the circular anastomosis surgical stapler 1 (Step 23S: cutting off one end section of diseased or defective site of intestinal tract and closing that cut-end section of the remainder of intestinal tract by purse-string-like linear-stapling suturing).

The other of the front-end/rear-end sections C1, C2 of the diseased or defective site T3 of the intestinal tract is processed completely using the same procedures as those previously mentioned in Step 22S of holding the end section of the diseased or defective site of the intestinal tract and in Step 23S of cutting off the end section of the diseased or defective site of the intestinal tract and closing the cut-end section of the remainder of the intestinal tract by purse-string-like linear-stapling suturing: cutting off straight in the transverse direction the other of the near end sections of said diseased or defective site T3 and closing the other cut-end section of the remainder of the intestinal tract by purse-string-like linear-stapling suturing (Step 24S: cutting off other end section of diseased or defective site of intestinal tract and closing the corresponding cut-end section of the remainder of the intestinal tract by purse-string-like linear-stapling suturing).

In the steps of cutting off the respective end sections of the diseased or defective site of the intestinal tract (Step 23S) and closing the respective end sections of the remainder of the intestinal tract by purse-string-like linear-stapling suturing (Step 24S), each of the suture staples 511 is formed by being pressed, by the front-end/rear-end linear staple-driver 556, between the staple-forming grooves 544a, which are the lower face of the staple guide 544 of the upper jaw 504, and by the front-end/rear-end linear staple-driver 556, 557, in order to close the front-end/rear-end sections C1/C2 of the intestinal tract on the anvil-assembly side (in the direction of the mouth) T1 and on the head-assembly side (in the direction of the anus) T2 by purse-string-like linear-stapling suturing straight in the transverse direction. Each blade edge of the pair of said (front-end/rear-end) linear cutters 558, 559 cuts off straight in the transverse direction the respective front-end/rear-end sections C1, C2 of the diseased or defective site T3 of the intestinal tract and removes said diseased or defective site T3 from the remainder of the intestinal tract having said purse-string-like linear-stapling suturing site T1a or T2a, as if pinching said C1 or C2 from its respective outsides. Because the pair of linear cutters 558, 559 are arranged along either the left or right side so as to pass near the staple cartridge 510, it is possible to set the pair of (front-end/rear-end) linear cutters 558, 559 near their respective front-end/rear-end sections C1, C2 of the diseased or defective site T3 of the intestinal tract, and to further adjust the vertical location of the end effector 503, so that the respective two end sections of the diseased of defective site T3 of the intestinal tract are effectively cut off and closed by purse-string-like linear-stapling suturing.

At this time, the diseased or defective site T3 of the intestinal tract whose two cut-end sections have been cut continues to be held between the upper jaw 504 and lower jaw 505 of the end effector 503. Also, the electric guide wire 100 of the circular anastomosis surgical stapler 1 is left, without being cut, and between the concave notches 558a, 559a (FIGS. 12 and 13) of each blade edge in the pair of linear cutters 558, 559.

After the completion of cutting off, and then closing by purse-string-like linear-stapling suturing, the diseased or defective site of the intestinal tract, the closing jaws of the end effector 503 of the linear cutting/stapling device 500 are withdrawn from the endoscopic hole Mb or Md (Step 25S: withdrawal of linear stapler from abdomen). At this time, the diseased or defective site T3 that has been cut off and removed from the remainder of the intestinal tract and held by the end effector 503 is removed from the abdominal cavity via the endoscopic hole Mb or Md together with the linear cutting/stapling device 500. At this stage, as shown in FIG. 7, the purse-string-like linear-stapling suturing site T1a of the intestinal tract on the anvil assembly 3 side and the purse-string-like linear-stapling suturing site T2a of the intestinal tract on the head assembly 4 side are brought together. However, the two main axes X, X0 of the anvil assembly 3 and the head-assembly side 4 almost never align with each other, being different from the condition shown in FIG. 7, so that these axes are skewed.

Also, the diseased or defective site T3 whose two end sections have been cut off and removed from the remainder of the intestinal tract is able, by using an endoscopic tool (not shown in the figures) in the endoscope 600, to be removed from the abdominal cavity via the endoscopic hole Md or Mb.

After withdrawing the linear cutting/stapling device from the abdomen 25S, the monopolar electrode 34c is galvanized via the electric guide wire 100 by switching on an electric-power source, the anvil shaft 34 is rotated by operating the anvil-shaft-rotation motor 307 of the anvil shaft, and the electric guide wire 100 is gradually taken up by the take-up unit 110. Next, the push-tube drive motor 90 forces the front of the locking portion 54 of the push tube 7 to move forward to the front of the head assembly (see FIG. 3) (at this time the front end of the locking portion 54 approaches the purse-string-like linear-stapling suturing site T1a of the intestinal tract), and the purse-string-like linear-stapling suturing site T2a of the intestinal tract on the rear end side of the anvil shaft 34 is made to contact the purse-string-like linear-stapling suturing site T1a on the head assembly 4 side (at this time, the respective main axes X, X0 of the anvil assembly 3 and the assembly 4 intersect each other, and do not align with each other as is shown in FIG. 7, so that here they are skewed. Then the purse-string-like linear-stapling suturing sites T1a, T2a (FIG. 7) of the intestinal tract on their respective sides of the anvil assembly 3 and the head assembly 4 are cauterized in order, and said respective cauterized portions are opened by the trocar 34b, after which the anvil shaft 34 is inserted into and passed via said respective cauterized portions (Step 13S: cauterization of purse-string-like linear-stapling suturing sites).

At this time, the rotation of the anvil shaft 34 that is connected to the trocar 34b prevents the branding of the purse-string-like linear-stapling suturing sites T1a, T2a of the intestinal tract that otherwise would result from the galvanization by monopolar electricity, and the cauterization and opening of T1a, T2a by the trocar 34b are successfully achieved. The opening portions of the anvil assembly 3 side and the head assembly 4 side (not shown in the figures), whose purse-string-like linear-stapling suturing sites T1a, T2a of the intestinal tract are cauterized and then opened, are stopped from bleeding, and the anvil shaft 34 (and locked portion 35) passes through said opening portion of the anvil assembly 3 side in a sticking condition, and the locking portion 54 (and push tube 7) passes through said opening portion of head assembly 4 side in a sticking condition. Then, using an endoscopic tool (not shown in the figures) in the endoscope 600, the positions of said respective cauterized opening portions are adjusted, and the front cauterized opening portions are passed in order beyond the rear end of the anvil shaft 34 (including the trocar 34b) and the locked portion 35, and the rear cauterized opening portions are passed in order beyond the locking portion 54 and the front end of the push tube 7. Under this condition, both of said cauterized opening portions of the remainder of the intestinal tracts are bound tightly with thread, which prevents foreign materials from leaking from the two portions T1, T2 of the remainder of the intestinal tracts, which also further increases the reliability of subsequent treatments.

Subsequently, the anvil assembly 3, which has been separated from the head assembly 4, is floating in an unsteady position, being inclined toward the head assembly 4, in the remainder of the intestinal tract of the body M. Under this condition, the electric guide wire 100 tries to pull the anvil assembly 3 and to connect the anvil assembly 3 to the head assembly 4. At this time, as shown in FIG. 10, by applying the anvil-attitude control system, the rear end of the trocar 34b in the anvil assembly 3 is pulled by the electric guide wire 100 and moves to inside the locking portion 54, or moves closer to inside near the front end 7a of the push tube 7, in which the rear end of the locking part 54 is mounted. Under this condition, a base point (temporally fixed point) is set at the rear end of the trocar 34b, which meets the front end 7a of the push tube 7, and the anvil-attitude control system causes the target angle of the anvil shaft 34 to approximately agree at this point in time with the angle data from the Y0-axis, the Z0-axis angle sensors 402, 403 of the head assembly 4, thereby to automatically control the way that the anvil assembly 3 is positioned (Step 14S: controlling the attitude of anvil assembly).

In the step (14S) of controlling the attitude of the anvil assembly, the observation and confirmation of the condition of the intestinal tract T is made from inside of the intestinal tract T by using a wireless endoscope 120, in addition to using an endoscope 600 from outside of the intestinal tract for that purpose.

After making the main axis (central axis) (X axis) of the anvil shaft 34 and the main axis (central axis) (X0 axis) of the head assembly 4 almost align with each other by controlling the anvil assembly attitude, as shown in FIG. 5, the take-up unit 110 pulls the electric guide wire 100 and fits the anvil shaft 34 into the locking portion 54 and then into the push tube 7, and at the same time couples/locks the locked portion 35 of the anvil shaft 34 with the locking portion 54 at the front end 7a of the push tube 7, then connects/locks the anvil assembly 3 with the head assembly 4 (Step 15S: connecting/locking the anvil assembly to the head assembly). At this time, as shown in FIG. 8, the anvil assembly 3 is connected to and locked to the head assembly 4 while maintaining a predetermined gap E, which is the gap between the anvil assembly 3 and the head assembly 4 and which almost equals the sum of the thicknesses of the remainders of the intestinal tract on the anvil-assembly side T1 and on the head-assembly side T2.

In the step (15S) of connecting/locking the anvil assembly to the head assembly, the observation and confirmation of said step 15S is performed from inside the remainder of the intestinal tract T2 by using a wireless endoscope 120, in addition to conducting said observation and confirmation from outside of the tract T by using the endoscope 600.

Next, by the driving operation of the staple/cutter driving motor 91 of the operating assembly 6, which forces the staple/cutter driver 42 to move forward (pushing) via the driver tube 52 and drives a number of anastomotic staples 10 and the circular (annular) cutter 45 toward the anvil assembly 3 and the lining washer 37, as shown in FIG. 8, at the same time overlapping the remainder of the intestinal tract on the anvil assembly 3 side (in the direction of the mouth or distal end) T1 and the remainder of the intestinal tract on the head assembly 4 side (in the direction of the anus) T2, so as to perform, in the transverse direction, circular anastomosis of said overlapped sections of the two portions T1, T2 of the remainder of the intestinal tract by using anastomotic staples 10, while at the same time using the tubular circular (annular) cutter 45 to cut off and remove both of the intestinal-tract parts T4, T5. Then there is performed circular anastomosis of said two cut-end sections of the remainder of the intestinal tract on the anvil assembly 3 side T1 and on the head assembly 4 side T2 (Step 16S: performing circular anastomosis of the two cut-end sections of remainder of intestinal tract), after which the two cut-end sections are thereby connected with each other, and rehabilitated again in a normal interconnected condition.

At this time, the anastomotic staples 10 are pressed between the staple-forming grooves 31b on the rear-end face of the anvil 31 and the staple-driver (driving) finger 43 in the central axis (X0) direction so that the anastomotic staples are in a condition to perform circular anastomosis of said two cut-end sections T1, T2 of the remainder of the intestinal tract, and the blade edge of the circular (annular) cutter 45 is pressed so that said blade edge breaks into the rear-end face of the lining washer 37 in the anvil 31, and cuts off in a circular shape the two intestinal tracts T4, T5 at their respective purse-string-like linear-stapling suturing sites T1a, T2a, with said two cut intestinal tracts T4, T5 being left inside the circular (annular) cutter 45.

After the completion of circular anastomosis of the two cut-end sections of the remainder of the intestinal tract, the insertion body 2, including the connected/locked condition of the anvil head assembly 3 and the head assembly 4, of the circular anastomosis surgical stapler 1 is withdrawn from the anus Ma (Step 17S: withdrawal of circular anastomosis surgical stapler from intestinal tract). At this time, the intestinal-tract parts T4, T5 that have been left inside the circular (annular) cutter 45 are removed from the anus together with the circular anastomosis surgical stapler 1.

As stated above, according to Embodiment 1 of the present invention, the insertion body 2 of the circular anastomosis surgical stapler 1 is inserted via a natural orifice of the body into the hollow organ T that has a diseased or defective site T3, and the anvil assembly 3 is separated from the head assembly 4 by the distance between the respective the front end C1 and the rear end C2 of the diseased or defective site T3 in the hollow organ T. Under this condition, the linear stapler 500 that is inserted via an endoscopic hole Mb or Md, the diseased or defective site T3 is cut off and removed from the remainder of the hollow organ T by a procedure outside of said hollow organ T, with said procedure observed via the endoscope 600 inserted via another endoscopic hole Md or Mb. At the same time, the respective two cut-end sections of the remainder of the hollow organ T are closed by purse-string-like linear-stapling suturing, after which the circular anastomosis surgical stapler 1 automatically or semiautomatically performs circular anastomosis of the two cut-end sections T1, T2 of the remainder of the hollow organs by a procedure inside the hollow organ T. Therefore, by eliminating the existing need for a large-scale abdominal incision and by reducing the operating time and invasiveness of surgical procedures, it is possible to provide a system and method for use in NOTES that is improved in regard to the operability of the surgical devices and the reliability and economic efficiency of the operation.

As another implementation form of the invention, each member, mechanism sand configuration of the circular anastomosis surgical stapler 1 and the linear stapler 500 can be changed as desired. For example, although not shown in the figures, the pinion/rack mechanism of the upper-jaw opening/closing mechanism 530 can be replaced by a motor-driven rotating nut/screw mechanism that opens and closes an upper jaw 504 of a parallel type. As another example, an inclined opening-and-closing mechanism that rotatably supports the rear end of the upper-jaw support shaft and opens the front side of the upper jaw can be also employed freely with this invention.

In this invention, the motor-driven rotating nut/screw mechanism employed in the push-tube drive mechanism 64 and the staple/cutter driver (driving) mechanism 66 of the circular anastomosis surgical stapler 1 is also freely replaceable by a microlinear actuator such as a heretofore-known small motor-driven cylinder that is commercially supplied by the name of "ROBO Cylinder" and the like.

Figure 18:
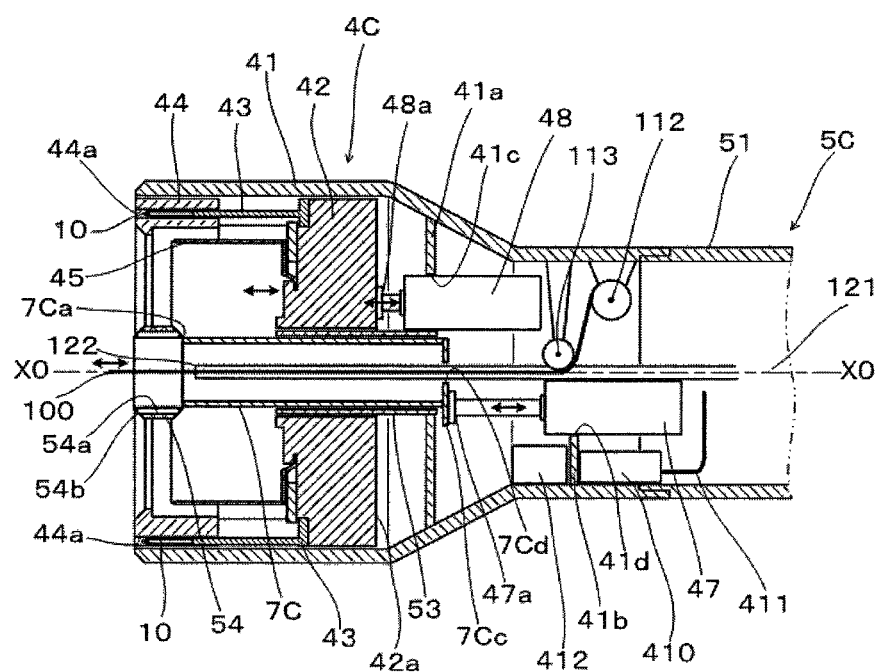
FIG. 18 is a vertical-section diagram of the head assembly of the circular anastomosis surgical stapler, showing the main configuration concept of a modified mode of Embodiment 1 of the present invention.
Figure 19:
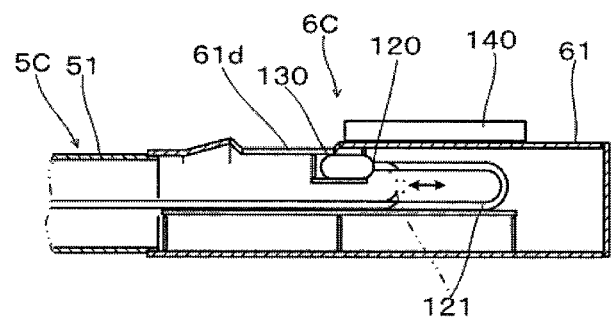
FIG. 19 is a vertical-section diagram showing the main configuration concept of the operating assembly of the circular anastomosis surgical stapler shown in FIG. 18.

FIG. 18 is a vertical-section diagram that shows a transformation implementation form of Embodiment 1, including the main configuration concept of a head assembly 4C of a circular anastomosis surgical stapler. FIG. 19 is a vertical-section diagram showing the main configuration concept of an operating assembly 6C of the circular anastomosis surgical stapler shown in FIG. 18. FIGS. 18 and 19 correspond, respectively, to FIGS. 3 and 6 in the original mode, so that the same alphanumeric references used in FIGS. 3 and 6 are also used in FIGS. 18 and 19 when the functions of the corresponding members of the two modes (original mode and transformation implementation form) are same even, if their shapes are partly different.

As shown in FIG. 18, the head assembly 4C of the circular anastomosis surgical stapler in the transformation implementation form of Embodiment 1 differs from the head assembly 4 of the circular anastomosis surgical stapler 1 in the original mode of Embodiment 1. Not included inside the head assembly 4 in the original mode are the following, which are included in the head assembly 4C of the transformation implementation form: a push-tube drive mechanism 47, which causes the push tube 7C to move forward/rearward; a locking portion 54 that is formed at the front end 7Ca of the push tube 7C and that couples/decouples the anvil assembly 3 to the head assembly 4s; a staple/cutter driver (driving) mechanism 48, that makes the staple/cutter driver 42 forward/rearward; a take-up unit 112, which takes-up/releases the thin wire guide (electric guide wire) 100; a guide roller 113; a wireless transmitter/transceiver 410, including an antenna 411, for communicating control signals between the driving mechanisms/units for the above-mentioned members and the operating assembly 6C; a battery 412 as a power source for said mechanisms/units. In other respects, those two modes do not differ.

In this transformation implementation form, microlinear actuators such as said small motor-driven cylinders can be applied to the push-tube drive mechanism 47 and the staple/cutter driver (driving) mechanism 48, and actuators for those mechanisms are fixed respectively at the actuator mounting holes 41c, 41b of the brackets 41a, 41b located on the head outer casing 41; the rod ends 47a, 48a (of the microlinear actuator) that move forward/rearward are fixed at the respective rear-end surfaces 7Cc, 42a of the push tube 7C and the staple/cutter driver 42. The push tube 7C and the staple/cutter driver 42 move forward/rearward by receiving forward/rearward driving power from the respective rod ends 47a, 48a.

Because of the configuration of the head assembly 4C in the modified implementation form, drive units for the push-tube drive mechanism 64, the staple/cutter driver (driving) mechanism 66, and the take-up unit 110 installed in the operating assembly 6 of the circular anastomosis surgical stapler 1 in Embodiment 1 can all be eliminated, and drive-unit connecting members—such as the connecting pipe 53, the push tube 7, the driver tube 52, and the electric guide wire 100—that connect those drive units and the head assembly 4 by being inserted and passing inside the support shaft 5, also can all be eliminated. Therefore, the configuration of the operating assembly 6C and the support shaft 5C are simplified substantially, and it is possible to provide a system and method for use in NOTES that is improved in operability and economic efficiency of the surgical devices used.

More specifically, as shown in FIG. 19 regarding the operating assembly 6C of the circular anastomosis surgical stapler in this transformation implementation form, only the wireless endoscope 120 is accommodated in the operating assembly 6C, and all the other inner functioning members are removed. As for the support shaft 5C, as shown in FIGS. 18 and 19, only an insertion-tube body 121 is inserted into the support shaft 5C, and all the other drive-portion connecting members are eliminated. Hence, the operating assembly 6C and the support shaft 5C in the circular anastomosis surgical stapler of this transformation implementation form differ distinctly from those of the original mode, resulting in significant simplification and a lighter weight.

Embodiment 2

Figure 20:
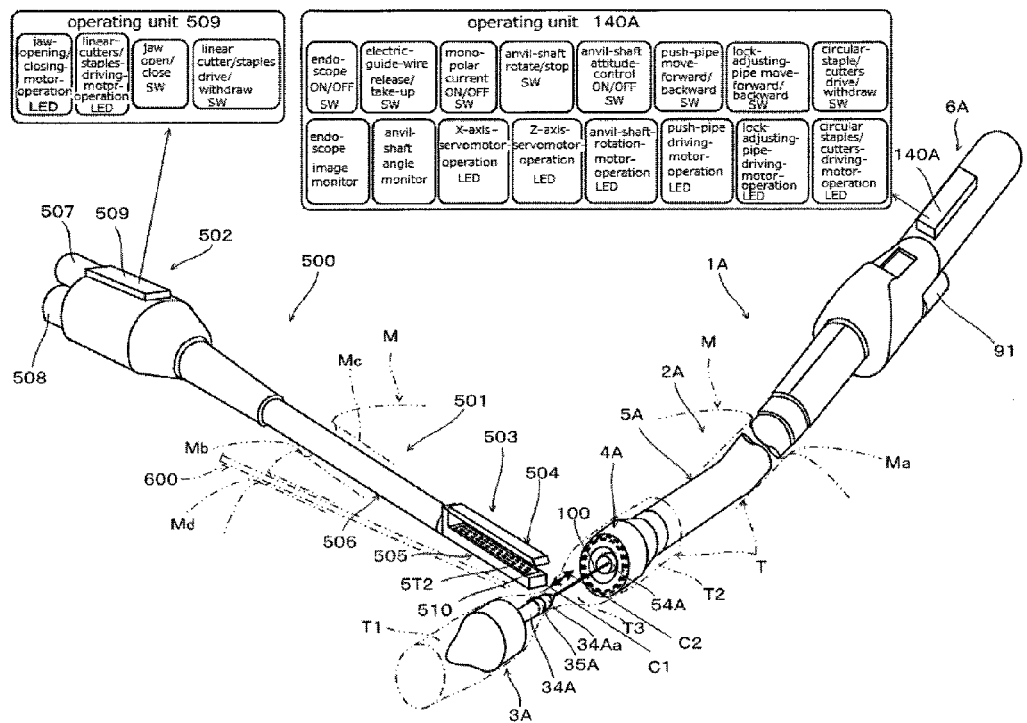
FIG. 20 is a conceptual diagram of the system for use in NOTES, showing the main configuration concept in another mode (Embodiment 2) for carrying out the present invention.
Figure 21:
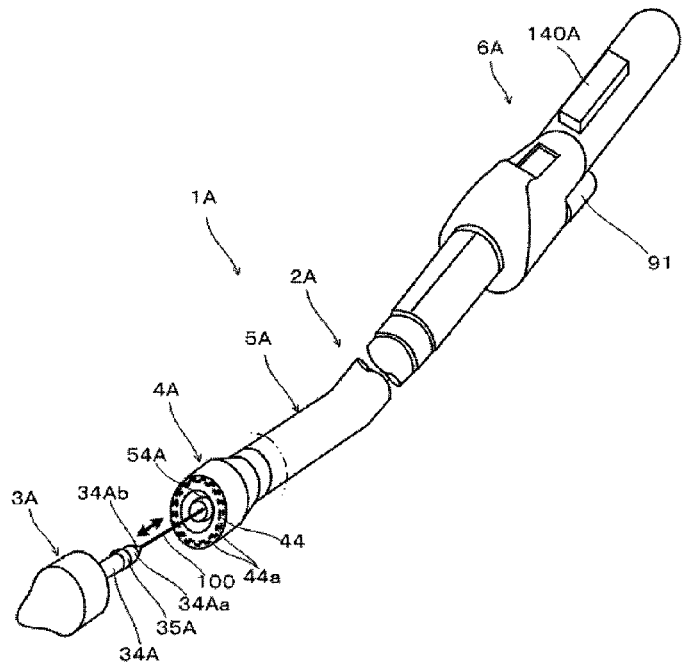
FIG. 21 is a perspective diagram showing the main configuration concept of the circular anastomosis surgical stapler of Embodiment 2.
Figure 22:
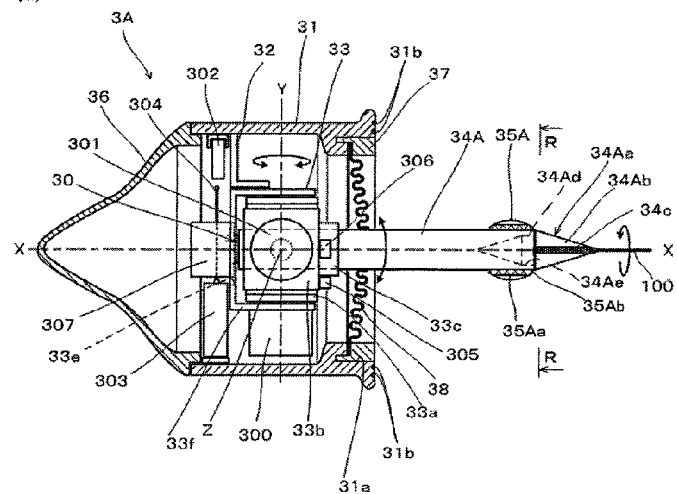
FIG. 22(*a*) is a vertical-section diagram showing the configuration concept of the anvil assembly shown in FIG. 21; 22(*b*) is a cross-sectional diagram taken along the section lines R-R shown in 22(*a*).
Figure 22:
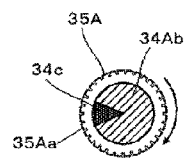
Figure 23:
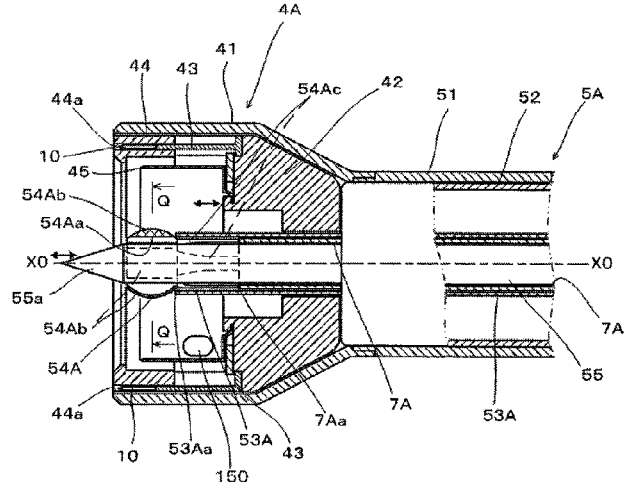
FIG. 23(*a*) is a vertical-section diagram showing the configuration concept of the head assembly shown in FIG. 21; 23(*b*) is a cross-sectional diagram taken along the section lines Q-Q shown in 23(*a*).
Figure 23:
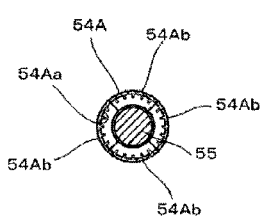
Figure 24:
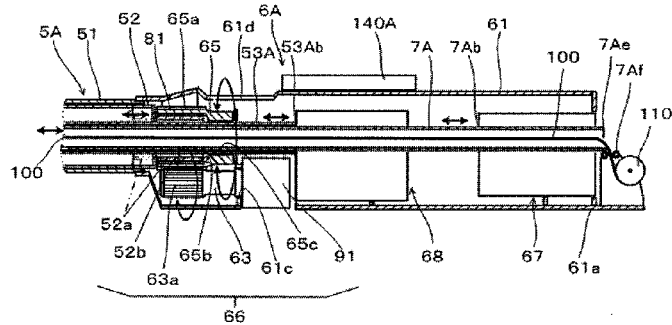
FIG. 24 is a vertical-section diagram showing the main configuration concept of the operating assembly shown in FIG. 21.

FIG. 20 is a conceptual diagram of a system for use in NOTES, showing the main configuration concept in the implementation form of Embodiment 2 of the present invention. FIG. 21 is a perspective diagram of the circular anastomosis surgical stapler 1A of Embodiment 2, showing the main configuration concept. FIG. 22(a) is a vertical-section diagram of the anvil assembly 3A shown in FIG. 21, showing the configuration concept, and FIG. 22(b) is a cross-sectional diagram taken along the section lines R-R shown in FIG. 22(a). FIG. 23(a) is a vertical-section diagram of the head assembly 4A shown in FIG. 21, showing the configuration concept, and FIG. 23(b) is a cross-sectional diagram taken along the section lines Q-Q shown in 23(a). FIG. 24 is a vertical-section diagram of the operating assembly shown in FIG. 21, showing the main configuration concept. FIG. 25 is a vertical-section diagram of the anvil assembly 3A and the head assembly 4A when coupled with each other and inserted into an intestinal tract (hollow organ) T. FIG. 26 (continuing the condition shown in FIG. 25) is a vertical-section diagram showing the anvil assembly 3A decoupled from the head assembly 4A, with a diseased or defective site T3 of the intestinal tract being cut off while at the same time the respective cut-end sections of said remainder of the intestinal tract are being closed by purse-string-like linear-stapling suturing using the linear cutting/stapling device. FIG. 27 (continuing the condition shown in FIG. 26) is a vertical-section diagram showing that an acute part 34Ab on which a trocar is formed is being pulled by the electric guide wire 100 (galvanized by monopolar electricity) and separated from the anvil shaft 34A, while cauterizing and penetrating, in order, the purse-string-like linear-stapling suturing sites T1a, T2a of the remainder of the intestinal tract on the anvil assembly 3A side T1 and on the head assembly 4A side T2, then being pulled further rearward inside the head assembly 4A. FIG. 28 (continuing the condition shown in FIG. 27) is a vertical-section diagram showing that the anvil-assembly connecting aid 55 being inserted into the push tube 7A from the rear end of the operation assembly 6A is pushed forward together with the head assembly 4A, coming close to the rear end of the anvil shaft 34A. FIG. 29 (continuing the condition shown in FIG. 28) is a vertical-section diagram showing that the anvil-assembly connecting aid 55 moves rearward in the push tube 7A and, at the same time, the lock-adjustment tube 53A moves forward and the locking portion 54A closes itself and couples to the locked portion 35A of the anvil shaft 34A. FIG. 30 (continuing the condition shown in FIG. 29) is a vertical-section diagram showing that the push tube 7A moves back to be locked with the anvil shaft 34A, and the anvil assembly 3A is pulled to a predetermined position to be coupled with the head assembly 4A. Also, all the attached diagrams here are conceptual diagrams showing the main configuration concepts expressed at NTS scale, and especially in FIGS. 22, 23, 25-30, the radial direction is enlarged compared to the axial direction to make it easier to see inside these configurations.

In the system for use in Embodiment 2, in order to increase the reliability of the connection between the anvil assembly 3A and the head assembly 4A, only the connection mechanism and related members of the circular anastomosis surgical stapler 1A differ from those of Embodiment 1. The linear stapler 500 and other configurations are not changed. Thus, the same alphanumeric reference characters used in the figures for Embodiment 1 are also used in the figures for Embodiment 2 when the functions of the corresponding members in the two embodiments are same even if their shapes are partly different. Also, duplicate explanations are omitted here, though the configurations that differ from those of Embodiment 1 are explained.

As shown in FIGS. 20 and 21, the circular anastomosis surgical stapler 1A of Embodiment 2 comprises, from front to rear: (a) an anvil assembly 3A that has an anvil shaft 34A concentrically formed so as to protrude at the rear end of the anvil assembly 3A; (b) a head assembly 4A that is positioned opposite to the anvil assembly 3A and that has (1) one or more of annular rows of staples (anastomotic staples) (hereinafter "anastomotic staples") 10 for use in circular anastomosis of the two cut-end sections of the remainder of the hollow organ T, and (2) a circular (annular) cutter 45 (see FIG. 23) for cutting off in the cylindrical direction a specific section of a hollow organ T; (c) an insertion body 2A that has a long, flexible support shaft 5A that is connected to the head assembly 4A; (d) a coupling (engaging) mechanism equipped with a locked portion 35A on the anvil shaft 34A and a locking portion 54A on the head assembly 4A, detachably coupled with each other; and (e) an operating assembly 6A that is connected to the rear end of the insertion body 2A and that controls the locking/unlocking of the coupling mechanism, the driving of the anastomotic staples 10 and the circular (annular) cutter 45, and other operations.

As shown in FIG. 22(a), the anvil assembly 3A has the same configurations as the anvil assembly 3 of Embodiment 1, except for one specific portion to be mentioned below.

The anvil shaft 34A of Embodiment 2 is formed in the anvil 31 and along the main axis (central axis) (X axis) of the anvil 31, and an acute part 34Aa that is equipped with a trocar 34Ab is connected detachably to the rear end of the anvil shaft 34A. An acute-part coupling hole 34Ae is formed at the rear face of the anvil shaft 34Aa to connect the acute part 34Aa with the anvil shaft 34A. The acute part 34Aa is made of an insulating material such as resin and includes: a small-diameter connecting-shaft 34Ad of at the front end, to be inserted into and coupled with an acute-part coupling hole 34Ae of the anvil shaft 34A; and a trocar 34Ab that has at its rear end a monopolar electrode 34c similar to that of Embodiment 1. The anvil shaft 34A and the acute-part coupling hole 34Ae are formed so as to have almost the same diameter and to be connected with each other, with the rear-end portion of the trocar 34Ab where the monopolar electrode 34c is located being sharp in order to easily penetrate the purse-string-like linear-stapling suturing sites of the remainder of the hollow organ (intestinal tract) T1a, T2a (see FIG. 26), as will be further described below. Why the monopolar electrode 34c is provided in the trocar 34Ab even if the acute part 34Aa is made of insulating material is explained below.

Also, as in Embodiment 1, the anvil shaft 34A that is coupled with the acute part 34Aa that has the trocar 34Ab is rotatably supported by the anvil-shaft support 33c and is connected to a rotation means, as is explained below, and the anvil shaft 34A is rotated by said rotating means when the monopolar electrode 34c is galvanized by monopolar electricity.

The electric guide wire (thin wire guide member) 100 that extends from the operating assembly 6A to the head assembly 4A and that is inserted via the inside of the push tube 7A, is connected to the monopolar electrode 34c at the rear end of the trocar 34Ab of the acute part 34Aa. The electric guide wire 100 has the following three functions when circular anastomosis of the two cut-end sections of the remainder of the hollow organ T is performed: (a) a retracting function to retract the acute part 34Aa into the head assembly 4A by separating the acute part 34Aa from the rear end of the anvil shaft 34A, while the operating assembly 6A takes up the electric guide wire 100, as described later; (b) an auxiliary function to separate and unlock the anvil assembly 3A from the head assembly 4A by releasing the electric guide wire 100; and (c) a function of opening a cauterization site, whereby the monopolar electrode is galvanized by monopolar electricity so that the anvil shaft 34 penetrates the respective purse-string-like linear-stapling suturing sites T1a, T2a of the two portions—T1 on the anvil-assembly side and T2 on the head assembly 4A side—of the remainder of the hollow organ (intestinal tract), and then, being pulled to the head-assembly side 4, sequentially cauterizes the respective purse-string-like linear-stapling suturing sites T1a, T2a of the two portions T1, T2 of the remainder of the hollow organ, after which a cauterization opening is formed by the insertion of trocar 34b. The insulator 34a stops the flow of monopolar electricity between the anvil shaft 34A and anvil assembly 3A.

Also, a locked portion 35A is formed on the outer surface of the anvil shaft 34A at the front near the acute part 34Aa. The locked portion 3A has a convex shape such as a sphere, and is coupled to and locked with the locking portion 54A that is at the front end of the push tube 7A in the head assembly 4A, as is described further below. The detail of the function of the coupling mechanism provided with the locked portion 35A and the locking portion 54A is further described below.

The anvil-assembly-attitude control mechanism 30 is the same as the one in Embodiment 1, and therefore a detailed explanation of said mechanism is omitted here.

As shown in FIG. 23(*a*), the head assembly 4A in Embodiment 2 is the same as the one in Embodiment 1, except for the coupling/locking mechanism (explained later).

The push tube 7A and the lock-adjusting pipe 53A are inserted concentrically in the center of the shaft support 5A from the operating assembly 6A (see FIG. 24) and the front end of the two pipes 7Aa and 53Aa so as to reach the inner center of the head assembly 4A.

The staple/cutter driver 42 that is connected to the front end of the driver tube 52 of Embodiment 2 is installed so as to be slidable back and forth on the outer surface of the lock-adjusting pipe 53A (see FIG. 24).

A locking portion 54A, which detachably captures and locks the locked portion 35A of the anvil shaft 34A, is formed at the front end 7Aa of the push tube 7A of Embodiment 2, (see FIGS. 23 and 25). The locking portion 54A is installed in the center of the head assembly 4A, and is composed of: (1) a split-capture part 54Ab that is divided into at least three parts in the circumferential direction and formed to have a concave shape, such as that of an almost-hollow sphere, and to be able to detachably capture the locked portion 35A that is on the anvil shaft 34A; (2) flexible supports 54Ac (three members in this example), installed at the front end 7Aa of the push tube 7A, that flexibly support the split-capture part 54Ab in freely bending and expanding to increase the radius of the split-capture part 54Ab from the central axis (main axis). The flexible supports 54Ac are made of spring steel or a shape-memory alloy having suitable stiffness and high mechanical strength and are formed so as to have an almost circular cylindrical shape of sufficient width to have adequate mechanical strength (see FIG. 28).

Due to the operation of the operating assembly 6A, the push tube 7A captures, by the locking portion 54A, the locked portion 35A on the anvil shaft 34A of the anvil assembly 3A, and makes the acute part 34Aa retract into itself and then connects the anvil assembly 3A to the head assembly 4A. In contrast, and as the opposite operation, the push tube 7A pushes forward the anvil shaft 34A and releases the locked portion 35A on the anvil shaft 34A from the locking portion 54A on the front end 7Aa of the push tube 7A, and by being installed inside of the lock-adjustment tube 53A, moves slidably back and forth so that the anvil assembly 3A is separated from the head assembly 4A (see FIGS. 24 and 25).

The push tube 7A is open after passing via the inside of the operating assembly 6A to the rear opening 7Ae, and the electric guide wire 100 is inserted via the inside of the push tube 7A from the operating assembly 6A to the support shaft 5A. The acute part 34Aa, separated from the rear end of the anvil shaft 34A, is pulled by the electric guide wire 100 and withdrawn from the rear opening 7Ae (see FIGS. 22, 25, and 27).

In the push tube 7A of Embodiment 2, an anvil-assembly connecting aid 55 that assists the reconnection of the anvil assembly 3A with the head assembly 4A is inserted so as to be able to be withdrawn from the rear-end opening 7Ae of the push tube 7A, and the anvil-assembly connecting aid 55 comprises a trocar-like acute part 55*a* whose front end is formed like a trocar and passes via the inside of the split-capture part 54Ab of the locking portion 54A, and a flexible shaft member 55*b* that is connected to the trocar-like acute part 55*a*.

The lock-adjustment tube 53A of Embodiment 2 is installed onto the outer surface of the push tube 7A, being free in its back-and-forth movement, and the front end 53Aa moves forward to contact the rear end of the split-capture part 54Ab so that the flexible support 54Ac is pressed from the outside and closes the split-capture part 54Ab in the decreasing-diameter direction (see FIGS. 23, 25-27, and 29). In contrast, and as the opposite operation, the front end 53Aa moves rearward in order to open mainly the split-capture part 54Ab in the increasing-diameter direction (see FIG. 28).

In this way, the coupling mechanism to connect the anvil assembly 3A with the head assembly 4A comprises the locked portion 35A at the rear end of the anvil shaft 34A, the locking portion 54A at the front end 7Aa of the push tube 7A, and the lock-adjustment tube 53A. As shown in FIG. 30 and FIG. 8, and as described later, this coupling mechanism is required to have: (1) a function of maintaining the anvil assembly 3A in said connection of the anvil assembly 3A, having the predetermined gap of E, as described later, while connected to the head assembly 4A when there is performed circular anastomosis of the two cut-end sections of said remainders of the hollow organs T1, T2, which included the diseased or defective site T3, and (2) an angle-positioning function that that makes it possible for the shaft attitudes around the principal axes (central axes) of the anvil assembly 3A and the head assembly 4A to be specified so that the staple accommodation slots 44*a* of the staple cartridge in the head assembly 4A and the grooves for forming staplers 31*b* in the rearward face of the anvil 31 face each other appropriately.

For this purpose, said coupling mechanism can be the same as the existing configuration in various implementation forms, e.g., in Patent Document 1. As one example, this Embodiment 2 has a spline mechanism in which the rotation is restrained around the principal axes (central axes) (X-axis and X0-axis) and moves slidably in the direction of the principal axes (central axis). That is, as shown in FIGS. 23(*a*) and 23(*b*), a concave-shaped spline (female spline tooth) 54Aa is formed on the cylindrical inner surface of the locking portion 54A, and as shown in FIGS. 22(*a*) and 22(*b*), a convex-shaped spline (male spline tooth) 35Aa is formed on the outer surface of the locked portion 35A, so that those two splines are coupled with each other. By this configuration, the shaft attitudes around the principal axes (central axes) of the anvil assembly 3A and the head assembly 4A are prescribed so that the staple accommodation slots 44*a* of the staple cartridge in the head assembly 4A and the grooves for forming staplers 31*b* in the rearward face of the anvil 31 face each other appropriately.

The configurations of the push tube 7A and the connection mechanism are, together with the configuration of the anvil assembly 3A, among the important and unique characteristics of the present invention. The functions of those configuration will explained in detail below.

The peripheral corner portions of the front edge and rear edge of the locked portion 35A and the locking portion 54A are chamfered, and become smooth, inclined faces so that the cauterized openings of the respective purse-string-like linear-stapling suturing sites T1*a*, T2*a* of the remainder of the hollow organs T1, T2 are easily penetrated, and so that the locked portion 35A is easily mated and coupled with the locking portion 54A.

Due to the coupling mechanism in Embodiment 2, when the anvil assembly 3A is reconnected to the head assembly 4A after the diseased or defective site T3 is cut off and removed from the remainder of the hollow organ, the back-and-forth movement of the lock-adjusting pipe 53A, together with the forward movement of the split-capture part 54Ab, opens and closes the split-capture part 54Ab that is located at the front end of the push tube 7A, capturing the locked part 35A of the anvil shaft 34 and rolling back the push tube 7A. The anvil assembly 3A is pulled toward the head assembly 4A side, and at the same time the anvil assembly 3A can be easily locked to the head assembly 4A. Hence, the reliability of the coupling mechanism between the anvil assembly 3A and the head assembly 4A is improved.

As shown in FIGS. 21, 23, and 24, the shaft support 5A in Embodiment 2, comprises: (1) an outer tube 51 whose front end is connected to the head outer casing 41 of the head assembly 4A, and whose rear end is connected to the operating-assembly housing 61; (2) a driver tube 52; (3) a lock-adjustment tube 53A; and (4) push tube 7A—all of which are inserted, in order, having the same central axis and juxtaposed inside the outer tube 51. The wireless-endoscope insertion-tube body 121 and the electric guide wire 100 are inserted via the push tube 7A. The members that constitute the support shaft 5A or other members inserted inside the support shaft are all made of flexible materials, as a result of which members used for existing medical purpose devices, such as circular anastomosis surgical staplers or endoscopic instruments, can be applied.

As shown in FIG. 24, the operating assembly 6A in Embodiment 2 is provided with: (1) an operating-assembly housing 61 of an almost-circular cylinder type, connected at the front end of the outer tube 51 of the support shaft 5A; (2) a staple/cutter driver (driving) mechanism 66 that drives the anastomotic staples 10 and the circular (annular) cutter 45; (3) a push-tube drive mechanism 67 that moves the push tube 7A back and forth; and (3) a lock-adjusting-pipe drive mechanism 68 that moves the lock-adjusting pipe 53A back and forth. In this Embodiment 2, those three mechanisms are all electric-motor-driven and differ from the manual adjusting knob mechanism and the staple/cutter driving handle mechanisms described in, for example, Patent Document 1.

As is the same in Embodiment 1, the staple/cutter driver (driving) mechanism 66 of Embodiment 2 comprises: (1) a male-screw tube 52a; (2) an externally-toothed rotating nut 65; (3) an outer tooth 65a; (4) a staple/cutter driver (driving) motor 91; and (5) the staple/cutter driver shaft 63. Accordingly, a detailed explanation is omitted here.

The push-tube drive mechanism 67 and the lock-adjusting-pipe drive mechanism 68 are composed of a male-screw tube, an externally-toothed rotating nut, and a drive motor that has a pinion, as is similar to said staple/cutter driver (driving) mechanism 66.

Therefore, due to the forward and reverse rotations of the externally-toothed rotating nut driven by the push-tube drive motor or the lock-adjustment-tube drive motor (which are not shown in the figures), respectively, the push tube 7A and the lock-adjustment tube 53A, which receive the axial thrust of the male-screw tube that is screwed to the externally-toothed rotating nut, move back and forth, respectively.

An indicator that inclines back and forth along the scale marks (not shown in the figures) of an indication window 61d in response to the back-and-forth movements of the push tube 7 and that indicates the predetermined driving stroke of the staple/cutter driver 42, small members for a safety mechanism to prevent malfunction of the staple/cutter driver (driving) mechanism 66, and the above-mentioned indicators can all be configured to be same as in many embodiments of the existing circular anastomosis surgical staplers. Accordingly, illustrations and a detailed explanation are omitted here. The above-mentioned safety mechanism engages with the indicator so that the indicator inclines backward along the scale marks (not shown in the figures), and indicates the predetermined driving stroke of the staple/cutter driver 42 when the anvil assembly 3A is coupled and locked with the head assembly 4A, maintaining a predetermined gap E similar to that of Embodiment 1 (see FIG. 8).

The predetermined value of the gap E between the anvil assembly 3A and the head assembly 4A at the time of locking of those assemblies 3A, 4A is also almost equal to the sum of the thicknesses of the remainder of the hollow organ on the anvil-assembly side T1 and the head-assembly side T2. The F area in FIG. 30 of Embodiment 2 is shown in the same way as that of Embodiment 1 in FIG. 8.

As shown in FIG. 24, in this Embodiment 2 the push tube 7A passes via the lock-adjustment drive mechanism 68 and the push-tube drive mechanism 67, and is opened up to the rear opening 7Ae. Also, a take-up unit 110 that takes up or releases the electric guide wire 100 due to the operation of a motor (not shown in the figures) is provided outside of the rear end 61a of the operating assembly 6A. An electric guide wire 100 is connected to the monopolar electrode 34c at the rear end of the trocar 34Ab of said acute part 34Aa, and it passes via the inside of the push tube 7A from the head assembly 4A to the rear opening 7Ae of the push tube 7A, being withdrawn through a pair of the roller-guide aperture 7Af installed near the rearward opening 7Ae of the push tube 7A.

As a transformation implementation form, instead of a mechanical control configuration composed of an existing safety mechanism, indicators, and so on, a safety/electronic control configuration can be employed. The safety/electronic control configuration includes, e.g., a take-up detecting sensor (not shown in the figure) for the take-up unit 110, wherein the lengths of the two-way movements of the electric guide wire 100 that is connected to the anvil assembly 3A are measured by the take-up detecting sensor, and therefore both the predetermined gap E between the anvil assembly 3A and the head assembly 4A and the predetermined stroke of the anastomotic staples 10 are displayed on a monitor (not shown in the figure), and the safety/electronic control configuration can be applied by introducing a motor-drive interlock such as a staple/cutter driving motor 91.

The modified Embodiment 2 eliminates the need for a complicated mechanical control configuration that uses existing safety mechanisms, indicators, and so on, and the structure of the operating assembly 6A can be simplified.

A capsule endoscope 150 is accommodated inside the head assembly 4A, as shown in FIG. 23a.

The capsule endoscope 150 in Embodiment 2 consists of: (1) an embedded pill-type box made from resin, having an approximate outer diameter of 9 mm-11 mm and a length of 23 mm-26 mm: (2) an ultracompact capsule-type CCD camera or CMOS imaging device (neither is shown in the figures); (3) one or more light-emitting diodes (LEDs); (4) a microbattery or power-transmission source; and (5) a coil for controlling the attitude of the capsule endoscope 150. As for the capsule endoscope, several devices are already in practical use, such as the PillCam SB of Given Imaging Ltd., the NORIKA and the Sayaka of RF Co., Ltd., and similar devices described in Unexamined Patent Application Republication WO2004/112593 have been proposed. Thus, a detailed explanation about the capsule endoscope 150 is omitted here.

By employing for the capsule endoscope 150 one or more light-emitting diodes (LEDs), which consumes little electric power, and a CMOS imaging device, it is possible to use a microbattery for electric power. The CMOS is advantageous in that it consumes little power and in that the system is on a chip.

The operating assembly 6A accommodates air/cleansing-water supply sources, a utility-control device for the air/cleansing-water supply and blood/water suction operations, and a wireless endoscope unit for the wireless endoscope. The wireless endoscope unit has a control knob to actuate the capsule endoscope 150, along with a wireless transceiver to communicate control signals to the operating assembly (neither is shown in the figure).

The image-picture data signals from the imaging device are transmitted via the wireless transceiver 131 using microwaves or wireless periodicity applying some kind of digital or analog modulation technique. For example, an FSK (frequency shift keying) modulation technique can be used to transmit the digital images via a wireless channel. Some configuration elements, such as the image sensor and irradiation source, are single-use battery-operated units. The capsule endoscope 150 is superior in operability to a conventional wireless endoscope in that the operation of the capsule endoscope 150 is simpler.

As shown in FIG. 20, an operating unit 140A is provided at an upper place of the operating-assembly housing 61, and includes at least: an endoscope monitor; an anvil-shaft-angle monitor; a lock-adjustment-tube-drive motor-operation LED; a staple/cutter-driver motor-operation LED; an endoscope ON/OFF SW (operating switch of the capsule endoscope 150); an electric-guide-wire release/take-up SW (for the take-up unit 110: an electric guide wire 100 release/take-up switch); a monopole ON/OFF SW (monopole current ON/OFF switch); an anvil-shaft rotation/stop SW; an X-axis-servomotor-operation LED; a Y-axis-servomotor-operation LED; an anvil-shaft-rotation motor-operation LED; an anvil-shaft-attitude-control ON/OFF SW; a push-tube forward/rearward SW; a lock-adjustment-tube forward/rearward SW; a staple/cutter ejection/retraction SW; a wireless transmitter/transceiver 303 installed in the anvil assembly 3A, wherein the operating unit 140A has a wireless transceiver to communicate with the wireless transmitter/transceiver 303 in the capsule endoscope 150; and a battery.

The circular anastomosis surgical staplers 1A are wirelessly operated by the operating unit 140A, as will be further described below.

The motor-driven rotating nut/screw mechanism employed in the push-tube drive mechanism 64, as well as the lock-adjustment-tube drive mechanism 68 and the staple/cutter driver (driving) mechanism 66, of the circular anastomosis surgical stapler 1A are all also freely replaceable in this invention by microlinear actuators such as heretofore-known small motor-driven cylinders, including the ROBO Cylinder and so on, that are commercially available.

Figure 31:
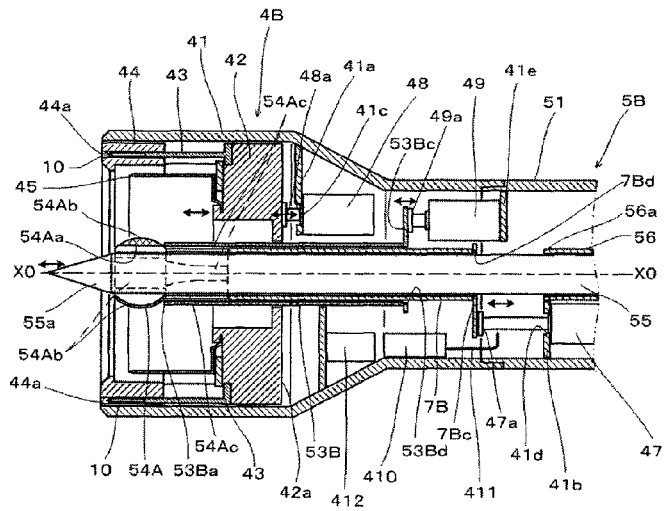
Figure 31:
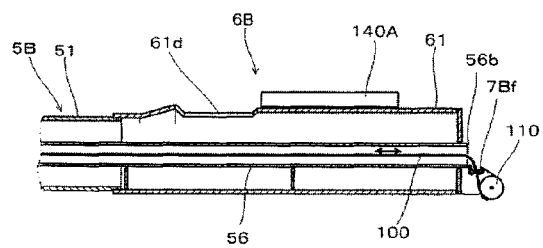

FIG. 31(*a*) is a vertical-section diagram showing the main configuration concept of the head assembly 4B in the circular anastomosis surgical stapler of the transformation implementation form in Embodiment 2 of the present invention. FIG. 31(*b*) is a vertical-section diagram showing the main configuration concept of the operating assembly 6B of the circular anastomosis surgical stapler shown in FIG. 31(*a*). FIGS. 31(*a*) and 31(*b*) correspond, respectively, to FIGS. 22 and 24 in the original mode. Therefore the same alphanumeric reference characters shown in FIG. 22 and FIG. 24 are used in FIGS. 31(*a*) and 31(*b*) when the functions of the corresponding members in the two implementation forms (the original and the transformation implementation form) are the same, even if their shapes are partly different.

The head assembly 4B of the circular anastomosis surgical staplers in the transformation implementation form differs from the head assembly 4A of the circular anastomosis surgical stapler in said Embodiment 2, inasmuch as the following parts, which in the transformation implementation form are in the head assembly 4B, are not in the head assembly 4A in the original mode: the push-tube drive mechanism 47 that moves the push tube 7B forward/backward so as to couple with and decouple from the anvil assembly 3A and the head assembly 4B; the staple/cutter driver (driving) mechanism 48 that moves the staple/cutter push members 42 forward and backward; the lock-adjustment-tube drive mechanism 49 that moves the lock-adjustment tube 53*b* forward and backward; the wireless transmitter/transceiver 410, including the antenna 411, that communicates control signals between the driving mechanisms/unit for the above-specified members and the operating assembly 6B; the battery 412, which is the power source for said mechanisms/unit. In other configurations, there is no difference between these two implementation forms. Also, in this transformation implementation form, a part of each of the push-tube drive mechanism 47 and the lock-adjustment-tube drive mechanism 49 are arranged in the shaft support 5B and near the connection with the head assembly 4B.

In this transformation implementation form, microlinear actuators such as a small motor-driven cylinder can be applied to the push-tube drive mechanism 47, the staple/cutter driver (driving) mechanism 48, and the lock-adjustment-tube drive mechanism 49. Actuators for those mechanisms are fixed, respectively, at the actuator mounting holes 41*d*, 41*c* and at the front face of the bracket 41*e*. The rod ends 47*a*, 49*a*, 48*a*, which move forward/backward, are fixed, respectively, to the end members 7Bc, 53Bc at the rear-end openings 7Bd, 53Bd of the push tube 7B lock-adjustment tube 53B, respectively, and to the rear end 42*a* of the staple/cutter driver 42. The push tube 7B, the staple/cutter driver 42, and the lock-adjustment tube 53B move forward/backward along the main axis (central axis) (X0 axis) by receiving driving power from the respective rod ends 47*a*, 48*a*, 49*a* of the microlinear actuators.

Because of the configuration of the head assembly 4B in the transformation implementation form, drive units for the push-tube drive mechanism 67, staple/cutter driver (driving) mechanism 66, and lock-adjustment-tube drive mechanism 68—all in the operating assembly 6A of the circular anastomosis surgical staplers 1A—can be eliminated, and drive-unit connecting members, such as the push tube 7A, driver pipe 52, and lock-adjustment tube 53A, that connect those drive units and the head assembly 4A by being inserted into and passing via the inside of the support shaft 5A, also can be all eliminated. Therefore, in this transformation implementation form the configuration of the support shaft 5B and the operating assembly 6B are simplified substantially, and it is possible to provide a system and method for use in NOTES that is improved in regard to the operability and economic efficiency of the surgical devices used.

More specifically, as shown in FIG. 31(*b*), regarding the operating assembly 6B of the circular anastomosis surgical stapler in this transformation implementation form, only the air/cleaning-water supply sources, the utility-control device and the wireless endoscope unit are accommodated in the operating assembly 6C, and all other inner functional members are eliminated. And as shown in FIGS. 31(*a*) and 31(*b*), inside the support shaft 5B only the guide pipe 56 is extended to the rear end 56*b* via the operating assembly 6B and has the same diameter as the push tube 7B. The distal-end portion 56*a* of the guide pipe 56 is fixed at the bracket 41*b*, and all the other drive-connecting members are eliminated. Hence, the operating assembly 6B and the support shaft 5B in the circular anastomosis surgical stapler of the transformation implementation form differ distinctly from those of Embodiment 2, and significant simplification and weight reduction are attained.

A take-up unit 110 that takes up and releases the electric guide wire 100 due to the operation of a motor (not shown in the figures) is provided in the lower portion of the guide portion 7Bf. The electric guide wire 100 passes via the inside of the guide pipe 56 from the rear end 56b of the guide pipe 56 and is withdrawn from the rear end 56b by a pair of rollers 7Bf near the rear end 56b of the guide pipe 56. The acute part 34Aa that is separated from the rear end of the anvil shaft 34A is pulled by the electric guide wire 100 and withdrawn from the rear end 56b of the guide pipe 56.

FIG. 32 is a block diagram showing the main configuration concept for the anvil-assembly-attitude control system of Embodiment 2 for use in NOTES.

The anvil-assembly-attitude control system of Embodiment 2 is the same as that of Embodiment 1, except for the connection configuration of the circular anastomosis surgical staplers 1A and the use of the anvil-assembly connecting aid 55. Therefore, a detailed explanation of the configuration is omitted here.

The anvil assembly 3A is separated from the head assembly 4A (or 4B of said transformation implementation form), the diseased or defective site T3 of the hollow organ T is cut off and removed, and the two cut-end sections of the remainder of the hollow organ are closed by purse-string-like linear-stapling suturing straight in the transverse direction. After the acute part 34Aa cauterizes and penetrates said respective purse-string-like linear-stapling suturing sites T1a, T2a, the acute part 34Aa is removed from the rear end of the operating assembly 6A. At this time, the anvil assembly 3A that has been separated from the head assembly 4A (or 4B) is floating in an unsteady position (being inclined in relation to the head assembly 4A or 4B) in the remainder of the hollow organ of the body M (see FIG. 20). Under this condition, in order to reconnect the anvil assembly 3A to the head assembly 4B (or 4B), it is necessary to insert the anvil connecting aid 55 from the rear opening 7Ae of the push tube 7A (or the rear end 56b of the guide pipe 56 in said transformation implementation form), and at the same time to observe and confirm the diseased or defective site T3 of the hollow organ by using the capsule endoscope 150 or/and endoscope 600 (FIG. 20) that has been inserted via the endoscopic hole Md or Mb and through a cannula Mc, and then by operating the anvil-attitude control system, to make the head assembly 4A (or 4B) side move to the anvil assembly 3A by adjusting the angle of anvil shaft 34A so that the rear face of the anvil shaft 34A faces the front face of the head assembly 4A (or 4B).

In this way, setting a base point (temporally fixed point) at the trocar-like acute part 55a (at this time, the trocar-like acute part 55a is near the front end of the locking portion 54A) under the condition that the trocar-like acute part 55a of the anvil connecting aid 55 moves and contacts the inner surface of the acute-part coupling hole 34Ae at the rear end of the anvil shaft 34A, and the anvil-attitude control system automatically controls the attitude of the anvil assembly 3 with reference to the target angle of the anvil shaft 34A, which is specified so as to almost agree with the angle data of the head assembly 4A (or 4B) (the Y0-axis [or Z-axis]) as measured by the angle sensors 402, 403 at that time. The main axis X-axis of anvil shaft 34A and the main axis X0-axis of head assembly 4A (or 4B) almost align with each other, and then, as shown in FIG. 30, the anvil shaft 34A easily couples into the push tube 7A and a coupling/locked state can be achieved.

As described above, the circular anastomosis surgical stapler 1A of Embodiment 2 comprises: (1) an anvil-assembly-attitude control mechanism 30 that wirelessly controls the attitude of the anvil assembly 3A in relation to the anvil shaft 34A; (2) a monopolar electrode 34c on the rear end of the trocar 34Ab; (3) an electric guide wire 100 that is connected to a monopolar electrode 34c and a take-up unit 110; (4) a push-tube drive mechanism 67 that moves the push tube 7A forward and backward, presses the anvil assembly 3A forward, and separates the anvil assembly 3A from the head assembly 4A; (5) a staple/cutter driver (driving) mechanism that moves the anastomotic staples 10 and the circular (annular) cutter 45 forward and backward; (6) a lock-adjustment-tube drive mechanism 68 that makes the lock-adjustment tube 53A move forward and backward; and (7) a capsule endoscope 150 that is installed in the head assembly 4A. The entire system is controlled by a wireless electronic control that is the present invention's configuration and that most differs from that of the existing circular anastomosis surgical staplers described in said Patent Document 1 and so on.

Next is explained, referring to FIGS. 20-30, the method for use in NOTES that uses the above-described circular anastomosis surgical stapler 1A and the linear stapler 500 of Embodiment 2. For example, in the method for use in NOTES, a diseased or defective site T3 of a hollow organ such as an intestinal tract is cut off and removed, after which circular anastomosis of the two cut-end sections of the remainder of the hollow organ is performed.

FIG. 33 is a block diagram showing the main procedural steps of the method of Embodiment 2 for use in NOTES.

The method of Embodiment 2 for use in NOTES includes: Step 1S, making endoscopic hole(s); Step 2S, laparoscopic identification of the diseased or defective site of the intestinal tract, and, in this case, the intestinal tract T as the hollow organ of the body M, for example, a human, and includes the following main procedural steps.

After the step (2S) of laparoscopic identification of the diseased or defective site of the intestinal tract, the insertion body 2A of the circular anastomosis surgical stapler 1A, whose anvil assembly 3A is connected to the head assembly 4A (see FIG. 25), is inserted via a natural orifice (e.g., the anus Ma) of the human body M until the tip of the anvil assembly 3A fully passes via the diseased or defective site T3 (of the hollow organ) in the intestinal tract T (11S: insertion of circular anastomosis surgical stapler into intestinal tract). At this time, as shown in FIG. 20, the anvil assembly 3A is inserted until the monopolar electrode 34c (see FIG. 22) at the rear end of the trocar 34Ab passes near the front-end section C1 of the diseased or defective site T3 of the intestinal tract and reaches the inside of the intestinal tract on the anvil-assembly side (in the direction of the mouth) T1.

Next, the take-up unit 110 of the circular anastomosis surgical staplers 1A releases the electric guide wire 100, and the push-tube drive motor and lock-adjustment-tube drive motor move the push tube 7A and the lock-adjustment tube 53A, respectively, forward, and then push the anvil assembly 3A forward via the anvil shaft 34A in a locked condition. The lock-adjustment-tube drive motor forces the lock-adjustment tube 53A to move rearward, and the locking portion 54A opens, increasing its diameter, and releases the locked portion 35A on the anvil shaft 34A. Furthermore, due to said operations of the push-tube drive motor and the lock-adjustment-tube drive motor, the push tube 7A and the lock-adjustment tube 53A are moved back to recessed positions (see FIG. 23), after which the anvil assembly 3A is separated from the head assembly 4A and is temporarily left in the intestinal tract on the anvil-assembly side (in the direction of the mouth) T1. Under this condition, the insertion body 2 on the head assembly 4 side is gradually withdrawn, and the head assembly 4 is forced to move backward until its front end passes near the rear end C2 of the diseased or defective site T3 and reaches the inside of the intestinal tract on the head-assembly side (in the direction of the anus Ma) T2 (Step 12S: release of anvil assembly from head assembly). The separation of the anvil assembly from the head assembly is simultaneously observed and confirmed from outside the intestinal tract T by using the endoscope 600, and from inside the intestinal tract T2 by using the capsule endoscope 150 that is in the head assembly 4A.

After confirming the condition of the anvil-assembly separation by using the endoscope 600 and the capsule endoscope 150, the following steps are processed via a cannula Mc that is inserted via an endoscopic hole: Step 21S: inserting the linear stapler into the intestinal tract; Step 22S: holding one end section of the diseased or defective site of the intestinal tract; Step 23S: cutting off, and then closing by purse-string-like linear-stapling suturing, either one of the two end sections of the diseased or defective site of the intestinal tract; Step 24S: cutting off the other end section of the diseased or defective site of the intestinal tract, and then closing, by purse-string-like linear-stapling suturing, the corresponding cut-end section of the remainder of the intestinal tract; Step 25S: withdrawing the linear stapler from the abdomen. These steps are the same as the steps in Embodiment 1, and the diseased or defective site T3 of the intestinal tract T that is cut off and removed from the remainder of the intestinal tract and held by the end effector 503 is then removed together with the linear stapler 500 via said endoscopic hole Mb or Md. In this step, as shown in FIG. 26, the purse-string-like linear-stapling suturing sites T1a on the side of the anvil assembly 3A and the purse-string-like linear-stapling suturing site T2a on the side of head assembly 4A are brought together. However, the two main axes X, X0 of the anvil assembly 3 and the head-assembly side 4 are almost never aligned with each other, being different from the condition shown in FIG. 7, so that these axes are skewed.

Also, the two end sections of the diseased or defective site T3 of the intestinal tract are cut off and removed via the endoscopic hole Md or Mb by using a endoscopic tool (not shown in the figures) of the endoscope 600.

After withdrawing the linear stapler from the abdomen 25S, gradually pulling the electric guide wire 100 by the take-up unit 110, and at the same time pushing the insertion body 2A of the head assembly 4A side forward toward the anvil assembly 3A side and making the purse-string-like linear-stapling suturing site T2a of the head assembly 4A side contact the purse-string-like linear-stapling suturing site T1a of the anvil assembly 3A side (at this time, the two main axes (central axes) X, X0 of the anvil assembly 3A and the head assembly 4A, respectively, intersect, hardly becoming straight as shown in FIG. 26). Under this condition, by the switch-on operation of the electric-power source, the monopolar electrode 34c is galvanized via the electric guide wire 100, and the anvil assembly 34A is rotated by operating the anvil-shaft-rotation motor (rotary means) 307 of the anvil shaft 34A, and then the monopolar electrode 34c of the acute part 34Aa cauterizes the respective purse-string-like linear-stapling suturing sites T1a, T2a (FIG. 26) of the respective sides of the remainders of the intestinal tract on the anvil assembly 3A (in the direction of the mouth) T1 and the intestinal tract on the head assembly 4A (in the direction of the anus) T2 in order. Said respective cauterized portions are penetrated and opened by the acute part 34Aa, (Step 13S: cauterization of purse-string-like linear-stapling suturing sites).

At this time, the rotation of the anvil shaft 34 that is connected with the acute part 34Aa that has the trocar 34Ab prevents the branding of the purse-string-like linear-stapling suturing sites T1a, T2a of the two portions T1, T2 of the remainder of the intestinal tract that otherwise would result from the galvanization of monopolar electricity, and said cauterization and opening of T1a, T2a by the acute part 34Aa are done smoothly. Then the respective cauterized opening portions T1b, T2b on the respective sides of the anvil assembly 3A and the head assembly 4A are guided by the acute part 34Aa, piercing via said respective cauterized opening portions T1b, T2b, and penetrating via the locked portion 35A, the anvil shaft 34A, and the locking portion 54A. The bleeding of the respective cauterized opening portions T1b, T2b is stopped, and by using an endoscopic tool (not shown in the figures) in the endoscope 600, the two cauterized opening portions T1b, T2b are adjusted in their positions so as to be passed, in a sticking condition, via the anvil shaft 34A and the locking portion 54A, on the forward side of the rocked portion 34A and lock-adjustment tube 53A, in that order (see FIG. 27). Under this condition, by tightly binding the two cauterized opening portions T1, T2 of the remainder of the intestinal tracts with thread, it is possible to prevent foreign materials from leaking from the two portions T1, T2, and the reliability of the following treatments is further increased.

Furthermore, as shown in FIG. 27, by continuous pulling of the electric guide wire 100, the acute part 34Aa is separated from the rear end of the anvil shaft 34A and is withdrawn via the push tube 7A to outside the rear opening 7Ae (see FIG. 24) (Step 13aS: withdrawal of acute part). Also, in this step (13aS), when the circular anastomosis surgical stapler of the transformation implementation form shown in FIG. 31 is employed, the acute part 34Aa is pulled and withdrawn from inside the push tube 7B via the guide pipe to outside the rear end 56b.

Subsequently, when the anvil assembly 3A, which is separated from the head assembly 4A and is floating in an unsteady position (inclining toward the head assembly 4A or 4B) in the remainder of the hollow organ T1, is reconnected with the head assembly 4A, as shown in FIG. 28 (or FIG. 31, for the transformation implementation form), the anvil connecting aid 55 is inserted from the rear opening 7Ae of the push tube 7A in the operating assembly 6A (or rear end 56b of the guide pipe 56, in the transformation implementation form) until the trocar-like acute part 55a penetrates the split-capture part 54Ab of the locking portion 54A via the inside of the push tube 7A (Step 13bS: insertion of anvil-assembly connecting aid).

Subsequently, as shown in FIG. 28, the push-tube drive motor pushes the tube 7A forward (at this time, the diameter of the locking portion 54A is at its maximum), and at the same time pushes forward the insertion body 2A and the anvil-assembly connecting aid 55, and also causes the trocar-like acute part 55a of the anvil-assembly connecting aid 55 to contact the inside of the acute-part coupling hole 34Ae at the rear end of the anvil shaft 34A (see FIG. 32) (Step 13cS: contacting anvil-assembly connecting aid to anvil shaft). At this time, according to need, by operating the anvil-attitude control system it is possible to appropriately adjust the incline angle of the anvil shaft 34A by observing the diseased or defective site from outside the intestinal tract T by using the endoscope 600, or from inside the intestinal tract on the head-assembly side (in the direction of the anus) T2 by using the capsule endoscope 150.

As shown in FIG. 32, by applying the anvil-attitude control system, the trocar-like acute part 55a of the anvil-assembly connecting aid 55 is made to contact the inside of the acute-part coupling hole 34Ae at the rear end of the anvil shaft 34A, and, under this condition, by setting a base point (temporally fixed point) at the trocar-like acute part 55a, the anvil-attitude control system automatically controls the attitude of the anvil assembly 3A, referring to the target angle of the anvil shaft 34A, which is predetermined to almost agree with the angle data of the head assembly 4A, which are the angles measured by the Y0-axis, Z0-axis-angle sensors 402, 403 at that time (Step 14S: controlling attitude of anvil assembly).

In controlling the anvil assembly attitude 14S, in addition to using the endoscope 600 from the outside the intestinal tract T to observe and confirm said control situation, the capsule endoscope 150 is used to observe and confirm that control situation from inside the intestinal tract T.

After making the main axis (central axis) (X axis) of the anvil shaft 34A and the main axis (central axis) (X0 axis) of the head assembly 4A almost align with each other by controlling the anvil assembly attitude, as shown in FIG. 29, the trocar-like acute part 55a of the anvil-assembly connecting aid 55 is pushed forward into the acute-part coupling hole 34Ae at the rear end of the anvil shaft 34A, and the insertion body 2A is pushed forward to the anvil assembly 3A side, and the trocar-like acute part 55a of the anvil-assembly connecting aid 55 is inserted into the acute-part coupling hole 34Ae at the rear end of the anvil shaft 34A. The lock-adjusting-pipe drive motor forces the lock-adjusting pipe 53A to move forward and also forces the locking portion 54A to close by decreasing the diameter of the locking portion 54A in order to capture and lock the locked portion 35A of the anvil shaft 34A (Step 14aS: capture/locking of anvil shaft).

After confirming said locking condition of the anvil shaft by using the endoscope 600 from outside of the intestinal tract T and/or operating the capsule endoscope 150 from inside the remainder of the intestinal tract T2, the anvil-assembly connecting aid 55 is retracted rearward to inside the push tube 7A, and the anvil-assembly connecting aid 55 is withdrawn from the rear end opening 7Ae (or rear end 56b of the guide pipe 56 in the transformation implementation form) of the push tube 7A (Step 14bS: withdrawal of anvil-assembly connecting aid from intestinal tract).

Next, as shown in FIG. 30, while maintaining said locking condition of the anvil shaft, the push-tube drive motor and the lock-adjusting-pipe drive motor cause the push tube 7A and the lock-adjusting pipe 53A, respectively, to retract to their respective recess positions, and then the anvil assembly 3A and the head assembly 4A are made to approach and connect with each other (Step 15S: connecting and locking anvil assembly to head assembly). At this time, as shown in FIG. 8, the anvil assembly 3A is connected to and locked with the head assembly 4A, keeping between them a predetermined gap E, which almost equals the sum of the thicknesses of the remainders of the intestinal tract on the anvil-assembly side (in the direction of the mouth) T1 and the head-assembly side (in the direction of the anus) T2.

In addition to using the endoscope 600 to confirm, from outside the intestinal tract T, said step (15S) of connecting and locking the anvil assembly to the head assembly, the capsule endoscope 150 also is used, from inside the remainder of the intestinal tract T2, for that same purpose.

Next, in the same way as with Embodiment 1, circular anastomosis of the two cut-end sections of the remainder of the intestinal tract on the anvil assembly 3A side (in the direction of the mouth) T1 and the intestinal tract on the head assembly 4A side (in the direction of the anus) T2 is performed, whereby the two end-sections are connected with each other and rehabilitated again in an interconnected condition (by cutting off and removing the two intestinal-tract parts T4, T5 on the respective purse-string-like linear-stapling suturing sites T1a, T2a), and by withdrawing the circular anastomosis surgical stapler from the intestinal tract 17S, the intestinal-tract parts T4, T5 of the two cauterized openings T1b, T2b of the purse-string-like linear-stapling suturing sites which had been left inside the circular (annular) cutter 45 are removed from the anus Ma together with the circular anastomosis surgical stapler 1A.

In the method of Embodiment 2 for use in NOTES, the diseased or defective site T3 of the hollow organ (intestinal tract) T is cut off under the condition that the anvil assembly 3A is separated from the head assembly 4A, and the respective cut-end sections of the remainder of the intestinal tract on the anvil-assembly side T1 and on the head-assembly side T2 are closed by purse-string-like linear-stapling suturing. After the acute part 34Aa is removed from the rear end of the operating assembly 6A, the anvil assembly 3A is reconnected to the head assembly 4A, at which time the trocar-like acute part 55a of the anvil-assembly connecting aid 55 that was inserted from the rear end of the operating assembly 6A is easily fit into the acute-part coupling hole 34Ae at the rear end of the anvil shaft 34A. Hence, the operation of reconnecting/locking of the anvil assembly 3A and the head assembly 4A becomes easy, so that the reliability of the operation is improved.

FIG. 34 is a vertical-section diagram that shows the main configuration concept of the anvil-assembly insertion aid 8 of the transformation implementation form in Embodiment 2 of the system for use in NOTES, and shows a connected condition with the anvil assembly 3A inserted in the hollow organ T. FIG. 35 is a vertical-section diagram showing the anvil assembly 3A in a disconnected condition, with the diseased or defective site T3 of the intestinal tract T cut off. At the same time, the respective cut-end sections of said remainder of the hollow organ are closed by purse-string-like linear-stapling suturing using the linear stapler 500.

The system of this transformation implementation form for use in NOTES further provides an anvil-assembly insertion aid 8 that comprises: (1) a long, flexible hollow shaft 8a, whose two ends are open, and via which the inside of the rear end of the anvil shaft 34A and the acute part 34Aa can pass; and (2) a holding part 8d installed at the rear end 8c of the hollow shaft 8a, and in which the front end 8b is inserted by the rear end of the anvil shaft 34A and the acute part 34A, whereby the anvil-assembly insertion aid 8 is inserted into the remainder of the hollow organ T and connected with the anvil assembly 3A.

The acute part 34Aa is separated from the anvil shaft 34A that is pulled by the electric guide wire 100 that is inserted via the hollow shaft 8a, and is withdrawn from the rear end 8c. The function of the anvil-assembly insertion aid 8 is described below.

Next, a method for use in NOTES that employs the system of a transformation implementation form having said circular anastomosis surgical stapler 1A, anvil-assembly insertion aid 8, and linear stapler 500, is explained, referring to FIGS. 34-36. In this method for use in NOTES, the diseased or defective site T3 of a hollow organ such as the intestinal tract is cut off and removed from the remainder of the hollow organ, after which circular anastomosis of the two cut-end sections of the remainder of the hollow organ is performed.

FIG. 36 is a block diagram showing the main procedural steps of the method of the transformation implementation form of Embodiment 2 for use in NOTES.

As is shown in FIG. 36, the method of this transformation implementation form for use in NOTES differs from the method for use in NOTES (see FIG. 33) of Embodiment 2 only in the use of the anvil-assembly insertion aid 8 after laparoscopic identification of the diseased or defective site of the intestinal tract 2S (Steps 11aS-12cS), and the other steps of 1S, 2S, 13S-17S, and 21S-25S are completely the same as in Embodiment 2. Therefore, only the differing steps of 11aS-12cS are explained below.

After said step of laparoscopic identification of the diseased or defective site of the intestinal tract 2S, the electric guide wire 100 is inserted via the rear end 8c of the hollow shaft 8a, and, at the same time, the anvil-assembly insertion aid 8 that is connected to the anvil assembly 3A, under the condition that both the rear end of the anvil shaft 34A and the acute part 4Aa are inserted inside the front end 8b of the anvil-assembly insertion aid 8 (see FIG. 34), is inserted via a natural orifice of the human body M, e.g., the anus Ma, until the front end of the anvil assembly 3A fully passes via the diseased or defective site T3 in the intestinal tract T (Step 11aS: insertion of anvil assembly and anvil-assembly insertion aid into intestinal tract). At this time, in the same way, as shown in FIG. 35 in Embodiment 2, the anvil assembly 3A is inserted until the monopolar electrode 34c at the rear end of the trocar 34Ab passes near the front-end section C1 of the diseased or defective site T3 of the intestinal tract T and moves into the intestinal tract on the anvil-assembly side T1 (see FIG. 20).

Next, by using a endoscopic tool (not shown in the figures) in the endoscope 600 to hold the anvil assembly 3A that has been inserted into the intestinal tract on the anvil-assembly side (in the direction of the mouth) T1, so that the anvil assembly 3A will not shift in position, and gradually pulling the anvil-assembly insertion aid 8, the anvil assembly 3A is separated from the front end of the anvil-assembly insertion aid 8 and is temporarily left in the intestinal tract on the anvil-assembly side T1, as shown in FIG. 35. The anvil-assembly insertion aid 8 is retracted until the front face of the front end 8b passes near C2 of the rearward side of the diseased or defective site T3 and reaches the inside of the intestinal tract on the head-assembly side T2 (Step 12aS: separation of anvil assembly). The separation of the anvil-assembly is observed and confirmed by the endoscope 600 from outside the intestinal tract T.

After the endoscope 600 confirms, via the endoscopic hole Mb or Md and through the cannula Mc, the separation of the anvil-assembly, the linear stapler 500 is inserted into near said diseased or defective site T3 of the intestinal tract T, and the following same procedural steps as in Embodiment 2 are taken: Step 21S, insertion of linear stapler into intestinal tract; Step 22S, holding one end section of diseased or defective site of intestinal tract; Step 23S, cutting off one end section of diseased or defective site of intestinal tract, and closing the corresponding cut-end section of the remainder of the intestinal tract by purse-string-like linear-stapling suturing; 24S, cutting off other end section of the diseased or defective site of the intestinal tract, and closing the corresponding cut-end section of remainder of intestinal tract by purse-string-like linear-stapling suturing; 25S, withdrawal of linear stapler from the intestinal tract. Then the diseased or defective site T3 of the intestinal tract is cut off near C1, C2 of the front-end and rear-end sections, respectively, and said site T3 is removed together with the linear stapler 500 via the endoscopic hole Mb or Md.

Next, after the diseased or defective site T3 is cut off and removed, the anvil-assembly insertion aid 8 is moved away from the remainder of the intestinal tract on the head-assembly side T2, whose cut-end section has been closed by purse-string-like linear-stapling suturing, and the anvil-assembly insertion aid 8 is removed from the anus Ma (Step 12bS: withdrawal of anvil-assembly insertion aid from intestinal tract). In this step, the anvil assembly 3A is temporarily left in the intestinal tract on the anvil-assembly side T1.

Next, the insertion body 2A of the head assembly 4A side that has been inserted by the electric guide wire 100 wired from the rear end opening 7Ae of the push tube 7A in the rear portion of the operating assembly 6A and passed via the inside of the push tube 7A, is inserted via the anus Ma into the purse-string-like linear-stapling suturing site T2a in the intestinal tract on the head-assembly side (in the direction of the anus) T2 (Step 12cS: insertion of insertion body on head-assembly-side into intestinal tract). At this step, as shown in FIG. 26, the respective purse-string-like linear-stapling suturing sites T1a, T2a on the respective anvil assembly 3A side and head assembly 4A side are brought together. The two main axes X, X0 of the anvil assembly 3A and the head-assembly side 4A almost never align with each other, being different from the condition shown in FIG. 26, so that these axes are skewed.

After this step, as now to be described, procedures similar to those of Embodiment 2 are taken in the following order: 13S, circular anastomosis is performed on the two cut-end sections T1, T2 of the remainder of the intestinal tract on the sides of the anvil assembly 3A and the head assembly 4A, respectively, which are then connected with each other and rehabilitated again in an interconnected condition; 13aS, cauterization of purse-string-like linear-stapling suturing site and withdrawal of acute part; 13bS, insertion of anvil-assembly connecting aid into intestinal tract; 13cS, contacting of anvil-assembly connecting aid to anvil shaft; 14aS, capture/locking of anvil shaft; 14bS, withdrawal of anvil-assembly connecting aid from intestinal tract; 15S, connection of anvil assembly to head assembly; 16S, circular anastomosis of the two cut-end sections of remainder of intestinal tract; 17S, withdrawal of circular anastomosis surgical stapler from intestinal tract.

In the method of the transformation implementation form in Embodiment 2 for use in NOTES, first the anvil-assembly insertion aid 8, which is easy to operate and has a simple structure, is connected with the anvil assembly 3A and then inserted via a natural orifice of the body and into the hollow organ T that has a diseased or defective site T3. Then the anvil assembly 3A is separated from the anvil-assembly insertion aid 8 and is temporarily left inside the remainder of the hollow organ T. Then, under the condition that the anvil assembly 3A and the anvil-assembly insertion aid 8 are separated near C1, C2 of the front-end and rear-end sections of the diseased or defective site T3, respectively, the linear stapler 500 is inserted via an endoscopic hole Mb of Md so that the diseased or defective site T3 can be cut off and removed from the hollow organ T. Then the anvil-assembly insertion aid 8 is withdrawn from the natural orifice, and the anvil assembly 3A is reconnected with and locked to the head assembly 4 of the insertion body 2 that has been inserted into the remainder of the hollow organ T. At this time, it is easy to perform circular anastomosis of said two cut-end sections inside of the hollow organ T.

As stated above, according to Embodiment 2 of the present invention, the insertion body 2A of the circular anastomosis surgical stapler 1A is inserted into the body via a natural orifice and into the living hollow organ T having a diseased or defective site T3, near said diseased or defective site. Then the anvil assembly 3A is separated from the head assembly 4A to a distance of between C1 and C2, corresponding to the proximity of the front end and rear end of the diseased or defective site T3 in the remainder of the hollow organ. Under this condition, the linear stapler 500 is inserted via the endoscopic hole Mb or Md, and as is observed by using another endoscope 600, the diseased or defective site T3 is cut off and removed by a procedure outside of the hollow organ T, and at the same time the respective two cut-end sections of the remainder of the hollow organ are closed by purse-string-like linear-stapling suturing, after which the circular anastomosis surgical staplers 1A can automatically or semiautomatically perform circular anastomosis of the two cut-end sections T1, T2 of the hollow organ from inside the hollow organ T. Therefore, by eliminating the existing need for a large-scale abdominal incision and reducing the operating time and invasiveness of the surgical procedures, it is possible to provide a system and method for use in NOTES that is improved in regard to the operability of the surgical devices, the reliability of operation, and economic efficiency.

Also, in addition to the above-described embodiments of the transformation implementation form of the invention, each member of the circular anastomosis surgical stapler 1, 1A, the linear stapler 500, and the shape and configuration of the mechanisms can be changed as desired.

For example, FIG. 37 is a vertical-section diagram showing the coupled condition of an anvil assembly 3D and a head assembly 4D of the circular anastomosis surgical stapler in one additional transformation implementation form. In order to make it easier to understand the explanation, the same alphanumeric reference characters are assigned to the same function members as in the head assembly 4 in Embodiment 1, even if the shape is partly different.

The head assembly 4D in this transformation implementation form differs from the head assembly 4 in Embodiment 1 in that here a locking portion 54 that detachably locks the locked portion 35 of the anvil shaft 34 is formed at the rear end 53a of the connecting pipe 53. Because the rear end of the connecting pipe 53 is similar to that of Embodiment 1 and is fixed to the inside of the operating assembly (not shown in the figures), the movement of the locking portion 54 at the front end 53a of the connecting pipe 53 is also restrained in the direction of the main axis (X0 axis) relative to the head assembly 4D.

The front end of the locking portion 54 of this transformation implementation form is, as shown in FIG. 37, arranged up to near the front end of the head assembly 4D, and the locked portion 35 that is fitted to the locking portion 54 is arranged near the rear end of the anvil shaft 34.

In this transformation implementation form for carrying out the invention, by moving the push tube 7 forward with the release of the electric guide wire 100, and, at the same time, by driving the anvil assembly 3D via the anvil shaft 34 (at this time, the head assembly 4D may be separated from the anvil assembly 3D by retracting the head assembly 4D), the anvil assembly 3D is unlocked and separated from the head assembly 4D.

In contrast, by pulling the electric guide wire 100 in parallel with moving the push tube 7 rearward and pulling the anvil assembly 3D toward the head assembly 4D side (at this time, it is possible to move the head assembly close to the anvil assembly 3D), operating the anvil-attitude control mechanism, which is similar to that of Embodiment 1, makes the two axis centers between the main axis (X axis) of the anvil shaft 34 and the main axis (X0 axis) of the head assembly 4D almost align with each other. Then the anvil shaft 34 is fit in the push tube 7 and it connects and locks the locked portion 35 of the anvil shaft 34 with the locking portion 54 at the front end 53a of the connection pipe 53, whereby the anvil shaft 34 is locked to the head assembly 4D.

Also, FIG. 38 is a vertical-section diagram of the head assembly 4E showing the opening condition of the locking portion 54B in the circular anastomosis surgical staplers in an additional transformation implementation form of Embodiment 2. In order to make it easier to understand the explanation, the same alphanumeric reference characters are assigned to the same function members as in the head assembly 4A (see FIG. 28) of Embodiment 2, even if their shapes are partly different.

In the circular anastomosis device 1A of Embodiment 2, the flexible support 54Ac (see FIG. 28) that flexibly supports the split-capture part 54Bc by bending the flexible support 54Ac and freely expanding its diameter from the axis center to the outer circumference, can be replaced, as shown in FIGS. 38(a) and 38(b), by straight-shaped split-capture support members 54Bc made of high-stiffness metal stock such as titanium, SUS (stainless used steel), or the like, which are supported at the front end 7Aa of the push tube 7A. There can also be employed a transformation implementation form of the invention that is provided with a different shaft-support configuration that includes a spring 57 and that will have spring power in the direction of increasing the diameter of the above-mentioned split-capture support members 54Bc.

As shown in FIG. 38(b), in the shaft-support configuration of the split-capture support members 54Bc, the bracket rear end 54Bca that is set up in a split-capture support member 54Bc is supported in free rotation by the bracket 7aa that is set at the front end 7Aa of the push tube 7A via the stem (shaft) member 58. Further, one end 57a of the spring 57 (a torsion spring) that is inserted by the shaft member 58 is fixed at the front end 7Aa of the push tube 7A, and the other end 57b is fixed at the split-capture support member 54Bc, respectively. By this spring 57, which has spring power in the diameter-increasing direction, the diameter of the split-capture support member 54Bc, on whose front end the split-capture part 54Ab is formed, is increased.

Depending on the shaft (pivoting)-support configuration, such as the split-capture support members 54Bc, the front end 53Ba, whose diameter is larger than that of the lock-adjusting pipe 53B, moves forward and, as shown by the two dotted lines in FIG. 38(a), by pressing the split-capture part 54Ab from the outside to close in the diameter-decreasing direction, and in contrast and as the opposite operation, by retracting the front end 53Ba of the lock-adjusting pipe 53B from the split-capture support members 54Bc, it becomes possible to easily expand the split-capture part 54Ab to be fully open, as shown in FIG. 38(a).

INDUSTRIAL APPLICABILITY

The system of the present invention for use in NOTES, being equipped with a circular anastomosis surgical stapler and a linear stapler, and including a heretofore existing endoscope, eliminates the existing need for large-scale abdominal incisions and reduces the operating time and invasiveness of surgical procedures, thereby provide a system and method for use in NOTES that is improved in the operability of the surgical devices used, the reliability of the operation, and economic efficiency, so that it is possible to contribute to revolutionary progress in the field of surgery of a hollow organ of a body.

ALPHANUMERIC CHARACTERS USED IN THE DRAWINGS AND TEXT 1, 1A circular anastomosis surgical stapler
1S making of endoscopic hole
2, 2A insertion body
2S laparoscopic identification of diseased or defective site of intestinal tract
3, 3A, 3D anvil assembly
4, 4A, 4B, 4C, 4D head assembly 5, 5A, 5B, 5C support shaft
6, 6A, 6a, 6C operating assembly
7, 7A, 7B, 7C push tube
7a, 7Aa, 7Ba, 7Ca front end
7b roller-guide aperture
7Aaa bracket
7Ab near to rear end
7Bc, 7Cc end bracket
7Bd, 7Cd, 7Ae rear-end opening
7Af, 7Bf roller-guide aperture
7g roller guide aperture
8 anvil-assembly insertion aid
8a hollow shaft
8b front end
8c rear end
8d holding part
10 anastomotic staple
11S insertion of circular anastomosis surgical stapler into intestinal tract
11aS insertion of anvil assembly and anvil-assembly insertion aid into intestinal tract (hollow organ)
12S, 12aS releasing anvil assembly from head assembly
12bS withdrawal of anvil-assembly insertion aid from intestinal tract
12cS insertion of insertion body on head-assembly side into intestinal tract
13S cauterization of purse-string-like linear-stapling suturing site
13aS withdrawal of acute part
13bS insertion of anvil-assembly connecting aid into intestinal tract
13cS contacting anvil-assembly connecting aid with anvil shaft
14S controlling attitude of anvil assembly
14aS capturing/locking of anvil shaft
14bS withdrawal of anvil-assembly connecting aid from intestinal tract
15S connecting/locking anvil assembly to head assembly
16S circular anastomosis of cut-end sections of remainder of intestinal tract
17S withdrawal of circular anastomosis surgical stapler from intestinal tract
21S insertion of linear-stapling/cutting device (linear stapler) into intestinal tract (hollow organ)
22S holding one end section of diseased or defective site of intestinal tract
23S cutting off of that end section of diseased or defective site of intestinal tract, and closing by purse-string-like linear-stapling suturing of that end section of remainder of intestinal tract
24S cutting off of other end section of diseased or defective site of intestinal tract, and closing by purse-string-like linear-stapling suturing of that other end section of remainder of intestinal tract
25S withdrawal of linear-stapling/cutting device (linear stapler) from intestinal tract
30 anvil-assembly-attitude control mechanism
31 anvil
31a groove portion of anvil
31b staple-forming grooves
32 bracket
33 biaxial oscillating mechanism (gimbal mechanism)
33a second frame
33b third frame
33c anvil-shaft support
33e noninterference hole
33f first frame 34 anvil shaft
34a insulator
34Aa acute part
34Ad connecting shaft portion
34Ae acute-part coupling hole
34b, 34Ab trocar
34c monopolar electrode
35, 35A "passive" locking portion of anvil shaft (to couple with "active" locking portion 54, 54A, 54B of head assembly)
35a, 35Aa spline grooves
35b, 35Ab, 54b slope
36 end cap
37 lining washer
38 flexible covering
41 outer casing of head
41a, 41b bracket
41c, 41d actuator mounting hole
42 staple/cutter driver
42a rear face
43 staple-driver driving finger
44 staple cartridge
44a staples accommodation slot
45 circular (annular) cutter
46, 47 push-tube driving mechanism
47a, 48a, 49a rod end (of microlinear actuator)
48, 66 staple/cutter driver
49, 68 lock-adjustment-tube driving mechanism
51 outer tube
52 driver tube
52a male-screw tube
52b male screw
53 connecting tube
53a, 53Aa, 53Ba front end
53A, 53B lock-adjustment tube
53Ab rear end
53Bc end bracket
53Bd rear-end opening
54, 54A, 54B "active" locking portion of head assembly (to couple with "passive" locking portion 35, 35A of anvil shaft)
54a, 54Aa spline teeth
54Ab split-capture part
54Ac flexible support
54Bc split-capture-part support
54Bca rear end of bracket
55 anvil-assembly connecting aid
55a trocar-like acute part
55b shaft
56 guide tube
56a distal end
56b rear end
57 spring
57a one of the two ends of spring
57b the other end of spring
58 stem
61 operating-assembly housing
61a rear end
61c motor mounting hole
61d indicator window
63 drive shaft
63a pinion
64 push-tube drive mechanism
65 externally-toothed rotating nut
65a external tooth
65b female screw
65c hollow rear portion 67 push-tube drive mechanism
91 staple/cutter driver motor
100 thin wire guide (electric guide wire)
110 take-up unit
120 endoscope
121 insertion-tube body
140, 140A (wireless) operating unit
150 capsule endoscope
300 Y-axis servomotor
301 Z-axis servomotor
302, 412 battery
303, 403, 410 wireless transmitter/receiver
304, 411 antenna
305 Y-axis-angle sensor
306 Z-axis-angle sensor
307 anvil-shaft-rotation motor (rotary means)
310 angle-command generator
311 angle detector
312 command-calculation unit
320 drive-control unit
321 Y-axis controller
322 Z-axis controller
401 Y0-axis-angle sensor
402 Z0-axis-angle sensor
500 linear stapler (linear-stapling/cutting device)
501 main body
502 operating assembly
503 end effector
504 upper jaw
505 lower jaw
506 support shaft
507 jaw-opening/closing motor
508 linear-staple/cutter driving motor
509 (wireless) operating unit
510 staple cartridge
511 one or more linear rows of staples
512 staples accommodation slot
520 linear-staple/cutter driving mechanism
530 upper-jaw opening/closing mechanism
540 upper-jaw body
541 groove
542, 550a dovetail-groove-type slide groove
543 rack
554a male screw
544 staple guide
544a grooves for forming staples
550 lower-jaw body
551 channel
552 upper-shaft support hole
553 lower-shaft support hole
554 upper-jaw opening/closing driving shaft
554a pinion
555 linear-staple/cutter driving shaft
555a male-screw portion for driving front-end linear-staple/cutter
555b male-screw portion for driving rear-end linear-staple/cutter
556 front-end linear-staple driver
556a, 557a slope
557 rear-end linear-staple driver
557b female screw
558 front-end linear cutter
558a, 559a concave notch
559 rear-end linear cutter
560, 562 flexible drive shaft
561, 563 coupling C1 near to front end of diseased or defective site of hollow organ (intestinal tract) T3
C2 near to rear end of diseased or defective site of hollow organ (intestinal tract) T3
M living thing (e.g., living body, human body, body)
Ma natural orifice (e.g., anus, mouth, or the like)
Mb endoscopic hole via which endoscopic instruments can be inserted
Mc cannula
Md endoscopic hole via which endoscopic instruments can be inserted
T hollow organ (e.g., digestive tract, including intestinal tract)
T1 hollow-organ (e.g., intestinal tract) portion on anvil-assembly side (in direction of mouth, or distal end)
T1a, T2a purse-string-like linear-stapling suturing site (cutting-end section of remainder of hollow organ (intestinal tract))
T1b, T2b cauterized opening (of purse-string-like linear-stapling suturing site)
T2 portion of tract (e.g., intestinal tract) on head-assembly side (in direction of anus or rear end)
T3 diseased or defective site (of hollow organ)
T4 intestinal tract on the opening T1b side (at purse-string-like linear-stapler suturing site T1a of area of tract [e.g., intestinal tract] on anvil-assembly side [in direction of mouth or distal end])
T5 intestinal tract on the opening T2b side (at purse-string-like linear-stapling suturing site T2a of area of tract [e.g., intestinal tract] on head-assembly side [in direction of anus or rear end])

The invention claimed is:

1. A system for use in Natural Orifice Transluminal Endoscopic Surgery, with said system including a circular anastomotic surgical stapler that comprises:
an anvil assembly that has an anvil shaft from which a trocar protrudes rearward along a main axis or X-axis at the rear end of the anvil assembly so that the anvil assembly is used as the front end of the circular anastomotic surgical stapler;
an insertion body that is positioned opposite to the anvil assembly and that includes
(1) a head assembly that has (a) a circular cutter or annular blade for cutting off, in the cylindrical direction, a specified section of a hollow or tubular organ, and (b) one or more annular rows of anastomotic staples for use in circular anastomosis of two cut-end sections of a remainder of the hollow organ, and
(2) a long, flexible support shaft that is connected to the head assembly;
an operating assembly that is connected to the insertion body and that controls the driving of the circular cutter or annular blade and the anastomotic staples;
a thin guide wire that is inserted via the insertion body and that is connected to an acute or rear end of the trocar so as to be capable of being taken up and released; and
a coupling or engaging mechanism that includes a locked portion and a locking portion that are engageable with each other, with the locked portion provided at the anvil shaft and the locking portion provided at a main axis of the head assembly, and that releasably mounts the anvil assembly to the head assembly, with the insertion body to which the anvil assembly is connected being inserted into a diseased or defective hollow organ via a natural orifice of a living body;
said anvil assembly is detached or removed from the head assembly and is temporarily left at the front-end section of the diseased or defective site of the hollow organ, and a head-assembly-side insertion body retracts to a rear-end section of the diseased or defective site, so as to create a space between the anvil assembly and the head assembly of the insertion body;

after said space has been created between the anvil assembly and the head assembly of the insertion body, there is inserted into the body—via an endoscopic hole to near the diseased or defective site of the hollow organ, a linear cutting/stapling device or linear stapler that has one or more linear cutters that have a noninterference concave notched structure and that are used to cut off, straight in a transverse direction, only a specified section of the hollow organ without cutting off said thin guide wire, and one or more linear rows of suture staples that are used to staple the respective cut-end sections of the remainder of the hollow organ straight in the transverse direction;

said diseased or defective site of the hollow organ is cut off straight in the transverse direction and removed from the remainder of the hollow organ, and the respective cut-end sections of the remainder of the hollow organ are at the same time closed by purse-string-like linear-stapling suturing straight in the transverse direction by a procedure outside the hollow organ by using the linear stapler; and then the circular anastomotic surgical stapler performs circular anastomosis of the two cut-end sections of the remainder of the hollow organ, and at the same time cuts off, by a procedure inside the hollow organ, the two cut-end sections that had been closed by purse-string-like linear-stapling suturing of the remainder of the hollow organ, so that the sections are again interconnected;

the thin wire guide is an electric guide wire consisting of an electric conductor, with the front end of the electric guide wire being connected to the acute or rear end of the trocar via a monopolar electrode, with the trocar either consisting of an insulator or being releasably connected to the rear end of the anvil shaft via an insulator, and with respective purse-string-like linear-stapling suturing sites of the remainder of the hollow organ on the anvil-assembly side and the head-assembly side being (1) cauterized successively by conducting a monopolar current to the monopolar electrode via the electric guide wire that has been taken up, and (2) inserted by the trocar via both of said suturing sites so that said suturing sites will be opened.

2. A system according to claim 1 for use in NOTES, and wherein there are accommodated near the connection between the head assembly and the support shaft: (a) a push-tube drive mechanism that moves a push tube forward or backward, with the push tube being provided to allow the anvil assembly to connect with or detach from the head assembly, (b) a staple/cutter driver mechanism that drives the anastomotic staples and the circular cutter or annular blade, and (c) a take-up unit that takes up the thin guide wire; with the operations of the mechanisms and take-up unit being remotely controlled via the operating assembly.

3. A system according to claim 2, for use in NOTES, and wherein a wireless transmitter/receiver and a battery are further provided near the connection between the head assembly and the support shaft, with the push-tube drive mechanism, the staple/cutter driver mechanism, and the take-up unit being controlled by wireless remote control.

4. A system according to claim 1, for use in NOTES, and wherein the coupling or engaging mechanism includes
(1) the locked portion of a convex-shaped anvil shaft that is provided near the trocar;
(2) a split-capture part that is mounted on the center of the head assembly and that is divided circumferentially into a plurality of pieces so as to form a concave shape, and that engageably fits on the locked portion so as to capture the locked portion;
(3) the locking portion, which is provided at the front end of a push tube and is able to move forward and backward so as to allow the anvil assembly to connect with or detach from the head assembly, and that has a plurality of resilient support members that flexurally and elastically support the split-capture part so as to open, without restraint in a diameter-expanding direction, the respective pieces of the split-capture part from a main axis or X0-axis of the head assembly; and
(4) a lock-adjustment tube that fits on the push tube so as to be able to move forward and backward, that acts so that the front end moves forward to the rear end of the locking portion, so as to press the resilient support member from the outside and to close the split-capture part in a diameter-reducing direction, and so that the front end moves backward from the resilient support member so as to open the split-capture part in the diameter-expanding direction.

5. A system according to claim 1, for use in NOTES, and wherein are accommodated near the connection between the head assembly and the support shaft:
(1) a push-tube drive mechanism that moves a push tube forward or backward, with said push tube being provided to allow the anvil assembly to connect with or detach from the head assembly,
(2) a lock-adjustment tube mechanism that moves a lock-adjustment tube forward and backward so as to allow the locking portion to become engaged with and disengaged from the locked portion, and
(3) a staple/cutter driver mechanism that allows the anastomotic staples and the circular cutter or annular blade to be driven or pushed out or retracted; with the operations of said mechanisms remotely controlled via the operating assembly.

6. A system according to claim 5, for use in NOTES, and wherein a wireless transmitter/receiver and a battery are further provided near the connection between the head assembly and the support shaft, with the push-tube drive mechanism, the lock-adjustment tube mechanism, and the staple/cutter driver mechanism being controlled by wireless remote control.

7. A system according to claim 1, for use in NOTES, and wherein the monopolar electrode is buried in the rear end of the trocar, with a small area of the monopolar electrode being exposed at the outer surface of the rear end of the trocar.

8. A system according to claim 1, for use in NOTES, and wherein the monopolar electrode is exposed in a narrow band-like manner of appropriate length in the axial direction at the outer surface of the rear end of the trocar.

9. A system according to claim 1, for use in NOTES, and wherein the anvil shaft to which the trocar is coupled is also coupled to a rotary means by being rotatably supported by the anvil-shaft support, and is rotated by the rotary means when a monopolar current is conducted to the monopolar electrode.

10. A system according to claim 1, for use in NOTES, and wherein the acute part penetrates both of the purse-string-like linear-stapling suturing sites or on the anvil-assembly side and head-assembly side that are successively cauterized via the trocar, and then is detached or removed from the anvil shaft so as to be pulled into the head assembly.

11. A system according to claim 1, for use in NOTES, and wherein when the anvil assembly is reconnected with the head assembly, the acute part is separated from the rear end of the anvil shaft by pulling the thin guide wire, and after the acute part is withdrawn from a rear-end opening where a push tube is extended to a rearward face of the operating assembly, and wherein there is provided an anvil-assembly connecting aid that (a) is inserted so as to be able to be withdrawn from the rear end of the operating assembly to the front end of the head assembly via the inside of a support shaft, (b) consists of a trocar-like acute part, with the front end thereof being formed like a trocar, penetrating via a split-capture portion of the locking part, (c) has a long flexible shaft that is connected to the trocar-like acute part and that aids the anvil assembly in again being coupled with the head assembly, and (d) assists said connection by inserting a trocar-like acute part that is at the front end of said shaft into inside of the rear end of the anvil shaft from an acute part of the anvil shaft side has been separated.

12. A system according to claim 11, for use in NOTES, and wherein the anvil assembly contains a first anvil-assembly-attitude control mechanism that supports the anvil shaft and that automatically controls the attitude of the anvil assembly in relation to the anvil shaft so that the central or main axis of the anvil shaft substantially corresponds to the main axis or X0-axis of the head assembly.

13. A system according to claim 12, for use in NOTES, and wherein the first anvil-assembly-attitude control mechanism includes (a) a biaxial oscillating mechanism that can oscillate along two axes or Y-axis and Z-axis that meet at right angles with the main axis of the anvil shaft or X-axis, (b) angle sensors, mounted on the connection of the anvil shaft, for the Y-axis and Z-axis, and (c) a drive means that drives the biaxial oscillating mechanism along the Y-axis and Z-axis, respectively.

14. A system according to claim 13, for use in NOTES, and wherein the drive means consists of servomotors that respectively control the drive of the biaxial oscillating mechanism along the Y-axis and the Z-axis.

15. A system according to claim 14, for use in NOTES, and further including a second anvil-assembly-attitude control mechanism that comprises:
   a head-assembly-side transmitter/receiver that is provided inside the head assembly and that wirelessly transmits the output of angle sensors that are located along the two axes or Y0-axis and Z0-axis and that meet at right angles with the central axis or X0-axis of the head assembly;
   an anvil-assembly-side transmitter/receiver that receives from the head-assembly-side transmitter/receiver the output of the angle sensors that are along the two axes or Y0-axis and Z0-axis;
   an angle-command generator (1) that has (a) an angle detector into which are input the output of angle sensors that located along the Y-axis and Z-axis of the second anvil-assembly-attitude control mechanism and the output of angle sensors located along the Y0-axis and Z0-axis from the anvil-assembly-side transmitter/receiver, and that detects their respective angle data and (b) a command-calculation unit that calculates respective desired rotation angles of a second frame and the anvil shaft based on the angle data from the angle detector, and (2) that generates, based on the desired rotation angles, angle-command values of the second frame and the anvil shaft; and
   a drive-control unit that has a Y-axis controller and Z-axis controller that, based on the angle-command values from the angle-command generator, individually servo-control the Y-axis servomotor and Z-axis servomotor, respectively;
   and there is provided an anvil-shaft target angle that substantially corresponds to the angle data of the head assembly when the rear end of the trocar is set as a reference point or a temporary fixed point under the condition that the anvil assembly is pulled by the thin wire guide so as to contact the inside of the locked portion of the head assembly or the inside of the front end of a push tube to which the locked portion is connected when the anvil assembly is again being coupled to the head assembly, whereby the attitude of the anvil assembly is automatically controlled.

16. A system according to claim 14, for use in NOTES, and further including a third anvil-assembly-attitude control mechanism that comprises:
   a head-assembly-side transmitter/receiver that is provided inside the head assembly and that wirelessly transmits the output of angle sensors located along two axes or Y0-axis and Z0-axis that meet at right angles with a main axis or X0-axis of the head assembly;
   an anvil-assembly-side transmitter/receiver that receives from the head-assembly-side transmitter/receiver the output of angle sensors located along the two axes or Y0-axis and Z0-axis;
   an angle detector into which are input the output of angle sensors located along the Y-axis and Z-axis of the third anvil-assembly-attitude control mechanism and the output of angle sensors located along the Y0-axis and Z0-axis from the anvil-assembly-side transmitter/receiver and that detects the respective angle data;
   an angle-command generator that has a command-calculation unit that calculates the respective desired rotation angles of a second frame and the anvil shaft based on the angle data from the angle detector, and that generates angle-command values of the second frame and the anvil shaft based on the desired rotation angles;
   a drive-control unit that has a Y-axis controller and Z-axis controller that individually servo-control the Y-axis servomotor and Z-axis servomotor, respectively, based on the angle-command values from the angle-command generator;
   and wherein a target angle of the anvil shaft is provided so that the target angle substantially corresponds to the angle data of the head assembly when the trocar-like acute portion of the anvil-assembly connecting aid is set as a reference point or a temporary fixed point under the condition that the insertion body to be inserted into the hollow organ and a push tube via which the anvil-assembly connecting aid is inserted, both of which are located on the side of the head assembly, are pushed and advanced so as to permit the trocar-like acute portion to contact the inside of the acute-portion coupling hole while the anvil assembly is again being coupled to the head assembly, whereby the attitude of the anvil assembly is automatically controlled.

17. A system according to claim 13, for use in NOTES, and wherein the biaxial oscillating mechanism consists of a gimbal mechanism in which a second frame able to oscillate along the Y-axis is provided on a first frame that is fixed inside the anvil assembly, and an anvil-shaft support able to oscillate along the Z-axis and supporting the anvil shaft is provided on the second frame.

18. A system according to claim 1 for use in NOTES, and wherein there is provided a wireless endoscope device or capsule endoscope device, with the front-end assembly of the endoscope arranged in the vicinity of the front end of the head assembly.

19. A system for use in NOTES, with said system including a circular anastomotic surgical stapler that comprises:
- an anvil assembly to whose rear end is connected an anvil shaft whose rear end connects releasably to an acute part that includes a trocar, so that said anvil shaft protrude rearward along a main axis or X-axis so that the anvil assembly is used as the front end of the circular anastomotic surgical stapler;
- an insertion body that is positioned opposite to the anvil assembly and that includes (a) a head assembly that has (1) a circular cutter or annular blade for cutting off in the cylindrical direction a specified section of a hollow or tubular organ, (2) one or more annular rows of anastomotic staples that are used in circular anastomosis of two cut-end sections of the remainder of the hollow organ, and (b) a long, flexible support shaft that is connected to the head assembly;
- an operating assembly that is connected to the insertion body and that controls the driving of the circular cutter or annular blade and one or more rows of anastomotic staples;
- a thin guide wire that is inserted via the insertion body and that is connected to an acute or rear end of the trocar so as to be capable of being taken up and released; and
- a coupling or engaging mechanism that includes a locked portion and a locking portion that are engageable with each other, with the locked portion provided at the anvil shaft and the locking portion provided at a main axis of the head assembly, and that releasably mounts the anvil assembly to the head assembly;
- wherein the insertion body to which the anvil assembly is connected is inserted via a natural orifice of the body into the hollow organ that has a diseased or defective site;
- said anvil assembly is detached or removed from the head assembly and is temporarily left at the front end of the diseased or defective site of the hollow organ, and a head-assembly-side insertion body retracts to a rear-end portion of the diseased or defective site, so as to create a space between the anvil assembly and the insertion body;
- after said space has been created between the anvil assembly and the insertion body, there are inserted into the body at the diseased or defective site of the hollow organ via an endoscopic hole, a linear stapler that has one or more linear cutters that have a noninterference concave notched structure and that are used to cut off, straight in a transverse direction, only a specified section of the hollow organ without cutting off said thin guide wire, and one or more linear rows of suture staples that are used to staple the respective cut-end sections of the remainder of the hollow organ straight in the transverse direction;
- said diseased or defective site of the hollow organ is cut off straight in the transverse direction and removed from the remainder of the hollow organ, and at the same time the respective cut-end sections of the remainder of the hollow organ are closed by purse-string-like linear-stapling suturing straight in the transverse direction by a procedure outside the hollow organ using the linear stapler; and then
- said circular anastomotic surgical stapler performs circular anastomosis of the two cut-end sections of the remainder of the hollow organ, and at the same time cuts off the two cut-end sections that have been closed by purse-string-like linear-stapling suturing of the remainder of the hollow organ by a procedure inside the hollow organ, so that the sections are again interconnected;
- the thin wire guide is an electric guide wire consisting of an electric conductor, with the front end of the electric guide wire being connected to the acute or—rear end of the trocar via a monopolar electrode,
- with the trocar either consisting of an insulator or being releasably connected to the rear end of the anvil shaft via an insulator,
- and with the respective purse-string-like linear-stapling suturing sites of the remainder of the hollow organ on the anvil-assembly side and the head-assembly side being (1) cauterized successively by conducting a monopolar current to the monopolar electrode via the electric guide wire that has been taken up, and (2) said respective purse-string-like linear-stapling suturing sites inserted by the trocar via both of said suturing sites so that said suturing sites will be opened.

20. A system for use in NOTES, with said system including a circular anastomosis surgical stapler that comprises:
- an anvil assembly that has an anvil shaft from which a trocar protrudes rearward along a main axis or X-axis at the rear end of the anvil assembly so that the anvil assembly is used as the front end of the circular anastomotic surgical stapler;
- an insertion body that is positioned opposite to the anvil assembly and that includes
  (1) a head assembly that has (a) a circular cutter or annular blade for cutting off, in the cylindrical direction, a specified section of a hollow or tubular organ, and (b) one or more annular rows of anastomotic staples for use in circular anastomosis of two cut-end sections of the remainder of the hollow organ, and
  (2) a long, flexible support shaft that is connected to the head assembly;
- an operating assembly that is connected to the insertion body and that controls the driving of the circular cutter or annular blade and the anastomotic staples;
- a thin guide wire that is inserted via the insertion body and that is connected to an acute or rear end of the trocar so as to be capable of being taken up and released; and
- a coupling or engaging mechanism that includes a locked portion and a locking portion that are engageable with each other, with the locked portion provided at the anvil shaft and the locking portion provided at the main axis of the head assembly, and that releasably mounts the anvil assembly to the head assembly, with the insertion body to which the anvil assembly is connected being inserted into a diseased or defective hollow organ via a natural orifice of a body;
- and wherein there is further provided (1) an anvil-assembly connecting aid that consists of a long, flexible, hollow shaft whose two ends are open and via which the rear end of the anvil shaft and the trocar portion can be inserted, and (2) a holding part that is provided at the rear end of the hollow shaft and that is inserted into the hollow organ under the condition that the rear end of the anvil shaft and the trocar portion are inserted into the front end of the hollow shaft so that the anvil assembly is coupled to the anvil-assembly connecting aid;
- said anvil assembly inserting aid to which said anvil assembly is connected is inserted into the hollow organ having a diseased or defective site through a natural orifice of the body;
- said anvil assembly is detached or removed from said anvil-assembly inserting aid and is temporarily left near the front-end section of the diseased or defective site of the hollow organ, and said anvil-assembly inserting aid retracts to the rear-end section of said diseased or defective site, so as to create a space between the anvil assembly and said insertion body;

after said space has been created between said anvil assembly and said anvil-assembly inserting aid, a linear-cutting/stapling device or linear stapler that has one or more linear cutters that have a noninterference concave notched structure, and that are used to cut off, straight in a transverse direction, only a specified section of the hollow organ without cutting off said thin guide wire, and one or more linear rows of suture staples that are used to staple the respective cut-end sections of the remainder of the hollow organ straight in the transverse direction;

said diseased or defective site of the hollow organ is cut off, straight in the transverse direction, and is then removed from the remainder of the hollow organ, and, at the same time, the respective cut-end sections of the remainder of the hollow organ are closed by purse-string-like linear-stapling suturing straight in the transverse direction by a procedure outside the hollow organ by using said linear stapler; and then, said anvil-assembly inserting aid retracts from a remainder of the intestinal tract on the head assembly side, and is withdrawn from the natural orifice of the body;

said insertion body on the head assembly side is inserted from a natural orifice of the body to near the site of the purse-string-like linear-stapling suturing of the remainder of the hollow organ on the head assembly side, said circular anastomosis surgical stapler performs circular anastomosis of said two cut-end section of the remainder of the hollow organ, and at the same time cuts off said two cut-end sections that had been closed by purse-string-like linear-stapling suturing of said remainder of the hollow organ so that said sections are rehabilitated again in a normal interconnected condition;

the thin wire guide is an electric guide wire consisting of an electric conductor, with the front end of the electric guide wire being connected to the acute (rear) end of the trocar via a monopolar electrode, with the trocar consisting of an insulator or formed separately on the anvil shaft via an insulator, and with both of the purse-string-like linear-stapling suturing sites of the remainder of the hollow organ on the anvil-assembly side and the head-assembly side being (1) cauterized successively by conducting a monopolar current to the monopolar electrode via the electric guide wire that has been taken up, and (2) inserted by the trocar via both of said purse-string-like linear-stapling suturing sites so that said suturing sites will be opened.

21. A system for use in NOTES that includes a linear cutting/stapling device that comprises:
(1) an insertion body to be inserted into a body via an endoscopic hole so that endoscopic instruments can be inserted into said body, with the insertion body including
(a) an end effector that has one or more linear rows of suture staples that are positioned opposite to a first jaw of the end effector that opens and closes, linearly stapling in the straight transverse direction on the outside of the hollow organ a specified section of the hollow organ, and a second jaw of said end effector provided with a pair of linear cutters for cutting off in the transverse direction a specified section of the hollow organ, with the cutters capable of respectively moving back and forth from the respective sides of the front end and rear end of the second jaw to an intermediate area thereof, and (b) a long, flexible support shaft that is connected to the end effector; and (2) an operating assembly that controls the driving of the linear rows of suture staples and the linear cutters;
and wherein a circular anastomotic surgical stapler includes
(a) an anvil assembly that has an anvil shaft on which a trocar protrudes rearward along a main axis or X-axis at the rear end of the anvil assembly so that the anvil assembly is used as the front end of the circular anastomosis surgical stapler;
(b) an insertion body, positioned opposite to the anvil assembly and including a head assembly that has [1] a circular cutter or annular blade for cutting off, in the cylindrical direction, a specified section of a hollow or tubular organ, and [2] one or more annular rows of anastomotic staples for use in circular anastomosis of the two cut-end sections of a remainder of the hollow organ, and a long, flexible support shaft that is connected to the head assembly;
(c) an operating assembly that is connected to the insertion body and that controls the driving of the circular cutter or annular blade and anastomotic staples,
(d) a coupling or engaging mechanism that includes a locked portion and a locking portion that are engageable with each other, with the locked portion provided at the anvil shaft and the locking portion provided at the central (main) axis of the head assembly, and that releasably mounts the anvil assembly to the head assembly, and
(e) an insertion body, to which the anvil assembly is connected, which is inserted into the hollow organ that has a diseased or defective site, via a natural orifice of the body under the condition that the anvil assembly is detached from the head assembly and temporarily remains near the front end of the diseased or defective site, and the head-assembly-side insertion body retracts to near the rear end of the diseased or defective site, so as to create a space between the anvil assembly and the head assembly;
after said space has been created between the anvil assembly and the head assembly, the linear stapler is inserted into the body via an endoscopic hole near the diseased or defective site of the hollow organ, and the front-end and rear-end sections of the diseased or defective site are successively cut off straight in the transverse direction and removed from the remainder of the hollow organ by using a pair of linear cutters, and at the same time the two cut-end sections of the remainder of the hollow organ are closed by purse-string-like linear-stapling suturing straight in the transverse direction by a procedure outside of the hollow organ using the linear stapler.

22. A system according to claim 21, for use in NOTES, and wherein the pair of linear cutters of the end effector move back and forth in the direction opposite to each other due to the linear-staple/cutter-driving mechanism provided inside the second jaw.

23. A system according to claim 22, for use in NOTES, and wherein the linear-staple/cutter-driving mechanism includes a linear staple/cutter driver shaft that (1) is rotatably provided inside a channel dug facing the rear of a staple cartridge in which one or more linear rows of suture staples are accommodated, (2) is removably fit inside the second jaw or unmovable jaw facing the first jaw or opening/closing jaw, and (3) has a male screw on which reverse screws in the right and left directions are formed on either the anterior half and or the posterior half of the male screw; and front-end and rear-end staple-driving mechanisms, both of which (1) have a wedge mechanism that is threadedly engaged with the respective left and right reverse screws of the linear-staple/cutter-driving mechanism, and (2)

move back and forth in the direction opposite to each other inside the channel accompanying the reversible rotation of the linear staple/cutter driver shaft, so as to drive the one or more linear rows of suture staples; and wherein the pair of linear cutters are mounted on the respective front-end and rear-end staple-driving mechanisms in such a way that the pair of linear cutters are driven or disposed so that the blade edges thereof are positioned opposite to each other and standing in the direction of the staple cartridge.

\* \* \* \* \*